US010557175B2

(12) United States Patent
Bracken et al.

(10) Patent No.: US 10,557,175 B2
(45) Date of Patent: Feb. 11, 2020

(54) METHOD OF PREDICTING RISK OF RECURRENCE OF CANCER

(71) Applicants: THE PROVOST, FELLOWS, SCHOLARS AND OTHER MEMBERS OF BOARD OF TRINITY COLLEGE DUBLIN, Dublin (IE); UNIVERSITY COLLEGE DUBLIN, NATIONAL UNIVERSITY OF IRELAND, DUBLIN, Dublin (IE)

(72) Inventors: Adrian Bracken, Dublin (IE); Fiona Lanigan, Dublin (IE); William Gallagher, Dublin (IE)

(73) Assignees: THE PROVOST, FELLOWS, SCHOLARS AND OTHER MEMBERS OF BOARD OF TRINITY COLLEGE DUBLIN, Dublin (IE); UNIVERSITY COLLEGE DUBLIN, NATIONAL UNIVERSITY OF IRELAND, DUBLIN, Dublin (IE)

( * ) Notice: Subject to any disclaimer, the term of this patent is extended or adjusted under 35 U.S.C. 154(b) by 0 days.

(21) Appl. No.: 15/511,890

(22) PCT Filed: Sep. 18, 2015

(86) PCT No.: PCT/EP2015/071524
§ 371 (c)(1),
(2) Date: Mar. 16, 2017

(87) PCT Pub. No.: WO2016/042164
PCT Pub. Date: Mar. 24, 2016

(65) Prior Publication Data
US 2018/0148788 A1 May 31, 2018

(30) Foreign Application Priority Data

Sep. 19, 2014 (EP) ..................... 14185673

(51) Int. Cl.
| | | |
|---|---|---|
| C12Q 1/68 | (2018.01) | |
| C07H 21/04 | (2006.01) | |
| C12Q 1/6886 | (2018.01) | |
| G01N 33/574 | (2006.01) | |
| A61K 31/519 | (2006.01) | |

(52) U.S. Cl.
CPC .......... *C12Q 1/6886* (2013.01); *A61K 31/519* (2013.01); *G01N 33/57415* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | |
|---|---|---|
| 7,914,988 B1 | 3/2011 | Chudin et al. |
| 2008/0275652 A1 | 11/2008 | Sotiriou et al. |

FOREIGN PATENT DOCUMENTS

| | | |
|---|---|---|
| WO | 2005/039382 A2 | 5/2005 |
| WO | 2012/030840 A2 | 3/2012 |
| WO | 2013/011479 A2 | 1/2013 |
| WO | 2014/066796 A2 | 5/2014 |
| WO | 2014/130825 A1 | 8/2014 |

OTHER PUBLICATIONS

Barry et al. (J. of Clinical Oncology, vol. 28,No. 13, pp. 2198-2206, 2010). (Year: 2010).*
GEO Accession GSE4922 Set (May 31, 2006) (Year: 2006).*
Miller et al. (PNAS, vol. 102, No. 49, 13550-13555, Sep. 2005 (Year: 2005).*
Pawitan et al. (Breast Cancer Research, vol. 7 R953-964, 2005). (Year: 2005).*
Geng et al., "Diagnostic and prognostic value of plasma and tissue ubiquitin-like, containing PHD and RING finger domains 1 in breast cancer patients." Cancer Science 104(2):194-199 (2013).
Hui et al., "INK4a Gene Expression and Methylation in Primary Breast Cancer: Overexpression of p16INK4a Messenger RNA is a Marker of Poor Prognosis." Clinical Cancer Research 6(7):2777-2787 (2000).
Pardo et al., "Next-generation transcriptome sequencing of the premenopausal breast epithelium using specimens from a normal human breast tissue bank." Breast Cancer Research 16(2):R26 (2014).

* cited by examiner

*Primary Examiner* — Jeanine A Goldberg
(74) *Attorney, Agent, or Firm* — Nixon Peabody LLP; David S. Resnick; Nicole D. Kling

(57) ABSTRACT

A method for predicting risk of recurrence of cancer in an individual with cancer, the method comprising a step of assaying a cancer sample from the individual for positive expression of at least two genes or proteins encoded by those genes selected from the group consisting of FOXM1, UHRF1, PTTG1, E2F1, MYBL2, HMGB2, ATAD2, E2F8, ZNF367 and TCF19, wherein positive expression of the at least two genes correlates with increased risk of recurrence of cancer compared with an individual who does not exhibit positive expression of the at least two genes or proteins encoded by those genes.

18 Claims, 31 Drawing Sheets
Specification includes a Sequence Listing.

HMEC

MEF

Chisq=16.601, p-value=0, HR=7.69 (2.17-27.18)

METHOD OF PREDICTING RISK OF RECURRENCE OF CANCER

CROSS-REFERENCE TO RELATED APPLICATIONS

This application is a 35 U.S.C. § 371 National Phase Entry Application of International Application No. PCT/EP15/071524 filed Sep. 18, 2015, which designates the U.S. and claims benefit under 35 U.S.C. § 119(b) of European Provisional Application No. 14185673.2 filed Sep. 19, 2014, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Mar. 16, 2017, is named 11144PC00-Sequence-Listing-ST25.txt and is 8,349 bytes in size.

FIELD OF THE INVENTION

The invention relates to a method of predicting the risk of tumour recurrence in a subject. Specifically, the invention relates to a method of predicting the risk of early-stage node-negative breast cancer, prostate cancer and other tumour recurrence.

BACKGROUND TO THE INVENTION

Breast cancer is a heterogeneous disease which presents challenges for clinicians in predicting the likelihood of disease progression, particularly in patients where the disease is detected in the early stages. For these women, the conventional clinico-pathological parameters (tumour size, lymph node status, patient age, tumour grade, and expression of biomarkers including Estrogen Receptor (ER), Progesterone Receptor (PR), Human Epidermal growth factor Receptor 2. (Her2), Ki67) are not sufficient to characterise disease complexity and accurately predict the likelihood of tumour recurrence following adjuvant treatment or tumour removal by surgery. Therefore, due to inaccurate risk stratification, many of these patients who are inherently at a low risk of recurrence are assigned to receive chemotherapy, when in fact the majority of these women would remain cancer-free even without this toxic treatment.

In fact, it is estimated that, for node-negative, ER-positive disease, up to 85% of patients would be overtreated if given chemotherapy (Fisher et al., 2004). Furthermore, surviving patients treated with chemotherapy face a higher risk of developing a second, independent, primary cancer in unrelated tissues within their lifetime (Boffetta and Kaldor, 1994). Considering the severe side-effects, the public health burden and the future health implications of chemotherapy, the overtreatment of patients represents a major problem in the clinical management of early-stage breast cancer.

The challenge is to develop a method of accurately and reproducibly distinguishing the low-risk from the high-risk patients so that therapy can be assigned accordingly. Current guidelines often lead to differing opinions from breast oncologists as to whether to assign neoadjuvant and/or adjuvant therapy, as many are reluctant to forego neoadjuvant and/or adjuvant therapy without a reliable assessment of recurrence risk. The addition of more accurate and reliable prognostic and predictive biomarkers to the standard clinical assessment would greatly improve the ability of both doctors and patients to make more well-informed treatment decisions. Some progress is being made in this regard with the multigene assays Oncotype Dx® Breast Cancer Assay and MammaPrint™, which are currently being assessed in the Trial Assigning IndividuaLized Options for Treatment (Rx) (TAILORx) and Microarray In Node-negative and 1 to 3 positive lymph node Disease may Avoid ChemoTherapy (MINDACT) trials, respectively (Cardoso et al., 2008; Sparano, 2006). MammaPrint™ and Prosigna™ are examples of Food and Drug Agency-approved prognostic tests in this arena.

WO 2005/039382 describes a number of gene sets used in predicting the likelihood of breast cancer recurrence, otherwise known as Oncotype Dx® referred to above. The invention is related to a gene set comprising 'one or more' genes from a panel of 50 genes. WO 2104/130825 describes a gene set comprising least 4 genes from a panel of cell cycle genes for detecting risk of lung cancer. U.S. Pat. No. 7,914,988 describes a gene expression signature to predict relapse in prostate cancer, known as the GEX score. The invention is related to a gene set comprising 'all or a sub-combination of' genes from a panel of 21 genes.

The widespread use of gene expression profiling has led to a rapid expansion in the identification of gene expression signatures found to correlate with different aspects of tumour progression. These include the 'poor prognosis' (van de Vijver et al., 2002; Wang et al., 2005), 'invasiveness' (Liu et al., 2007), and 'genomic grade' (Sotiriou et al., 2006) signatures. US 2008/275652 describes how this genomic grade signature comprises at least 2 or 4 genes selected from a panel of 97 genes. However, despite the ability of these signatures to predict breast cancer prognosis, there is surprisingly little overlap between signatures. The Applicants suggest that many genes in these signatures may be 'passengers', rather than 'drivers' of tumour progression. Recent advances in genome-wide reverse engineering have made it possible to successfully identify regulatory interactions between transcription factors and downstream genes which were causal rather than correlative (Carro et al., 2010). One such algorithm, the Algorithm for the Reconstruction of Accurate Cellular Networks (ARACNe) (Margolin et al., 2006), uses gene interaction networks constructed from transcriptomic datasets to identify 'hubs', usually transcription factors, which are predicted to directly regulate multiple genes in the signature.

It is an object of the present invention to overcome at least one of the above-mentioned problems.

SUMMARY OF THE INVENTION

Predicting the risk of tumour recurrence, and thus the need for adjuvant therapy, for lymph node negative breast cancer patients (and early stage, node positive breast cancer) can be a significant problem for clinicians and patients. A 'core proliferation signature' has been identified herein which is consistently high in proliferating primary cultures, and is downregulated during cellular senescence. This gene signature is also highly expressed in aggressive breast cancers. A hierarchy of several Master Transcriptional Regulators (MTRs—transcription factors responsible for the regulation of this core set of genes) upstream of these core proliferation genes has been identified. Further analysis of the expression of these factors in breast cancer datasets at the mRNA and protein levels reveals a remarkable ability to predict recurrence risk for early-stage breast cancer. Strikingly, combining two of these factors outperforms the currently used clinical biomarkers for breast cancer recurrence risk, as well as recently developed multi-gene prognostic assays such as Oncotype Dx®. The addition of the senescence regulator p16$^{INK4A}$ to the prognostic panel of proliferative factors allows the identification of tumours with a disrupted cellular senescence pathway, further improving the prognostic power of the invention. Furthermore, unbiased survival analysis of several breast cancer datasets has revealed genes involved in alternative breast cancer-associated pathways such as apoptosis-resistance, invasion and immune response, which can be combined with the MTR panel to increase the prognostic power even further. This approach devised by the Applicant has succeeded in identifying 'drivers' of cancer proliferation which, when combined with additional biomarkers, has the potential to become a superior prognostic assay for early-stage cancer. Thus, by identifying the upstream 'drivers' or regulators of key signatures, more accurate and reliable predictors of breast cancer prognosis can be identified. The Applicant has called this 'core proliferation signature' OncoMasTR, and this name will be used herein.

According to the invention, there is provided a method for predicting risk of recurrence of cancer in an individual with cancer, the method comprising a step of assaying a cancer sample from the individual for positive expression of at least two genes (or proteins encoded by those genes) selected from the group consisting of FOXM1, UHRF1, PTTG1, E2F1, MYBL2, HMGB2, ATAD2, E2F8, ZNF367 and TCF19, wherein positive expression of at least two genes, or proteins encoded by said genes, correlates with increased risk of recurrence of cancer compared with an individual with cancer who does not exhibit positive expression of the same genes.

According to the invention, there is provided a method of predicting risk of recurrence of cancer in an individual with cancer following treatment with CDK4/6 inhibitors, the method comprising a step of assaying a cancer sample from the individual for positive expression of at least two genes, or proteins encoded by said genes, selected from the group consisting of FOXM1, UHRF1, PTTG1, E2F1, MYBL2, HMGB2, ATAD2, E2F8, ZNF367 and TCF19, wherein positive expression of the at least two genes, or proteins encoded by said genes, correlates with increased risk of recurrence of cancer in an individual with cancer following treatment with CDK4/6 inhibitors compared with an individual with cancer who does not exhibit positive expression of the at least two genes or proteins encoded by those genes.

According to the invention, there is provided a method of determining a 5-year survival rate or a 10-year survival rate of an individual diagnosed with breast cancer, the method comprising a step of assaying a cancer tumour sample from the individual for positive expression of at least two genes, or proteins encoded by those genes, selected from FOXM1, UHRF1, PTTG1, E2F1, MYBL2, HMGB2, ATAD2, E2F8, ZNF367 and TCF19, wherein positive expression of the at least two genes, or proteins encoded by those genes, correlates with decreased chance of 5-year survival rate or a 10-year survival rate compared with an individual with cancer who does not exhibit positive expression of the at least two genes or proteins encoded by those genes.

In one embodiment, the method further comprises the step of assaying for the expression of the p16$^{INK4A}$ gene or protein in addition to the at least two genes (or proteins) selected from the group consisting of FOXM1, UHRF1, PTTG1, E2F1, MYBL2, HMGB2, ATAD2, E2F8, ZNF367 and TCF19, wherein dysregulated expression of p16$^{INK4A}$ in combination with positive expression of the at least two genes (or proteins encoded by those genes) selected from the group consisting of FOXM1, UHRF1, PTTG1, E2F1, MYBL2, HMGB2, ATAD2, E2F8, ZNF367 and TCF19, correlates with increased risk of recurrence of cancer, or a decreased chance of a 5-year survival rate or a 10-year survival rate, compared with an individual with cancer who does not exhibit dysregulated expression of p16$^{INK4A}$ and positive expression of the at least two genes (or proteins encoded by those genes). Breast cancer patients with dysregulated expression of p16$^{INK4A}$ and positive expression of the at least two genes (or proteins encoded by those genes) have an increased risk of recurrence of cancer, or a decreased chance of a 5-year survival rate or a 10-year survival rate, compared with patients with cancer that do not exhibit the expression pattern of this combination of genes (or proteins encoded by those genes).

In one embodiment, the at least two genes selected are FOXM1 and UHRF1. In one embodiment, the at least two genes selected are FOXM1 and PTTG1. In one embodiment, the at least two genes selected are FOXM1 and E2F1. In one embodiment, the at least two genes selected are FOXM1 and MYBL2. In one embodiment, the at least two genes selected are FOXM1 and HMGB2. In one embodiment, the at least two genes selected are UHRF1 and PTTG1. In one embodiment, the at least two genes selected are UHRF1 and E2F1. In one embodiment, the at least two genes selected are UHRF1 and MYBL2. In one embodiment, the at least two genes selected are UHRF1 and HMGB2. In one embodiment, the at least two genes selected are PTTG1 and E2F1. In one embodiment, the at least two genes selected are PTTG1 and MYBL2. In one embodiment, the at least two genes selected are PTTG1 and HMGB2. In one embodiment, the at least two genes selected are E2F1 and MYBL2. In one embodiment, the at least two genes selected are E2F1 and HMGB2. In one embodiment, the at least two genes selected are MYBL2 and HMGB2. In one embodiment, the at least two genes selected are FOXM1 and ATAD2. In one embodiment, the at least two genes selected are FOXM1 and E2F8. In one embodiment, the at least two genes selected are FOXM1 and ZNF367. In one embodiment, the at least two genes selected are FOXM1 and TCF19. In one embodiment, the at least two genes selected are UHRF1 and ATAD2. In one embodiment, the at least two genes selected are UHRF1 and E2F8. In one embodiment, the at least two genes selected are UHRF1 and ZNF367. In one embodiment, the at least two genes selected are UHRF1 and TCF19. In one embodiment, the at least two genes selected are PTTG1 and ATAD2. In one embodiment, the at least two genes selected are PTTG1 and E2F8. In one embodiment, the at least two genes selected are PTTG1 and ZNF367. In one embodiment, the at least two genes selected are PTTG1 and TCF19. In one embodiment, the at least two genes selected are E2F1 and ATAD2. In one embodiment, the at least two genes selected are E2F1 and E2F8. In one embodiment, the at least two genes selected are E2F1 and ZNF367. In one embodiment, the at least two genes selected are E2F1 and TCF19. In one embodiment, the at least two genes selected are MYBL2 and ATAD2. In one embodiment, the at least two genes selected are MYBL2 and E2F8. In one embodiment, the at least two genes selected are MYBL2 and ZNF367. In one embodiment, the at least two genes selected are MYBL2 and TCF19. In one embodiment, the at least two genes selected are HMGB2 and ATAD2. In one embodiment, the at least two genes selected are HMGB2 and E2F8. In one embodiment, the at least two genes selected are HMGB2 and ZNF367. In one embodiment, the at least two genes selected are HMGB2 and TCF19. In one embodiment, the at least two genes selected are E2F8 and ATAD2. In one embodiment, the at least two genes selected are E2F8 and TCF19. In one embodiment, the at least two genes selected are E2F8 and ZNF367. In one embodiment, the at least two genes selected are ZNF367 and ATAD2. In one embodiment, the at least two genes selected are ZNF367 and TCF19. In one embodiment, the at least two genes selected are TCF19 and ATAD2. Preferably, the at least two genes selected above are combined with p16$^{INK4A}$.

In one embodiment, at least three genes are selected and the genes selected are FOXM1, UHRF1 and PTTG1. In one embodiment, the genes selected are FOXM1, UHRF1 and E2F1. In one embodiment, the genes selected are FOXM1, UHRF1 and MYBL2. In one embodiment, the genes selected are FOXM1, UHRF1 and HMGB2. In one embodiment, the genes selected are FOXM1, PTTG1 and E2F1. In one embodiment, the genes selected are FOXM1, PTTG1 and MYBL2. In one embodiment, the genes selected are FOXM1, PTTG1 and HMGB2. In one embodiment, the genes selected are FOXM1, E2F1 and MYBL2. In one embodiment, the genes selected are FOXM1, E2F1 and HMGB2. In one embodiment, the genes selected are FOXM1, MYBL2 and HMGB2. In one embodiment, the genes selected are UHRF1, PTTG1 and E2F1. In one embodiment, the genes selected are UHRF1, PTTG1 and MYBL2. In one embodiment, the genes selected are UHRF1, PTTG1 and HMGB2. In one embodiment, the genes selected are PTTG1, E2F1 and MYBL2. In one embodiment, the genes selected are PTTG1, E2F1 and HMGB2. In one embodiment, the genes selected are E2F1, MYBL2 and HMGB2. In one embodiment, the genes selected are FOXM1, UHRF1 and ATAD2. In one embodiment, the genes selected are FOXM1, UHRF1 and E2F8. In one embodiment, the genes selected are FOXM1, UHRF1 and ZNF67. In one embodiment, the genes selected are FOXM1, UHRF1 and TCF19. In one embodiment, the genes selected are FOXM1, PTTG1 and ATAD2. In one embodiment, the genes selected are FOXM1, PTTG1 and E2F8. In one embodiment, the genes selected are FOXM1, PTTG1 and ZNF367. In one embodiment, the genes selected are FOXM1, PTTG1 and TCF19. In one embodiment, the genes selected are FOXM1, E2F1 and ATAD2. In one embodiment, the genes selected are FOXM1, E2F1 and E2F8. In one embodiment, the genes selected are FOXM1, E2F1 and ZNF367. In one embodiment, the genes selected are FOXM1, E2F1 and TCF19. In one embodiment, the genes selected are FOXM1, MYBL2 and ATAD2. In one embodiment, the genes selected are FOXM1, MYBL2 and E2F8. In one embodiment, the genes selected are FOXM1, MYBL2 and ZNF367. In one embodiment, the genes selected are FOXM1, MYBL2 and TCF19. In one embodiment, the genes selected are UHRF1, PTTG1 and ATAD2. In one embodiment, the genes selected are UHRF1, PTTG1 and E2F8. In one embodiment, the genes selected are UHRF1, PTTG1 and ZNF367. In one embodiment, the genes selected are UHRF1, PTTG1 and TCF19. In one embodiment, the genes selected are PTTG1, E2F1 and ATAD2. In one embodiment, the genes selected are PTTG1, E2F1 and E2F8. In one embodiment, the genes selected are PTTG1, E2F1 and ZNF367. In one embodiment, the genes selected are PTTG1, E2F1 and TCF19. In one embodiment, the genes selected are E2F1, MYBL2 and ATAD2. In one embodiment, the genes selected are E2F1, MYBL2 and E2F8. In one embodiment, the genes selected are E2F1, MYBL2 and ZNF367. In one embodiment, the genes selected are E2F1, MYBL2 and TCF19. In one embodiment, the genes selected are FOXM1, HMGB2 and ATAD2. In one embodiment, the genes selected are FOXM1, HMGB2 and E2F8. In one embodiment, the genes selected are FOXM1, HMGB2 and ZNF67. In one embodiment, the genes selected are FOXM1, HMGB2 and TCF19. In one embodiment, the genes selected are HMGB2, PTTG1 and ATAD2. In one embodiment, the genes selected are HMGB2, PTTG1 and E2F8. In one embodiment, the genes selected are HMGB2, PTTG1 and ZNF367. In one embodiment, the genes selected are HMGB2, PTTG1 and TCF19. In one embodiment, the genes selected are HMGB2, E2F1 and ATAD2. In one embodiment, the genes selected are HMGB2, E2F1 and E2F8. In one embodiment, the genes selected are HMGB2, E2F1 and ZNF367. In one embodiment, the genes selected are HMGB2, E2F1 and TCF19. In one embodiment, the genes selected are HMGB2, MYBL2 and ATAD2. In one embodiment, the genes selected are HMGB2, MYBL2 and E2F8. In one embodiment, the genes selected are HMGB2, MYBL2 and ZNF367. In one embodiment, the genes selected are HMGB2, MYBL2 and TCF19. In one embodiment, the genes selected are UHRF1, HMGB2 and ATAD2. In one embodiment, the genes selected are UHRF1, HMGB2 and E2F8. In one embodiment, the genes selected are UHRF1, HMGB2 and ZNF367. In one embodiment, the genes selected are UHRF1, HMGB2 and TCF19. In one embodiment, the genes selected are E2F8, ZNF367 and ATAD2. In one embodiment, the genes selected are E2F8, ZNF367 and TCF19. In one embodiment, the genes selected are ATAD2, E2F8 and TCF19. Preferably, the at least three genes selected above are combined with p16$^{INK4A}$.

In one embodiment, at least four genes are selected and the genes selected are FOXM1, UHRF1, PTTG1 and E2F1. In one embodiment, the genes selected are FOXM1, UHRF1, PTTG1 and MYBL2. In one embodiment, the genes selected are FOXM1, UHRF1, PTTG1 and HMGB2. In one embodiment, the genes selected are FOXM1, UHRF1, E2F1 and MYBL2. In one embodiment, the genes selected are FOXM1, UHRF1, E2F1 and HMGB2. In one embodiment, the genes selected are FOXM1, UHRF1, MYBL2 and HMGB2. In one embodiment, the genes selected are FOXM1, PTTG1, E2F1 and MYBL2. In one embodiment, the genes selected are FOXM1, PTTG1, E2F1 and HMGB2. In one embodiment, the genes selected are FOXM1, E2F1, MYBL2 and HMGB2. In one embodiment, the genes selected are UHRF1, PTTG1, E2F1 and MYBL2. In one embodiment, the genes selected are UHRF1, PTTG1, E2F1 and HMGB2. In one embodiment, the genes selected are PTTG1, E2F1, MYBL2 and HMGB2. In one embodiment, the genes selected are FOXM1, UHRF1, PTTG1 and ATAD2. In one embodiment, the genes selected are FOXM1, UHRF1, PTTG1 and E2F8. In one embodiment, the genes selected are FOXM1, UHRF1, PTTG1 and ZNF367. In one embodiment, the genes selected are FOXM1, UHRF1, PTTG1 and TCF19. In one embodiment, the genes selected are FOXM1, UHRF1, E2F1 and ATAD2. In one embodiment, the genes selected are FOXM1, UHRF1, E2F1 and E2F8. In one embodiment, the genes selected are FOXM1, UHRF1, E2F1 and ZNF367. In one embodiment, the genes selected are FOXM1, UHRF1, E2F1 and TCF19. In one embodiment, the genes selected are FOXM1, UHRF1, MYBL2 and ATAD2. In one embodiment, the genes selected are FOXM1, UHRF1, MYBL2 and E2F8. In one embodiment, the genes selected are FOXM1, UHRF1, MYBL2 and ZNF367. In one embodiment, the genes selected are FOXM1, UHRF1, MYBL2 and TCD1. In one embodiment, the genes selected are FOXM1, UHRF1, HMGB2 and ATAD2. In one embodiment, the genes selected are FOXM1, UHRF1, HMGB2 and E2F8. In one embodiment, the genes selected are FOXM1, UHRF1, HMGB2 and ZNF37. In one embodiment, the genes selected are FOXM1, UHRF1, HMGB2 and TCF19. In one embodiment, the genes selected are FOXM1, PTTG1, E2F1 and ATAD2. In one embodiment, the genes selected are FOXM1, PTTG1, E2F1 and E2F8. In one embodiment, the genes selected are FOXM1, PTTG1, E2F1 and ZNF367. In one embodiment, the genes selected are FOXM1, PTTG1, E2F1 and TCF19. In one embodiment, the genes selected are FOXM1, PTTG1, MYBL2 and ATAD2. In one embodiment, the genes selected are FOXM1, PTTG1, MYBL2 and E2F8. In one embodiment, the genes selected are FOXM1, PTTG1, MYBL2 and ZNF367. In one embodiment, the genes selected are FOXM1, PTTG1, MYBL2 and TCF19. In one embodiment, the genes selected are FOXM1, PTTG1, HMGB2 and ATAD2. In one embodiment, the genes selected are FOXM1, PTTG1, HMGB2 and E2F8. In one embodiment, the genes selected are FOXM1, PTTG1, HMGB2 and ZNF367. In one embodiment, the genes selected are FOXM1, PTTG1, HMGB2 and TCF19. In one embodiment, the genes selected are FOXM1, E2F1, MYBL2 and ATAD2. In one embodiment, the genes selected are FOXM1, E2F1, MYBL2 and E2F8. In one embodiment, the genes selected are FOXM1, E2F1, MYBL2 and ZNF367. In one embodiment, the genes selected are FOXM1, E2F1, MYBL2 and TCF19. In one embodiment, the genes selected are FOXM1, E2F1, HMGB2 and ATAD2. In one embodiment, the genes selected are FOXM1, E2F1, HMGB2 and E2F8. In one embodiment, the genes selected are FOXM1, E2F1, HMGB2 and ZNF367. In one embodiment, the genes selected are FOXM1, E2F1, HMGB2 and TCF19. In one embodiment, the genes selected are FOXM1, MYBL2, HMGB2 and ATAD2. In one embodiment, the genes selected are FOXM1, MYBL2, HMGB2 and E2F8. In one embodiment, the genes selected are FOXM1, MYBL2, HMGB2 and ZNF367. In one embodiment, the genes selected are FOXM1, MYBL2, HMGB2 and TCF19. In one embodiment, the genes selected are UHRF1, PTTG1, E2F1 and ATAD2. In one embodiment, the genes selected are UHRF1, PTTG1, E2F1 and E2F8. In one embodiment, the genes selected are UHRF1, PTTG1, E2F1 and ZNF367. In one embodiment, the genes selected are UHRF1, PTTG1, E2F1 and TCF19. In one embodiment, the genes selected are UHRF1, PTTG1, MYBL2 and ATAD2. In one embodiment, the genes selected are UHRF1, PTTG1, MYBL2 and E2F8. In one embodiment, the genes selected are UHRF1, PTTG1, MYBL2 and ZNF36. In one embodiment, the genes selected are UHRF1, PTTG1, MYBL2 and TCF19. In one embodiment, the genes selected are UHRF1, PTTG1, HMGB2 and ATAD2. In one embodiment, the genes selected are UHRF1, PTTG1, HMGB2 and E2F8. In one embodiment, the genes selected are UHRF1, PTTG1, HMGB2 and ZNF367. In one embodiment, the genes selected are UHRF1, PTTG1, HMGB2 and TCF19. In one embodiment, the genes selected are PTTG1, E2F1, MYBL2 and ATAD2. In one embodiment, the genes selected are PTTG1, E2F1, MYBL2 and E2F8. In one embodiment, the genes selected are PTTG1, E2F1, MYBL2 and ZNF367. In one embodiment, the genes selected are PTTG1, E2F1, MYBL2 and TCF19. In one embodiment, the genes selected are PTTG1, E2F1, HMGB2 and ATAD2. In one embodiment, the genes selected are PTTG1, E2F1, HMGB2 and E2F8. In one embodiment, the genes selected are PTTG1, E2F1, HMGB2 and ZNF367. In one embodiment, the genes selected are PTTG1, E2F1, HMGB2 and TCF19. In one embodiment, the genes selected are E2F1, MYBL2, HMGB2 and ATAD2. In one embodiment, the genes selected are E2F1, MYBL2, HMGB2 and E2F8. In one embodiment, the genes selected are E2F1, MYBL2, HMGB2 and ZNF367. In one embodiment, the genes selected are E2F1, MYBL2, HMGB2 and TCF19. In one embodiment, the genes selected are ATAD2, EDF8, ZNF367 and TCF19. Preferably, the at least four genes selected above are combined with $p16^{INK4A}$.

In one embodiment, at least five genes are selected and the genes selected are FOXM1, UHRF1, PTTG1, E2F1 and MYBL2. In one embodiment, the genes selected are FOXM1, UHRF1, PTTG1, E2F1 and HMGB2. In one embodiment, the genes selected are FOXM1, PTTG1, E2F1, MYBL2 and HMGB2. In one embodiment, the genes selected are UHRF1, PTTG1, E2F1, MYBL2 and HMGB2. In one embodiment, the genes selected are FOXM1, UHRF1, PTTG1, E2F1 and ATAD2. In one embodiment, the genes selected are FOXM1, UHRF1, PTTG1, E2F1 and E2F8. In one embodiment, the genes selected are FOXM1, UHRF1, PTTG1, E2F1 and ZNF367. In one embodiment, the genes selected are FOXM1, UHRF1, PTTG1, E2F1 and TCF19. In one embodiment, the genes selected are FOXM1, UHRF1, PTTG1, MYBL2 and ATAD2. In one embodiment, the genes selected are FOXM1, UHRF1, PTTG1, MYBL2 and EFF8. In one embodiment, the genes selected are FOXM1, UHRF1, PTTG1, MYBL2 and ZNF367. In one embodiment, the genes selected are FOXM1, UHRF1, PTTG1, MYBL2 and TCF19. In one embodiment, the genes selected are FOXM1, UHRF1, PTTG1, HMGB2 and ATAD2. In one embodiment, the genes selected are FOXM1, UHRF1, PTTG1, HMGB2 and E2F8. In one embodiment, the genes selected are FOXM1, UHRF1, PTTG1, HMGB2 and ZNF367. In one embodiment, the genes selected are FOXM1, UHRF1, PTTG1, HMGB2 and TCF19. In one embodiment, the genes selected are UHRF1, PTTG1, E2F1, MYBL2 and ATAD2. In one embodiment, the genes selected are UHRF1, PTTG1, E2F1, MYBL2 and E2F8. In one embodiment, the genes selected are UHRF1, PTTG1, E2F1, MYBL2 and ZNF367. In one embodiment, the genes selected are UHRF1, PTTG1, E2F1, MYBL2 and TCF19. In one embodiment, the genes selected are UHRF1, PTTG1, E2F1, HMBG2 and ATAD2. In one embodiment, the genes selected are UHRF1, PTTG1, E2F1, HMBG2 and E2F8. In one embodiment, the genes selected are UHRF1, PTTG1, E2F1, HMBG2 and ZNF367. In one embodiment, the genes selected are UHRF1, PTTG1, E2F1, HMBG2 and TCF19. In one embodiment, the genes selected are PTTG1, E2F1, MYBL2, HMGB2 and ATAD2. In one embodiment, the genes selected are PTTG1, E2F1, MYBL2, HMGB2 and E2F8. In one embodiment, the genes selected are PTTG1, E2F1, MYBL2, HMGB2 and ZNF367. In one embodiment, the genes selected are PTTG1, E2F1, MYBL2, HMGB2 and TCF19. In one embodiment, the genes selected are ATAD2, E2F8, ZNF367, TCF19 and FOXM1. In one embodiment, the genes selected are ATAD2, E2F8, ZNF367, TCF19 and UHRF1. In one embodiment, the genes selected are ATAD2, E2F8, ZNF367, TCF19 and PTTG1. In one embodiment, the genes selected are ATAD2, E2F8, ZNF367, TCF19 and E2F1. In one embodiment, the genes selected are ATAD2, E2F8, ZNF367, TCF19 and MYBL2. In one embodiment, the genes selected are ATAD2, E2F8, ZNF367, TCF19 and HMGB2. Preferably, the at least five genes selected above are combined with $p16^{INK4A}$.

In one embodiment, the at least two genes comprise FOXM1, and at least one further gene selected from UHRF1, PTTG1, E2F1, MYBL2, HMGB2, ATAD2, E2F8, ZNF367 and TCF19. Preferably, the at least two genes is further combined with $p16^{INK4A}$.

In one embodiment, the at least two genes comprise UHRF1, and at least one further gene selected from FOXM1, PTTG1, E2F1, MYBL2, HMGB2, ATAD2, E2F8, ZNF367 and TCF19. Preferably, the at least two genes is further combined with p16$^{INK4A}$.

In one embodiment, the at least two genes comprise PTTG1, and at least one further gene selected from FOXM1, UHRF1, E2F1, MYBL2, HMGB2, ATAD2, E2F8, ZNF367 and TCF19. Preferably, the at least two genes is further combined with p16$^{INK4A}$.

In one embodiment, the at least two genes comprise E2F1, and at least one further gene selected from FOXM1, PTTG1, UHRF1, MYBL2, HMGB2, ATAD2, E2F8, ZNF367 and TCF19. Preferably, the at least two genes is further combined with p16$^{INK4A}$.

In one embodiment, the at least two genes comprise MYBL2, and at least one further gene selected from FOXM1, PTTG1, E2F1, UHRF1, HMGB2, ATAD2, E2F8, ZNF367 and TCF19. Preferably, the at least two genes is further combined with p16$^{INK4A}$.

In one embodiment, the at least two genes comprise HMGB2, and at least one further gene selected from FOXM1, PTTG1, E2F1, MYBL2, UHRF1, ATAD2, E2F8, ZNF367 and TCF19. Preferably, the at least two genes is further combined with p16$^{INK4A}$.

In one embodiment, the genes selected are FOXM1, UHRF1, PTTG1, E2F1, MYBL2 and HMGB2. Preferably, the genes selected are further combined with p16$^{INK4A}$.

In one embodiment, the genes selected are FOXM1, UHRF1, PTTG1, E2F1, MYBL2, HMGB2, and one or more or all of ATAD2, E2F8, ZNF367 and TCF19. Preferably, the genes selected are further combined with p16$^{INK4A}$.

In one embodiment, the genes selected consist essentially of FOXM1, UHRF1, PTTG1, E2F1, MYBL2, and HMGB2. Preferably, the genes are further combined with p16$^{INK4A}$. The term "consist essentially of" should be understood to mean all six genes, or five genes, or four genes, or three genes, or two genes selected from FOXM1, UHRF1, PTTG1, E2F1, MYBL2, and HMGB2.

In one embodiment, the cancer is selected from the group comprising node-negative, ER-positive breast cancer; early stage, node positive breast cancer; multiple myeloma, prostate cancer, glioblastoma, lymphoma, fibrosarcoma; myxosarcoma; liposarcoma; chondrosarcoma; osteogenic sarcoma; chordoma; angiosarcoma; endotheliosarcoma; lymphangiosarcoma; lymphangioendotheliosarcoma; synovioma; mesothelioma; Ewing's tumour; leiomyosarcoma; rhabdomyosarcoma; colon carcinoma; pancreatic cancer; breast cancer; ovarian cancer; squamous cell carcinoma; basal cell carcinoma; adenocarcinoma; sweat gland carcinoma; sebaceous gland carcinoma; papillary carcinoma; papillary adenocarcinomas; cystadenocarcinoma; medullary carcinoma; bronchogenic carcinoma; renal cell carcinoma; hepatoma; bile duct carcinoma; choriocarcinoma; seminoma; embryonal carcinoma; Wilms' tumour; cervical cancer; uterine cancer; testicular tumour; lung carcinoma; small cell lung carcinoma; bladder carcinoma; epithelial carcinoma; glioma; astrocytoma; medulloblastoma; craniopharyngioma; ependymoma; pinealoma; hemangioblastoma; acoustic neuroma; oligodendroglioma; meningioma; melanoma; retinoblastoma; and leukemias. Suitably, the cancer is an epithelial cancer.

In one embodiment, the cancer is preferably breast cancer or prostate cancer. Ideally, the breast cancer is early stage, typically node-negative breast cancer or early stage, node positive breast cancer. Ideally, the breast cancer is early stage, node-negative or early stage, node positive, ER-positive breast cancer.

In one embodiment, the recurrence is development of a secondary tumour.

In one embodiment, the recurrence is developing a further, independent primary cancer unrelated to the sampled cancer.

In one embodiment of the invention, there is provided a method of predicting the risk of recurrence of breast cancer in an early stage, node-negative breast cancer patient, or an early stage, node positive breast cancer patient, the method comprising a step of assaying a cancer tumour sample from the breast cancer patient for positive expression of at least two genes (or proteins encoded by those genes) selected from the group consisting of FOXM1, UHRF1, PTTG1, E2F1, MYBL2, HMGB2, ATAD2, E2F8, ZNF367, and TCF19, wherein positive expression of the at least two genes (or proteins encoded by those genes) correlates with increased risk of recurrence of cancer compared with an individual with cancer who does not exhibit positive expression of the at least two genes (or proteins encoded by those genes).

In one embodiment, the method further comprises the step of assaying for the expression of the p16$^{INK4A}$ gene (or a protein encoded by said gene) in addition to the at least two genes (or proteins encoded by those genes) selected from the group consisting of FOXM1, UHRF1, PTTG1, E2F1, MYBL2, HMGB2, ATAD2, E2F8, ZNF367 and TCF19, wherein dysregulated expression of p16$^{INK4A}$ in combination with positive expression of a combination of the at least two of genes (or proteins encoded by those genes), correlates with increased risk of recurrence of cancer compared with an individual with cancer who does not exhibit dysregulated expression of p16$^{INK4A}$ and positive expression of the at least two genes (or proteins encoded by those genes). Breast cancer patients with dysregulated p16$^{INK4A}$ and positive expression of the at least two genes (or proteins encoded by those genes) have an increased risk of recurrence of cancer compared with individuals with cancer that do not exhibit the combination of positive expression of the at last two genes and dysregulated expression of p16$^{INK4A}$.

In one embodiment of the invention, there is provided a method of identifying a cancer patient that is suitable for treatment with a therapy for preventing recurrence or progression of the cancer, the method comprising a step of assaying a cancer sample from the cancer patient for positive expression of at least two genes (or proteins encoded by those genes) selected from the group consisting of FOXM1, UHRF1, PTTG1, E2F1, MYBL2, HMGB2, ATAD2, E2F8, ZNF367 and TCF19, wherein positive expression of the at least two genes (or proteins encoded by those genes) compared with an individual with cancer who does not exhibit positive expression of the at least two genes (or proteins encoded by those genes), is indicative that the cancer patient is suitable for treatment with a therapy for preventing recurrence or progression of the cancer.

In one embodiment, the therapy is a neoadjuvant therapy. In the specification, the term "neoadjuvant therapy" should be understood to mean treatment given before primary treatment to increase the chances of long-term survival. Primary treatment is generally surgery. Neoadjuvant therapy are generally selected from chemotherapy, hormonal therapy, targeted therapy, radiation therapy, immunotherapy or a combination thereof.

In one embodiment, the therapy is an adjuvant therapy. In the specification, the term "adjuvant therapy" should be understood to mean any treatment given after primary treatment to increase the chances of long-term survival. Primary treatment is generally surgery. Adjuvant therapy are generally selected from chemotherapy, hormonal therapy, targeted therapy, radiation therapy, immunotherapy or a combination thereof.

In one embodiment, the therapy can be a combination of neoadjuvant and adjuvant therapy. It should be understood that in the specification, the "neoadjuvant" and "adjuvant" therapies can be used interchangeably.

In one embodiment, the method further comprises the step of assaying for the expression of the $p16^{INK4A}$ gene (or a protein encoded by said gene) in addition to the at least two genes (or proteins encoded by those genes) selected from the group consisting of FOXM1, UHRF1, PTTG1, E2F1, MYBL2, HMGB2, ATAD2, E2F8, ZNF367 and TCF19, wherein dysregulated expression of $p16^{INK4A}$ in combination with positive expression of a combination of at least two of the genes (or proteins encoded by those genes), when compared with an individual with cancer who does not exhibit dysregulated expression of $p16^{INK4A}$ and positive expression of the at least two genes, is indicative that the cancer patient is suitable for treatment with an adjuvant therapy for preventing recurrence or progression of the cancer. Breast cancer patients with dysregulated $p16^{INK4A}$ expression and positive expression of the at least two genes (or proteins encoded by those genes) may be suitable for treatment with an adjuvant therapy for preventing recurrence or progression of the cancer.

In one embodiment, the cancer patient may be suitable for treatment with a neoadjuvant therapy for preventing recurrence or progression of the cancer.

In one embodiment, the cancer is early stage, node-negative breast cancer or early stage, node positive breast cancer. Ideally, breast cancer is early stage, node-negative, ER-positive breast cancer or early stage, node positive, ER-positive breast cancer.

In one embodiment, the adjuvant therapy and neoadjuvant therapy is chemotherapeutic therapy. In one embodiment, the adjuvant therapy and neoadjuvant therapy is a CDK4/6 inhibitor therapy such as palbociclib therapy (PD 0332991, Pfizer), Abemaciclib (LY2835219; Lilly, USA), or LEE011 (Novartis, Switzerland).

In one embodiment of the invention, there is provided a system for obtaining data from at least one test sample obtained from at least one individual, the system comprising:
  a determination module configured to receive at least one test sample and perform at least one test analysis on the test sample to assay for expression of at least two genes (or proteins encoded by those genes) selected from the group consisting of FOXM1, UHRF1, PTTG1, E2F1, MYBL2, HMGB2, ATAD2, E2F8, ZNF367 and TCF19;
  optionally, a storage system for storing expression data generated by the determination module; and
  a display module for displaying a content based in part on the data output from said determination module, wherein the content comprises a signal indicative of the expression of the at least two genes.

In one embodiment, the determination module is further configured to perform at least one test analysis on the test sample for dysregulation of $p16^{INK4A}$ in combination with the test analysis on the at least two genes (or proteins encoded by those genes).

In one embodiment, the system comprises a correlation module for correlating the expression data of the at least two genes (or proteins encoded by those genes) from the determination module with recurrence potential of cancer, wherein the expression data of each gene (or a protein encoded by the gene) is compared with a reference value for the gene (or a protein encoded by the gene) to determine positive expression of the gene (or a protein encoded by the gene), and wherein positive expression of the at least two genes (or proteins encoded by those genes) correlates with increased potential for recurrence compared with an individual with cancer who does not exhibit positive expression of the at least two genes (or proteins encoded by those genes), and wherein the display module displays a content based in part on the data from the correlation system, the content optionally comprising a signal indicative of the recurrence potential of the cancer.

In one embodiment, the correlation module further correlates the expression data of the at least two genes (or proteins encoded by those genes) from the determination module with recurrence potential of cancer, together with the expression data of $p16^{INK4A}$, wherein the expression data of each gene (or a protein encoded by the gene) and $p16^{INK4A}$ is compared with a reference value for each gene (or a protein encoded by the gene) and $p16^{INK4A}$, respectively, to determine positive expression of the gene (or a protein encoded by the gene) and dysregulation of $p16^{INK4A}$, and wherein positive expression of the at least two genes (or proteins encoded by those genes) and dysregulation of $p16^{INK4A}$ correlates with increased potential for recurrence compared with an individual with cancer who does not exhibit positive expression of the at least two genes (or proteins encoded by those genes) and dysregulation of $p16^{INK4A}$, and wherein the display module displays a content based in part on the data from the correlation system, the content optionally comprising a signal indicative of the recurrence potential of the cancer.

Suitably, the determination system may be selected from an immunohistochemical detection apparatus, a Western Blot, a Northern Blot, a Southern Blot, quantitative polymerase chain reaction (PCR), reverse transcriptase PCR (RT-PCR), quantitative real time RT-PCR (qRT-PCR), an enzyme-linked immunosorbent assay (ELISA), protein determination on polyacrylamide gels, and such methods known to those skilled in the art. Ideally, the determination system comprises an immunohistochemical detection apparatus.

In one embodiment of the invention, the content based on the comparison result or the determination system is displayed on a computer monitor. In one embodiment of the invention, the content based on the comparison result or determination system is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

In one embodiment of the invention, there is provided a method for monitoring the effectiveness of treatment of cancer in an individual with cancer, the method comprising a step of assaying a cancer sample from the individual with cancer for expression of at least two genes selected from the group consisting of FOXM1, UHRF1, PTTG1, E2F1, MYBL2, HMGB2, ATAD2, E2F8, ZNF367 and TCF19, wherein higher expression of at least two genes selected from the group consisting of FOXM1, UHRF1, PTTG1, E2F1, MYBL2, HMGB2, ATAD2, E2F8, ZNF367 and TCF19 correlates with ineffective treatment and poor outcome compared with an individual with cancer who has lower expression of the at least two genes.

In one embodiment, the method further comprises the step of assaying the cancer sample for expression of the $p16^{INK4A}$ gene (or a protein encoded by said gene) in combination with assaying the at least two genes (or proteins encoded by said genes), whereby dysregulated expression of $p16^{INK4A}$ correlates with ineffective treatment and poor outcome compared with an individual with cancer who has moderate expression of $p16^{INK4A}$.

In one embodiment of the invention, there is provided a method for treating cancer comprising the steps of:
identifying an individual with increased potential for recurrence of cancer by assaying a cancer sample from the individual for expression of at least two genes selected from the group consisting of FOXM1, UHRF1, PTTG1, E2F1, MYBL2, HMGB2, ATAD2, E2F8, ZNF367 and TCF19, wherein higher expression of at least two genes selected from the group consisting of FOXM1, UHRF1, PTTG1, E2F1, MYBL2, HMGB2, ATAD2, E2F8, ZNF367 and TCF19 correlates with increased potential for recurrence of cancer compared with an individual with cancer who has lower expression of the at least two genes; and
treating the individual with a therapeutically effective amount of an adjuvant therapy.

In one embodiment, the individual is treated with a therapeutically effective amount of a neoadjuvant therapy.

In one embodiment of the invention, there is provided a method for treating cancer comprising the steps of:
identifying an individual with increased potential for recurrence of cancer by assaying a cancer sample from the individual for expression of at least two genes selected from the group consisting of FOXM1, UHRF1, PTTG1, E2F1, MYBL2, HMGB2, ATAD2, E2F8, ZNF367 and TCF19, wherein higher expression of at least two genes selected from the group consisting of FOXM1, UHRF1, PTTG1, E2F1, MYBL2, HMGB2, ATAD2, E2F8, ZNF367 and TCF19 correlates with increased potential for recurrence of cancer compared with an individual with cancer who has lower expression of the at least two genes; and
treating the individual with a therapeutically effective amount of a neoadjuvant therapy.

In one embodiment, the individual is treated with a therapeutically effective amount of an adjuvant therapy.

In one embodiment, the method further comprises the step of assaying the cancer sample for expression of the $p16^{INK4A}$ gene (or a protein encoded by said gene) in combination with assaying the at least two genes (or proteins encoded by said genes), whereby dysregulated expression of $p16^{INK4A}$ correlates with potential for recurrence of cancer when compared with an individual with cancer who has moderate expression of $p16^{INK4}$.

In one embodiment, the neoadjuvant therapy and adjuvant therapy is an agent selected from, but not limited to, trastuzumab (Herceptin®), lapatinib (Tykerb®), neratinib, afatinib (Tovok®), pertuzumab, CDK4/6 inhibitors (such as palbociclib (PD 0332991, Pfizer), Abemaciclib (LY2835219; Lilly, USA), and LEE011 (Novartis, Switzerland)), cyclophosphamide, methotrexate, 5-fluorouracil, gemcitabine, adriamycin (doxorubicin), epirubucin, docetaxel (Taxotere®), paclitaxel (Taxol®), capecitabine (Xeloda®), and tamoxifen.

The invention also relates to a method of treating an individual to prevent or inhibit recurrence of the cancer comprising a step of identifying a cancer patient at risk of recurrence using a method of the invention, and then treating the cancer patient with an agent or agents to prevent or inhibit recurrence of the cancer. Typically, the agent or agents comprise adjuvant or neoadjuvant therapy, or a combination of both.

In one embodiment, there is provided a method of predicting risk of recurrence of cancer in an individual with cancer, the method comprising a step of assaying a cancer sample from the individual for positive expression of at least four genes, or proteins encoded by said genes, selected from FOXM1, UHRF1, PTTG1, E2F1, MYBL2, HMGB2, ATAD2, E2F8, ZNF367 and TCF19, wherein positive expression of the at least four genes, or proteins encoded by said genes, correlates with increased risk of recurrence of cancer compared with an individual with cancer who does not exhibit positive expression of the at least four genes or proteins encoded by those genes.

In one embodiment, there is provided a method of predicting risk of recurrence of cancer in an individual with cancer following treatment with CDK4/6 inhibitors, the method comprising a step of assaying a cancer sample from the individual for positive expression of at least four genes, or proteins encoded by said genes, selected from FOXM1, UHRF1, PTTG1, E2F1, MYBL2, HMGB2, ATAD2, E2F8, ZNF367 and TCF19, wherein positive expression of the at least four genes correlates with increased risk of recurrence of cancer in an individual with cancer following treatment with CDK4/6 inhibitors compared with an individual with cancer who does not exhibit positive expression of the at least four genes or proteins encoded by those genes.

In one embodiment, there is provided a method of predicting risk of recurrence of breast cancer in an early stage, node negative breast cancer patient, the method comprising a step of assaying a cancer tumour sample from the patient for positive expression of at least four genes, or proteins encoded by those genes, selected from FOXM1, UHRF1, PTTG1, E2F1, MYBL2, HMGB2, ATAD2, E2F8, ZNF367 and TCF19, wherein positive expression of the at least four genes, or proteins encoded by those genes, correlates with increased risk of recurrence of cancer compared with a patient with cancer who does not exhibit positive expression of the at least four genes or proteins encoded by those genes.

In one embodiment, there is provided method of determining a 5-year survival rate or a 10-year survival rate of an individual diagnosed with breast cancer, the method comprising a step of assaying a cancer tumour sample from the individual for positive expression of at least four genes, or proteins encoded by those genes, selected from FOXM1, UHRF1, PTTG1, E2F1, MYBL2, HMGB2, ATAD2, E2F8, ZNF367 and TCF19, wherein positive expression of the at least four genes, or proteins encoded by those genes, correlates with decreased chance of 5-year survival rate or 10-year survival rate compared with an individual with cancer who does not exhibit positive expression of the at least four genes or proteins encoded by those genes.

In one embodiment, the methods further comprising the step of assaying for the expression of p16$^{INK4A}$ gene or a protein encoded by said gene, wherein dysregulated expression of p16$^{INK4A}$, in combination with positive expression of the at least four genes or proteins encoded by those genes, correlates with increased risk of recurrence of cancer or a decreased chance of 5-year survival rate or 10-year survival rate compared with an individual with cancer who does not exhibit dysregulated expression of p16$^{INK4A}$ and positive expression of the at least four genes or proteins encoded by those genes.

In one embodiment, there is provided a method of identifying a cancer patient that is suitable for treatment with a therapy for preventing recurrence or progression of the cancer, the method comprising a step of assaying a cancer sample from the cancer patient for positive expression of at least four genes selected from FOXM1, UHRF1, PTTG1, E2F1, MYBL2, HMGB2, ATAD2, E2F8, ZNF367 and TCF19, wherein positive expression of the at least four genes or proteins encoded by those genes compared with an individual with cancer who does not exhibit positive expression of the at least two genes or proteins encoded by those genes, is indicative that the cancer patient is suitable for treatment with a therapy for preventing recurrence or progression of the cancer.

In one embodiment, there is provided a system for obtaining data from at least one test sample obtained from at least one individual, the system comprising a determination module configured to receive at least one test sample and perform at least one test analysis on the test sample to assay for expression of at least four genes or proteins encoded by those genes selected from FOXM1, UHRF1, PTTG1, E2F1, MYBL2, HMGB2, ATAD2, E2F8, ZNF367 and TCF19; optionally, a storage system for storing expression data generated by the determination module; and a display module for displaying a content based in part on the data output from said determination module, wherein the content comprises a signal indicative of the expression of at the least two genes or proteins encoded by those genes.

In one embodiment, there is provided a method for monitoring the effectiveness of treatment of cancer in an individual with cancer, the method comprising a step of assaying a cancer sample from the individual with cancer for expression of at least four genes or proteins encoded by said genes selected from FOXM1, UHRF1, PTTG1, E2F1, MYBL2 and HMGB2, wherein higher expression of at least four genes selected from FOXM1, UHRF1, PTTG1, E2F1, MYBL2, HMGB2, ATAD2, E2F8, ZNF367 and TCF19 correlates with ineffective treatment and poor outcome compared with an individual with cancer who has lower expression of the at least four genes or proteins encoded by those genes.

In one embodiment, there is provided a method of predicting risk of recurrence or progression of breast cancer in a patient, and treating the patient with a therapy for preventing recurrence of the cancer, the method comprising a step of assaying a cancer sample from the patient for positive expression of at least four genes selected from FOXM1, UHRF1, PTTG1, E2F1, MYBL2, HMGB2, ATAD2, E2F8, ZNF367 and TCF19, wherein positive expression of the at least four genes, or proteins encoded by those genes, correlates with increased risk of recurrence or progression of cancer compared with a patient with cancer who does not exhibit positive expression of the at least four genes, or proteins encoded by those genes; and administering a neoadjuvant or an adjuvant therapy, or a combination of both, to the patient to prevent recurrence or progression of the cancer.

In one embodiment, the at least four genes, or proteins encoded by said genes, are FOXM1, PTTG1, UHRF1 and HMGB2.

BRIEF DESCRIPTION OF THE DRAWINGS

The invention will be more clearly understood from the following description of an embodiment thereof, given by way of example only, with reference to the accompanying drawings, in which:—

FIG. 1A depicts Western blot analysis of the proliferation marker EZH2 and the cellular senescence marker p16INK4A in growing (low passage) and senescent (high passage) human mammary epithelial cells (HMECs) and mouse embryonic fibroblasts (MEFs). β-actin was used as a loading control. FIG. 1B depicts Duplicate transcriptomic profiling experiments in growing and senescent HMEC and MEF cultures were aligned in order to identify genes expressed at a consistently high level in proliferating cells. Heat-map analysis depicts all genes up- or down-regulated by more than two-fold in HMECs, and the corresponding change in MEFs. (Cluster 1=58 genes; Cluster 2=193 genes; Cluster 3=184 genes; Cluster 4=214 genes). Cluster 4 represents a 'core proliferation' signature comprising the genes most significantly and consistently downregulated during serial passaging of both HMECs and MEFs. FIG. 1C depicts Quantitative real-time PCR validation of gene expression changes of representative genes from each of the gene clusters shown in panel B. The ribosomal RNA gene, RPLPO, was used for normalization of these data. FIG. 1D depicts Gene ontology analysis of individual gene clusters. Red line indicates a p-value of 0.05. FIG. 1E depicts Gene enrichment analysis of clusters 1-4 in the MammaPrint signature and the Genomic Grade signature. The fold change of the observed overlap versus what would be expected by chance is represented on the Y-axis. The number of 'core proliferation' genes (top number) present in each 'poor prognosis' signature (bottom number) is shown.

FIG. 2A depicts Reverse engineering analysis using ARACNe predicts 6 upstream Master Transcriptional Regulators (MTRs) of the 'core proliferation' signature. Shown is a representative ARACNe network of the HMEC/MEF 'core proliferation' signature (Cluster 4) within the NKI dataset (van de Vijver et al., 2002). MTRs are highlighted in red, and cluster 4 genes are highlighted in green. FIG. 2B depicts Validation of MTR binding to genes within the 'core proliferation' signature by ChIP-qRT-PCR. Precipitated DNA was analyzed by qRT-PCR using primers directed towards the promoters of the indicated genes (SEQ ID NOs: 1 to 38). Anti-HA antibody was used as a negative control for ChIP, and the β-ACTB and CHDS promoters were used as negative promoter controls for qRT-PCR. ChIP enrichments are presented as the percentage of protein bound, normalised to input. The error bars indicate standard deviation of three technical replicates. FIG. 2C depicts Heat-map analysis showing ChIP-seq data for FOXM1, MYBL2 and E2F1, in HMEC-Tert cells. Binding at the promoters of genes from Clusters 1-4 is indicated by increasing signal for each factor, FOXM1 MYBL2 and E2F1. The region between −2 and +2 of the transcriptional start site (TSS) of these genes is shown. FIG. 2D depicts Representative ChIP-seq tracks of the indicated genes, with FOXM1, MYBL2 and E2F1 bound at their promoters in HMEC-Tert cells. RNA-seq data from both low and high passage HMECs is also depicted for each gene. The KRT2 gene is included as a negative control.

FIG. 3A demonstrates that Master transcriptional regulators are predicted to be upstream of the 'Genomic Grade' poor prognosis signature. Shown is a representative ARACNe network of the 'Genomic Grade' signature (Sotiriou et al., 2006) within the Loi dataset (Loi et al., 2007). MTRs and Genomic Grade signature genes are highlighted. In FIG. 3B, Kaplan-Meier analyses demonstrate that the combination of the 6 MTRs (upper) exhibit superior prognostic value than Ki67 (lower) in node negative samples without adjuvant chemotherapy in the combined microarray dataset in terms of recurrence-free survival (Loi et al., 2007; Miller et al., 2005; and van de Vijver et al., 2002) (n=457). The MTR combined score and Ki67 gene expression data were split as 2 (Lo/Hi) and 3 (Lo/Med/Hi) groups. FIG. 3C depicts Representative examples of immunohistochemical staining for the indicated factors in low and high-risk tumors on a breast cancer tissue microarray. Low risk tumors were defined as those that did not recur within the study timeframe, whereas high risk tumors did recur. FIG. 3D depicts Kaplan-Meier survival curves for FOXM1, UHRF1, HMGB2 and PTTG1 combined, compared to Ki67 and the St. Gallen criteria in TMA samples (n=408) in terms of recurrence-free survival. FIG. 3E depicts Heat map illustrating the prognostic power of FOXM1, UHRF1, HMGB2 and PTTG1 and the 4 MTRs combined on the breast tumours from the TMA cohort (n=408) in terms of recurrence-free survival. Ki67 staining results and St. Gallen criteria were included for comparison. The scale represents −log 10 of the p-values calculated using log-rank test.

FIG. 4A depicts Correlations of the mRNA expression levels of CDKN2A with gene copy number alterations (CNA) in the RB1 and CDKN2A gene loci using the GISTIC tool on data 457 breast cancers from TCGA (TCGA, 2012, Nature, 490, 61-70). FIG. 4B depicts Kaplan-Meier survival curves for CDKN2A mRNA in node negative breast cancers without adjuvant chemotherapy in the combined microarray dataset (n=457) in terms of recurrence-free survival. Samples were stratified into 3 groups based on CDKN2A mRNA expression levels, cut at the 33rd and 66th percentile. Additionally, the undetected and high expression groups were combined and compared to the moderate expression group. Chi2 values and p-values were calculated using log-rank test. FIG. 4C depicts Representative examples of immunohistochemical staining for p16 on low and high-risk tumors. Low risk tumors were defined as those which did not recur within the study timeframe, whereas high risk tumors did recur. FIG. 4D depicts Kaplan-Meier survival curves for p16 protein levels in the TMA cohort (n=408) measuring recurrence-free survival. Patients were stratified by p16 protein levels into negative, moderate (<50% positive cells) and high expression (>50% positive cells) groups. Chi2 values and p-values were calculated using log-rank test. FIG. 4E depicts Kaplan-Meier survival curves for p16 protein levels in the TMA cohort (n=408) measuring breast cancer-specific survival. Patients were stratified as in FIG. 4C.

FIG. 5A depicts Kaplan-Meier survival curves comparing the prognostic value of the OncoMasTR RNA score (combination of CDKN2A and 6 MTRs) with estimates of the Oncotype Dx (21-gene) and Mammaprint (70-gene) signatures in node negative samples without adjuvant chemotherapy in the combined microarray dataset (n=457) in terms of recurrence-free survival. Both low/moderate/high and low/high splits were used to facilitate comparison to existing prognostic signatures. FIG. 5B depicts Heat maps illustrating the prognostic value of CDKN2A alone, 6 MTRs combined, OncoMasTR RNA score, 70-gene signature, 21-gene signature and Ki67 in node negative samples without adjuvant chemotherapy in three individual breast cancer microarray datasets (Loi et al., 2007; Miller et al., 2005; and van de Vijver et al., 2002) and the combined dataset (n=457) in terms of recurrence-free survival. The 70-gene and 21-gene signature predicted risk groups were estimated based on gene expression data using the genefu package in R. The scale represents −log 10 of the p-values calculated using log-rank test. Both 2 and 3 group splits were used to facilitate comparison to existing prognostic signatures. FIG. 5C depicts Kaplan-Meier survival curves illustrating the combined score of 4 MTRs (FOXM1, UHRF1, HMGB2, PTTG1) and p16 (OncoMasTR IHC score) in all samples (left, n=408) and node negative samples (right, n=222) from the TMA cohort using recurrence-free survival data. The prognostic values of the 4 MTRs alone, p16 alone, the OncoMasTR IHC score, Ki67 and St. Gallen criteria were represented as a heat map based on the −log 10 of p-values calculated using the log-rank test. FIG. 5D depicts Kaplan-Meier survival as in FIG. 5C, using breast cancer specific survival data.

FIG. 6A depicts Kaplan-Meier survival curves comparing the prognostic value of the OncoMasTR RNA score (6 MTRs and CDKN2A) with the 21-gene and 70-gene signatures in ER-positive patients who did not receive adjuvant chemotherapy, in the combined microarray dataset (n=536) in terms of recurrence-free survival. FIG. 6B depicts Kaplan-Meier survival curves as in FIG. 6A. in lymph-node negative, ER-positive patients who did not receive adjuvant chemotherapy, in the combined microarray dataset (n=366).

DETAILED DESCRIPTION OF THE DRAWINGS

Definitions

Figure 1A:
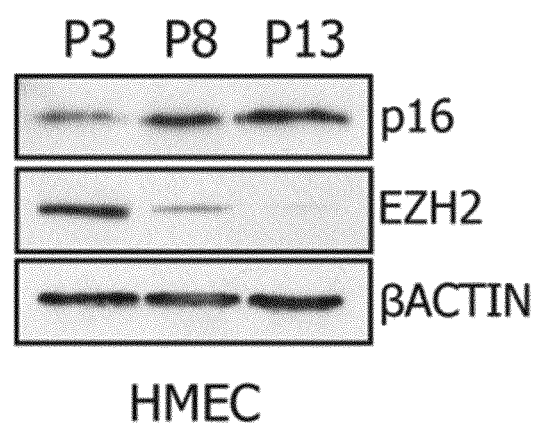
FIGS. 1A-1E illustrate the Identification of master transcriptional regulators (MTRs) of breast cell proliferation.
Figure 1A:
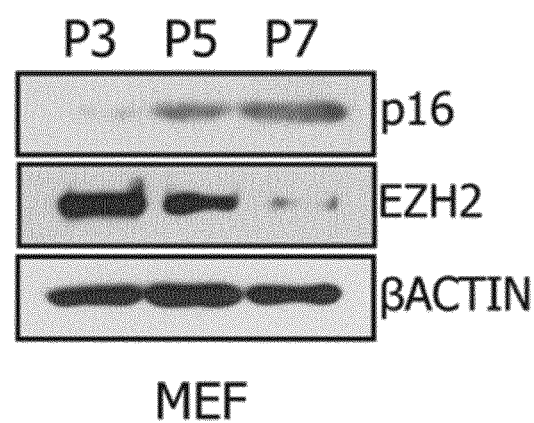

In this specification, the term "cancer sample" should be understood to mean tumour cells, tumour tissue, or other biological material derived from a tumour, for example conditioned media.

In the specification, the term "Master Transcriptional Regulators (MTRs)" should be understood to mean a specific set of Transcription Factors (TFs) that are upstream of, and have been shown to regulate, core proliferation genes involved in cancer progression and metastasis. In other words, these specific MTRs regulate cancer and in particular, breast cancer progression.

In the specification, the term "positive expression" as applied to a gene or a protein encoded by that gene should be understood to mean a level of expression of the gene or protein encoded by that gene that is increased above an average level of expression of the same gene or protein encoded by that same gene found in a cohort of matched control individuals with cancer (the "control group"). The cohort of matched individuals may consist of individuals who did not experience a recurrence of a cancer following surgery to remove the cancer. In relation to controls, the usual practise for one skilled in the art would be to use a 'standard' control, for example, for Immunohistochemistry (IHC), a cell line or cell lines where the expression level of the biomarker is known, or for qPCR (quantitative Polymerase Chain Reaction), a similar standard control or a pool of a number of samples is known.

In the specification, the term "dysregulated expression" as applied to $p16^{INK4A}$ expression should be understood to mean a level of expression of $p16^{INK4A}$ that is negative, increased above or decreased below a level of expression of the $p16^{INK4A}$ found in a cohort of matched individuals with cancer that did not recur following surgery to remove the cancer.

The terms "normal expression" or "moderate expression" as applied to a gene or protein should be understood to mean a level of expression of the gene (or protein encoded by that gene) that is equivalent to a level of expression of the same gene or protein encoded by that same gene found in a cohort of matched control individuals with cancer. The cohort of matched individuals may consist of individuals who did not experience a recurrence of a cancer following surgery to remove the cancer.

The method used to set thresholds is different for the microarray analysis, qRT-PCR analysis, and protein expression. For microarrays, the threshold is relative (samples were split into three equal groups, so the threshold is dataset dependent), and for the qPCR and protein expression it is set at specific points. For RNA (microarrays), expression levels of 'low', 'moderate' and 'high' refer to expression values that fall within the lower, middle or upper third of the expression range; or alternatively, 'low' and 'high' expression can refer to expression values that fall within the lower or upper half of the expression range. For qRT-PCR and protein expression levels, specific thresholds have been set, but in general, the term "dysregulated" refers to tumours with expression values falling above or below set values in the range of expression. For the terms "moderate" and "normal", the terms refer to tumours with expression values falling within set values in the range of expression. For example, for $p16^{INK4A}$, the normalised qRT-PCR thresholds for 'moderate' expression are 0.7 and 1.99. The normalised protein thresholds (using IHC) are 1% and 50% of positive cells. That is, a moderate score here refers to a tumour with >1% and <50% tumour cells positive for $p16^{INK4A}$. These values may be adjusted based on any new data but the same theory applies for the terms "normal", "moderate" and "dysregulated" with respect to expression levels of $p16^{INK4A}$.

In the specification, the term "adjuvant therapy" should be understood to mean any treatment given after primary treatment to increase the chances of long-term survival. In the specification, the term "neoadjuvant therapy" should be understood to mean treatment given before primary treatment to increase the chances of long-term survival. Primary treatment is generally surgery. Adjuvant therapy and neoadjuvant therapy are generally selected from chemotherapy, hormonal therapy, targeted therapy, radiation therapy, immunotherapy or a combination thereof.

In the specification, the term "sample" should be understood to mean tumour cells, tumour tissue, non-tumour tissue, conditioned media, blood or blood derivatives (serum, plasma etc), urine, or cerebrospinal fluid.

Detection of expression generally involves immunohistological staining of a tumour biopsy tissue or a control biopsy tissue using suitable means such as immunohistochemical staining; however, many other means of detecting the biomarkers of the invention will be apparent to those skilled in the art. For example, quantitative polymerase chain reaction (PCR), reverse transcriptase PCR (RT-PCR), quantitative real time RT-PCR (qRT-PCR), ELISA, Western Blot, protein determination on polyacrylamide gels, and the like.

In this specification, the term "cancer" should be understood to mean a cancer that is treated by chemotherapeutic regimens. An example of such a cancer include multiple myeloma, prostate cancer, glioblastoma, lymphoma, fibrosarcoma; myxosarcoma; liposarcoma; chondrosarcom; osteogenic sarcoma; chordoma; angiosarcoma; endotheliosarcoma; lymphangiosarcoma; lymphangioendotheliosarcoma; synovioma; mesothelioma; Ewing's tumour; leiomyosarcoma; rhabdomyosarcoma; colon carcinoma; pancreatic cancer; breast cancer; node-negative, ER-positive breast cancer; early stage, node positive breast cancer; early stage, node positive, ER-positive breast cancer; ovarian cancer; squamous cell carcinoma; basal cell carcinoma;

adenocarcinoma; sweat gland carcinoma; sebaceous gland carcinoma; papillary carcinoma; papillary adenocarcinomas; cystadenocarcinoma; medullary carcinoma; bronchogenic carcinoma; renal cell carcinoma; hepatoma; bile duct carcinoma; choriocarcinoma; seminoma; embryonal carcinoma; Wilms' tumour; cervical cancer; uterine cancer; testicular tumour; lung carcinoma; small cell lung carcinoma; bladder carcinoma; epithelial carcinoma; glioma; astrocytoma; medulloblastoma; craniopharyngioma; ependymoma; pinealoma; hemangioblastoma; acoustic neuroma; oligodendroglioma; meningioma; melanoma; retinoblastoma; and leukemias.

In this specification, the term "early stage" as applied to a cancer, especially a breast cancer, should be understood to mean tumours which are locally invasive but have not spread to the regional axillary lymph nodes or any other region of the body outside the breast tissue. That is, the cancer has not spread beyond the breast or the lymph nodes in the armpit on the same side of the body nor to any other part of the body.

In the specification, the term "early stage, node positive breast cancer" should be understood to mean tumours which are locally invasive and have spread to between 1-3 regional axillary lymph nodes, but not to any other region of the body outside the breast tissue.

In this specification, the term "node-negative" as applied to a cancer, especially a breast cancer, should be understood to mean tumours which have not spread to the regional axillary lymph nodes or any region outside the breast tissue.

In the specification, the terms "breast cancer patient" or "patient" means a patient who has a primary breast cancer tumour and awaits treatment for the cancer or has already undergone or is undergoing treatment for the primary tumour. The term should also be understood to include a patient who has had a primary breast cancer and is in remission, for example remission following treatment including one or more of tumour resection, first line chemotherapy, radiotherapy, hormonal therapy, other targeted therapy, or a combination of the above. Usually, the patient will be a breast cancer patient who has, or is undergoing, treatment for a primary tumour and who has been identified as having potential for developing a metastatic phenotype. In one embodiment, the patient has an ER-positive, node negative breast cancer.

In the specification, the term "recurrence" should be understood to mean the recurrence of the cancer which is being sampled in the patient, in which the cancer has returned to the sampled area after treatment, for example, if sampling breast cancer, recurrence of the breast cancer in the (source) breast tissue. The term should also be understood to mean recurrence of a primary cancer whose site is different to that of the cancer initially sampled, that is, the cancer has returned to a non-sampled area after treatment, such as non-locoregional recurrences.

In this specification, the term "poor outcome" should be understood to mean that the chances of disease free survival are low.

In the specification, the term "survival rate" should be understood to mean the period of time during which a patient diagnosed with cancer such as breast cancer, will likely survive. The survival rate is expressed as a 5-year survival rate, a 10-year survival rate, a 15-year survival rate, a 20-year survival rate, a 25-year survival rate, a 30-year survival rate, a 35-year survival rate, a 40-year survival rate, a 45-year survival rate, or a 50-year survival rate. Ideally, the survival rate is expressed as a 5-year survival rate or a 10-year survival rate.

In this specification, the term "treatment" should be understood to mean its generally accepted meaning which encompasses prohibiting, preventing, restraining, and slowing, stopping or reversing progression or severity of a metastatic, recurrent or existing breast cancer phenotype or other cancer phenotype.

In this specification, the term "at least two" should be understood to mean and encompass that at least two, at least three, at least four, at least five, at least six, at least seven, at least eight, at least nine or all genes can be selected from the group consisting of FOXM1, UHRF1, PTTG1, E2F1, MYBL2, HMGB2, ATAD2, E2F8, ZNF367 and TCF19.

The computer readable storage media can be any available tangible media that can be accessed by a computer. Computer readable storage media includes volatile and non-volatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable storage media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable storage media on which such instructions are embodied may reside on one or more of the components of either of a system, or a computer readable storage medium described herein, may be distributed across one or more of such components.

The computer-readable storage media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention include at minimum a determination system, a storage device, optionally a comparison module, and a display module. The functional modules can be executed on one, or multiple, computers, or by using one, or multiple, computer networks. The determination system has computer executable instructions to provide e.g., expression levels of at least two genes (or a protein encoded by said genes) selected from the group consisting of FOXM1, UHRF1, PTTG1, E2F1, MYBL2 and HMGB2, and optionally including $p16^{INK4A}$, in computer readable form.

The determination system, can comprise any system for assaying a breast cancer tumour sample for expression of genes (or proteins encoded by said genes) selected from the group consisting of FOXM1, UHRF1, PTTG1, E2F1, MYBL2, HMGB2, ATAD2, E2F8, ZNF367, TCF19 and $p16^{INK4A}$. Standard procedures, such as immunohistochemistry, a Western Blot, a Northern Blot, a Southern Blot, quantitative polymerase chain reaction (PCR), reverse transcriptase PCR (RT-PCR), quantitative real time RT-PCR (qRT-PCR), an enzyme-linked immunosorbent assay (ELISA), protein determination on polyacrylamide gels, RNA sequencing, RNA microarrays and other RNA hybridisation or amplification techniques, and such methods known to those skilled in the art, may be employed.

The information determined in the determination system can be read by the storage device. As used herein the "storage device" is intended to include any suitable computing or processing apparatus or other device configured or adapted for storing data or information. Examples of an electronic apparatus suitable for use with the present invention include a stand-alone computing apparatus, data telecommunications networks, including local area networks (LAN), wide area networks (WAN), Internet, Intranet, and Extranet, and local and distributed computer processing systems. Storage devices also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device is adapted or configured for having recorded thereon nucleic acid sequence information. Such information may be provided in digital form that can be transmitted and read electronically, e.g., via the Internet, on diskette, via USB (universal serial bus) or via any other suitable mode of communication.

As used herein, "stored" refers to a process for encoding information on the storage device. Those skilled in the art can readily adopt any of the presently known methods for recording information on known media to generate manufactures comprising information relating to FOXM1, UHRF1, PTTG1, E2F1, MYBL2, HMGB2, ATAD2, E2F8, ZNF367, TCF19 and $p16^{INK4A}$ expression in a sample.

In one embodiment the reference data stored in the storage device to be read by the comparison module is compared.

The "comparison module" can use a variety of available software programs and formats for the comparison operative to compare FOXM1, UHRF1, PTTG1, E2F1, MYBL2, HMGB2, ATAD2, E2F8, ZNF367, TCF19 and $p16^{INK4A}$ expression information data determined in the determination system to reference samples and/or stored reference data. In one embodiment, the comparison module is configured to use pattern recognition techniques to compare information from one or more entries to one or more reference data patterns. The comparison module may be configured using existing commercially-available or freely-available software for comparing patterns, staining, and may be optimized for particular data comparisons that are conducted. The comparison module provides computer readable information related to the expression levels of FOXM1, UHRF1, PTTG1, E2F1, MYBL2, HMGB2, ATAD2, E2F8, ZNF367, TCF19 and $p16^{INK4A}$ of the sample.

The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content based in part on the comparison result that may be stored and output as requested by a user using a display module.

The methods described herein therefore provide for systems (and computer readable media for causing computer systems) to perform methods as described in the Statements of Invention above, for example methods for diagnosing metastatic potential or recurrence potential of a breast cancer or a non-breast cancer in an individual or methods for identifying a breast cancer patient or a non-breast cancer patient suitable for treatment or prevention of metastatic or recurrent cancer with a suitable chemotherapeutic adjuvant or non-adjuvant therapeutic.

Systems and computer readable media described herein are merely illustrative embodiments of the invention for performing methods of diagnosis in an individual, and are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

Materials and Methods
Cell Culture

Primary HMEC cells were grown as described (Garbe et al., 2009). HMEC-tert cells were immortalised using a pBABE-hTERT-hygro construct. Mouse embryonic fibroblasts (MEFs) were derived from embryonic day 13.5 C57BL6 mouse embryos and maintained in DMEM media supplemented with 10% (v/v) FBS (Hyclone), 100 U/ml penicillin and 100 U/ml streptomycin (Gibco).

RNA Sequencing

Total RNA was extracted from proliferating and senescent HMECs using the RNeasy kit (Qiagen). Polyadenylated RNA species were enriched from 5 μg total RNA, and sequencing libraries were prepared from PolyA+RNA using the TruSeq Sample Prep kit (Illumina). Libraries were used directly for cluster generation and sequencing analysis using the Genome Analyser II (Illumina) following the protocol of the manufacturer. Base calling and mapping to the human genome (build hg19) were performed using the BWA sequence alignment tool. The mRNA fold changes were calculated based on the total number of sequence reads mapped per gene in the two experiments.

DNA Microarray Analysis

Total RNA was extracted from proliferating and senescent MEFs using the RNeasy kit (Qiagen). For each time point. RNA was prepared from three independent MEF cultures and pooled to reduce experimental variation. Cy3 labeled cRNA, for use with a custom designed 44 k microarray (Agilent), was prepared and hybridized to the supplier's instructions. Microarrays were scanned using Agilent's DNA microarray scanner and data analysed as previously described (Hokamp et al., 2004). Gene ontology analysis was carried out using the DAVID bioinformatics resource (available on the world wide web at david.abcc.ncifcrf.gov/). Publicly available breast cancer microarray datasets were downloaded from Rosetta Inpharmatics and Gene Expression Omnibus (GSE6532 and GSE3494). Within each dataset, the expression data of each gene was divided at the median into two groups, or at the $33^{rd}$ and $66^{th}$ percentile into 3 groups, depending on the analysis. To generate a combined MTR score, the gene expression values for each of the 6 genes were divided at the median, given a score of 1 or 2 based on the expression level, and the sum of these scores was then divided, as above, to create 2 or 3 groups. INK4A gene expression was divided into 3 groups (low, moderate and high) at the $33^{rd}$ and $66^{th}$ percentile. The moderate group was given a score of 1 and the low and high groups were combined and given a score of 2. To generate the OncoMasTR RNA score, the combined MTR score and the INK4A score were summed together and the final scores were divided into 2 or 3 groups. Duplicate samples were removed in the combined microarray dataset. The genefu package in R was used to estimate the risk groups which approximate the Oncotype Dx® assay (based on 21-gene signature), and the MammaPrint assay (based on 70-gene signature) (Haibe-Kains et al). For the Van de Vijver dataset, the previously defined 70-gene risk groups were used (van de Vijver et al., 2002).

Real-Time Quantitative PCR

Total RNA was extracted from cells using the RNeasy kit (Qiagen) according to manufacturer's protocol. 1 ug RNA was used to generate cDNA by reverse transcriptase PCR using the TaqMan Reverse Transcription kit (Applied Biosytems). Relative mRNA expression levels were determined using the SYBR Green I detection chemistry (Applied Biosystems) on the ABI Prism 7500 Fast Real-Time PCR System. The ribosomal constituent RPLPO was used as a control gene for normalization (SEQ ID NO: 39 (Forward—TTCATTGTGGGAGCAGAC) and SEQ ID NO: 40 (Reverese—CAGCAGTTTCTCCAGAGC)). Primer sequence pairs used are as follows (For =Forward Primer; Rev=Reverse Primer):

SEQ ID NO: 1 For:
AGACCGTCCTCAACCAGCTCTTC
and

SEQ ID NO: 2 Rev:
GAAGTGCTTGGAGATCACCGG;

SEQ ID NO: 3 For:
CAA CAA TAG CCT ATC CAA CAT CCA G
and

SEQ ID NO: 4 Rev:
GGA GCC CAG TCC ATC AGA ACT C;

SEQ ID NO: 5 For:
CTGCCTGAAGAGCACCAGATTG
and

SEQ ID NO: 6 Rev:
CAAGGATCATGAGAGGCACTCC;

SEQ ID NO: 7 For:
CACTGACCAGCAATGCCAGTAC
and

SEQ ID NO: 8 Rev:
CCCCTTGACAAGGTCTGGATTC;

SEQ ID NO: 9 For:
GCTCCTAAAAGGCCACCATCTG
and

SEQ ID NO: 10 Rev:
TGATCTTTGGGCGATGTTCAG;

SEQ ID NO: 11 For:
TGT CAG GAC CTT CGT AGC ATT G
and

SEQ ID NO: 12 Rev:
GGG CTT TGA TCA CCA TAA CCA TC;

SEQ ID NO: 13 For:
CAA TCT CAA CAA AAC CCT TGG C
and

SEQ ID NO: 14 Rev:
CTC GGC GTA CTT ATT CTC CTC C;

SEQ ID NO: 15 For:
AGAGGATTTGAGGGACAGGGTC
and

SEQ ID NO: 16 Rev:
CCTCTTTCTTCCTCCGGTGC;

SEQ ID NO: 17 For:
ATGGAGCTGGGTGCTGAGAAC
and

SEQ ID NO: 18 Rev:
CCTTCTTCAACTCCATGAGCCC;

SEQ ID NO: 19 For:
ACA AAG AAG GAA ATA GAG GGA CCG
and

SEQ ID NO: 20 Rev:
GAT GAG TGG GAG ACT TGG GTT C;

SEQ ID NO: 21 For:
CAGCCCGAGCTTTTGTTACAAC
and

-continued

SEQ ID NO: 22 Rev:
TTCGCTGCTGACATCTGAGTTC;

SEQ ID NO: 23 For:
AAGGTGAGCAAGATGGAAATCC
and

SEQ ID NO: 24 Rev:
CGATCTGCAGGTCCAAGATGTAG

SEQ ID NO: 25 For:
CTCTCTGAGGCCAAGGATCTCC
and

SEQ ID NO: 26 Rev:
CCTTGTTGCAGTATTTGCAGTTG;

SEQ ID NO: 27 For:
TGAGCCTGCAGATTTTAAGGTG
and

SEQ ID NO: 28 Rev:
TGGAAAGCTTCTCACGGCATAC;

SEQ ID NO: 29 For:
AGCTGGCCTGAATCATTAATACG
and

SEQ ID NO: 30 Rev:
GGTGAAGGTCCATGAGACAAGG;

SEQ ID NO: 31 For:
GGGACAGTAAAAATGTGTCCTGC
and

SEQ ID NO: 32 Rev:
TGCCAGCAATAGATGCTTTTTG;

SEQ ID NO: 33 For:
CAT TCC CGC TCT CCT TCC C
and

SEQ ID NO: 34 Rev:
GCT CGG CTC CCC AGA ATC;

SEQ ID NO: 35 For:
CCTCACTGGAGGAGTGATGCG
and

SEQ ID NO: 36 Rev:
AAGCATCCTAAGCCATTCCATG;

SEQ ID NO: 37 For:
CCA TTG AAA ACA AGG ACG ATG C
and

SEQ ID NO: 38 Rev:
CTG TCC CCA ACA ACA TCA AGC.

ChIP and ChIP-Sequencing

ChIP analyses were performed as described previously (Bracken et al., 2006). For ChIP-SEQ, DNA from 10 independent ChIP experiments was pooled and quantified using a Qubit fluorometer (Invitrogen). Sequencing libraries were generated using 100 ng of immunoprecipitated DNA using the ChIP-SEQ Sample Prep Kit (Illumina). Amplified library DNA was purified by gel isolation and quality checked to unsure the absence of adaptor dimer contamination using the Bioanalyzer 2100 and DNA High Sensitivity Chip assay (Agilent). DNA libraries were quantified and diluted to 10 pM. Diluted libraries were used directly for cluster generation and sequencing analysis using the Genome Analyser II (Illumina) following the protocol of the manufacturer. Base calling and mapping to the human genome (hg19) of the 42-bp sequences were done using the Bowtie alignment tool allowing for up to 2 mismatches in each read. To avoid any PCR bias only two reads per chromosomal position were allowed, thus eliminating spurious spikes. Peak detection was performed using MACs, and input DNA was used as a control for normalization.

ARACNe Analysis

Breast cancer transcriptional networks were generated by ARACNe (Margolin et al., 2006), using published breast cancer datasets (ExPO; Loi et al., 2007; van de Vijver et al., 2002), and queried using in-house or published gene signatures. For the ExPO and Loi networks, ARACNe was run on the complete expression datasets, whereas for the NKI network, a filtering step was applied prior to ARACNe to remove uninformative probes. The 70 gene Mammaprint signature was derived though supervised classification of DNA microarray data from 78 lymph node-negative patients, and predicts a short time to distant metastasis (van't Veer et al., 2002). The larger 231-gene signature from which the 70-gene signature was derived was used for this analysis. The Genomic Grade signature was developed from a training dataset of 64 ER-positive breast tumors, and is composed of genes differentially expressed between low and high histologic grade. The larger 207-gene set list from which the 97-gene Genomic Grade Index was derived was used for ARACNe analysis (Sotiriou et al., 2006).

Statistical Analysis

Kaplan-Meier survival curves were used for survival analysis and Chi square and p-values were calculated using log-rank test. Multivariate Cox proportional hazards analysis was used to evaluate the added prognostic value of individual genes and combined scores, on top of a standard clinical model including age (<50, >=50 years), nodal status (positive or negative), tumour size (<2 cm, >=2 cm), tumour grade (1 vs. 2 and 3), treatment status, and ER and HER2 status. Multivariate analysis was also carried out using the standard clinical model above, plus the 21-gene signature predicted risk group. The contribution of each marker was assessed by the change in likelihood ratio (LR-Chi, df=1) and p-values were calculated. A p-value of less than 0.05 was considered significant. The primary clinical endpoint used for analysis for the microarray and TMA data was recurrence-free survival (RFS). All statistical analysis was carried out using the R programming language (version 2.15.0). Heatmaps were created using an online tool (available on the world wide web at chibi.ubc.ca/matrix2png). Enrichment analysis was carried out by calculating the number of unique 'poor prognosis' genes present in the 'core proliferation' signature, compared to what would be expected across the genome (Observed/Expected). Unique genes in the 'poor prognosis' signatures were n=61 for the MammaPrint signature, and n=207 for the Genomic Grade signature, and analysis was normalised based on the experimental platform used to derive the signature.

TMA Cohort

The tissue microarray (TMA) used in this study was derived from a reference cohort of 512 consecutive invasive breast cancer cases diagnosed at the Department of Pathology, Malmo University Hospital, Malmo, Sweden, between 1988 and 1992, and has been previously described (Svensson et al., 2005). In brief, the median age was 65 years (range 27-96) and median follow-up time regarding disease-specific and overall survival was 11 years (range 0-17). Patients with recurrent disease and previous systemic therapies were excluded, as well as a number of misclassified ductal carcimona in situ (DCIS) cases. Two hundred and sixty-three patients were dead at the last follow-up (December 2004), 90 of which were classified as breast cancer-specific deaths. Tissue cores (1 mm) from areas representative of invasive cancer were extracted from donor blocks and arrayed in duplicate. This study has been approved by the Ethics Committee at Lund University and Malmo University Hospital.

Immunohistochemistry

TMA slides were deparaffinised in xylene and rehydrated in descending gradient alcohols. Heat-mediated antigen retrieval was performed using 10 mM sodium citrate buffer (pH 6.0) in a PT module (LabVision, UK) for 15 min at 95° C. The LabVision IHC kit (LabVision, UK) was used for staining. Endogenous peroxidase activity was blocked by incubation with 3% hydrogen peroxide for 10 min. Sections were blocked for 10 min in UV blocking agent and the relevant primary antibody was incubated for 1 hr. Sections were washed in phosphate buffered saline with 0.1% Tween 20 (PBS-T), following which primary antibody enhancer was applied for 20 min, and sections were washed in PBS-T. Sections were then incubated with HRP polymer for 15 min, washed in PBS-T and then developed for 10 min using diaminobenzidine (DAB) solution (LabVision, UK). All incubations and washing stages were carried out at room temperature. The sections were counterstained in haematoxylin, dehydrated in alcohol and xylene and mounted using DPX mounting medium. As a negative control, the primary antibody was substituted with PBS-T.

Primary antibodies used were HMGB2 (Abcam; 1:1500), UHRF1 (BD Biosciences; 1:1000), PTTG1 (Invitrogen; 1:500), FOXM1 (Santa Cruz, C20; 1:300), and p16 (Clone JCB; 1:5000). TMA sections had been previously been stained in the Ventana Benchmark (Ventana Medical Systems Inc, USA) using prediluted antibodies to ER (clone 6F11, Ventana), PR (clone 16, Ventana) and Her2 (Pathway CB-USA 760-2694), or in the Dako Techmate 500 (Dako, Denmark) for Ki-67 (1:200, M7240, Dako).

TMA Analysis

Slides were scanned at 20× magnification using a ScanScope XT slide scanner (Aperio Technologies, CA). For manual scoring, staining of tumor cells was evaluated by a pathologist on the basis of intensity, on a scale of negative (0), weak (1), moderate (2) and strong (3); and percentage, on a scale of 0-6 (0=0-1%; 1=1-10%; 2=10-25%: 3=25-50%; 4=50-75%; 5=75-90%; 6=90-100%). Staining for the factors HMGB2 and UHRF1 was predominantly nuclear, whereas PTTG1, FOXM1 and $p16^{INK4A}$ stained both the nuclear and cytoplasmic compartments and were scored accordingly. For UHRF1, PTTG1 and $p16^{INK4A}$, the percentage of positive tumor nuclei was the most significant variable in relation to outcome and was used in all further analysis. For HMGB2, a modified Allred score (intensity plus percentage) was used and, for FOXM1, the percentage of cytoplasmic positivity within tumor cells was the most significant variable. For analysis of the four MTRs, a threshold for positivity was applied independently for each variable, to create a binary score with low (0) and high (1) expression. For $p16^{INK4A}$, the 'negative' (0% positive cells) and 'high' (>50% positive cells) expression groups were combined and given a score of 1, and compared to the 'moderate' group with a score of 0. To generate a combined MTR score at the protein level, the sum of the binary scores for all four MTRs was generated. Tumors with high expression of >1 MTR were classified as having a high MTR score. To generate the combined 4MTR+$p16^{INK4A}$ score (Onco-MasTR IHC score), the binary 4MTR score was combined with the binary $p16^{INK4A}$ score, and divided into two groups with a threshold of >2.

Results

Identification of a 'Core Proliferation' Gene Expression Signature.

Figure 1B:
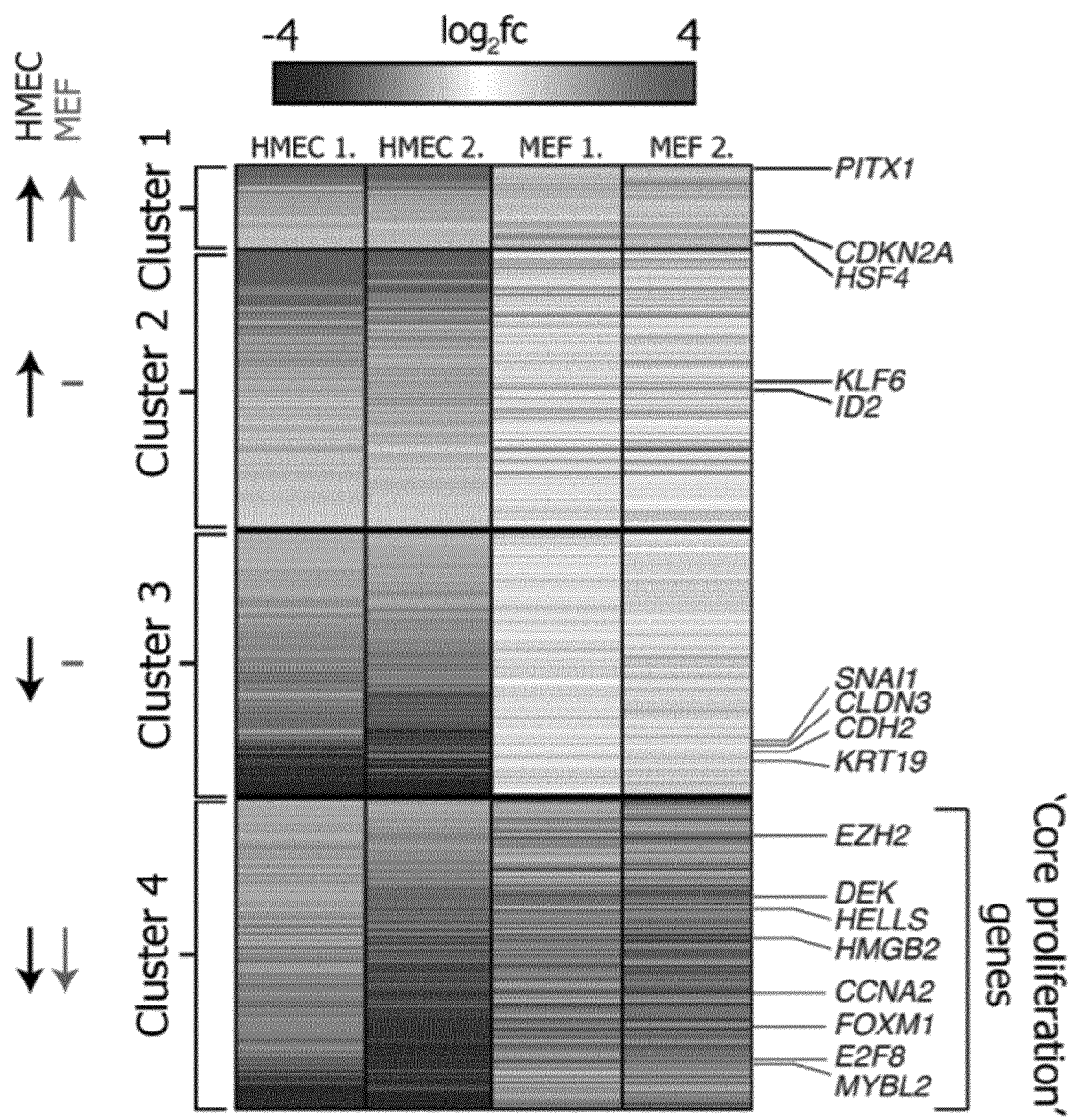
Figure 1C:
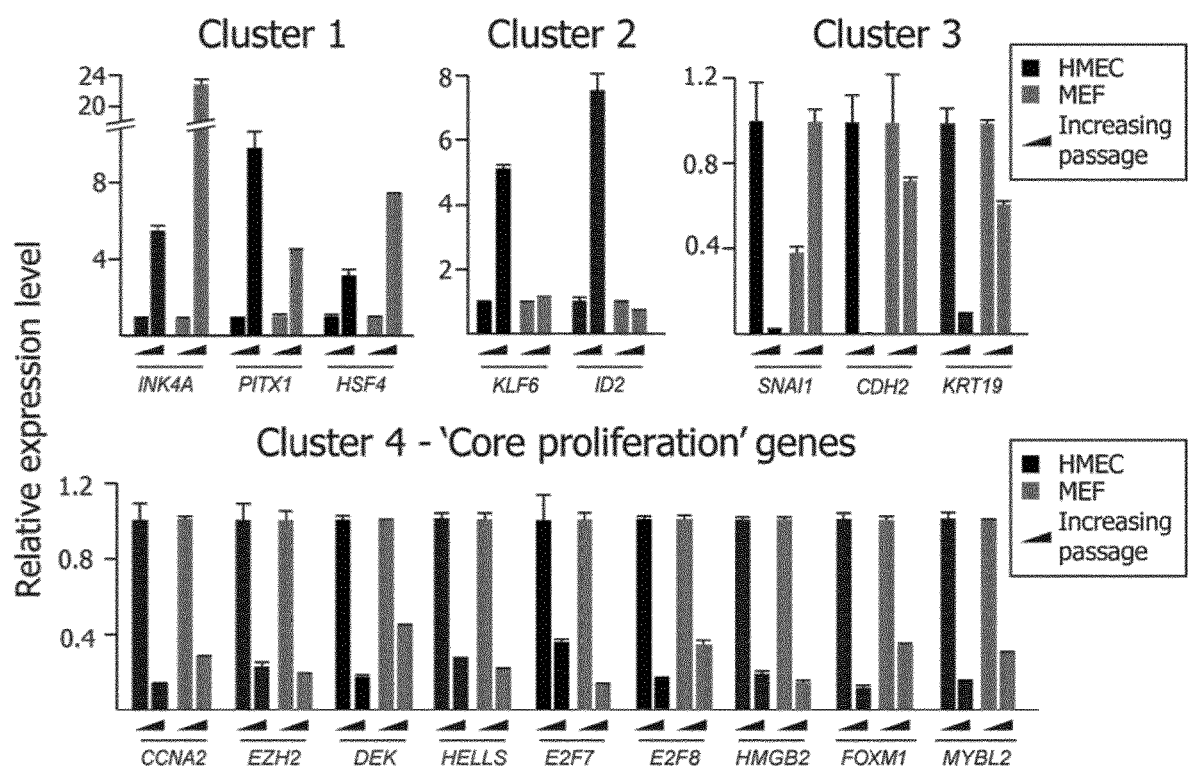
Figure 1D:
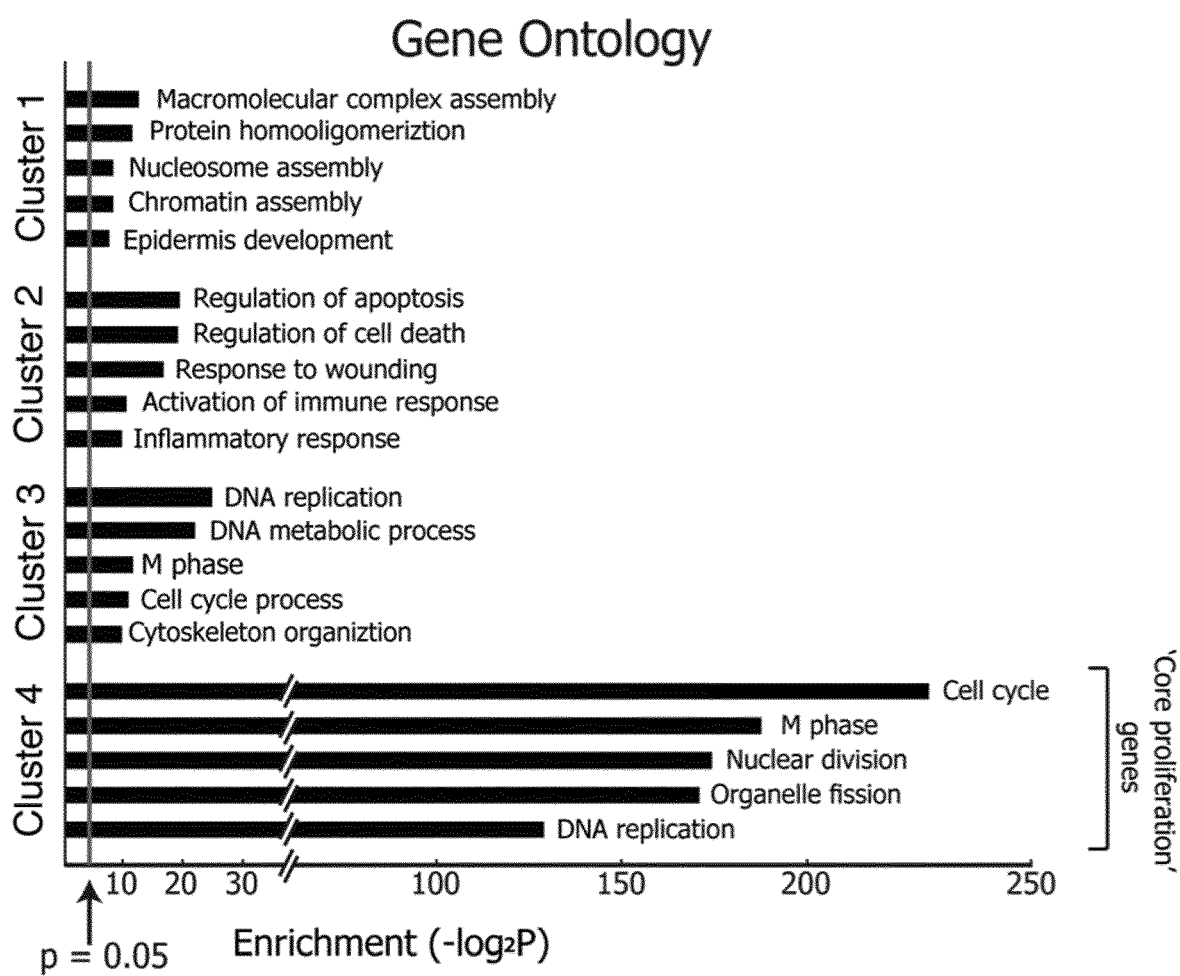

The applicant set out to identify a set of 'core proliferation' genes that are consistently highly expressed in actively growing cells in a lineage-independent fashion. To do this, the applicant isolated human mammary epithelial cells (HMECs) and mouse embryonic fibroblasts (MEFs) and passaged them towards cellular senescence, as characterised by an increase in the levels of $p16^{INK4A}$ (Zindy et al., 1997), and a decrease in the levels of the E2F target gene, EZH2 (Bracken et al., 2003) (FIG. 1A). The applicant next performed a genome-wide mRNA expression analysis on proliferating and senescing HMEC and MEF cultures and identified four differentially expressed gene clusters (FIG. 1B). The expression changes of representative genes from each cluster were validated by quantitative RT-PCR (FIG. 1C). The Cluster 3 genes, which were down-regulated during serial passaging of HMEC cells, included several genes involved in mammary epithelial cell-specific processes, such as the luminal cytokeratin KRT19 and the tight junction protein CLDN3. This is consistent with the fact that the proportion of luminal and myoepithelial cells shifts during serial passaging of HMEC cells (Garbe et al., 2009). Therefore, the applicant reasoned that many of the genes within Cluster 3 were down-regulated independently of the progressive decrease in proliferation rate. Consistent with this, a gene ontology analysis for each of the four gene clusters revealed a greater enrichment of functional categories linked to cell cycle and proliferation in Cluster 4, compared to Cluster 3 (FIG. 1D). Therefore, the strategy to combine the expression changes of both serially passaged MEF and HMEC allowed the identification of a 'core proliferation' genes in mammary epithelial cells.

Figure 1E:
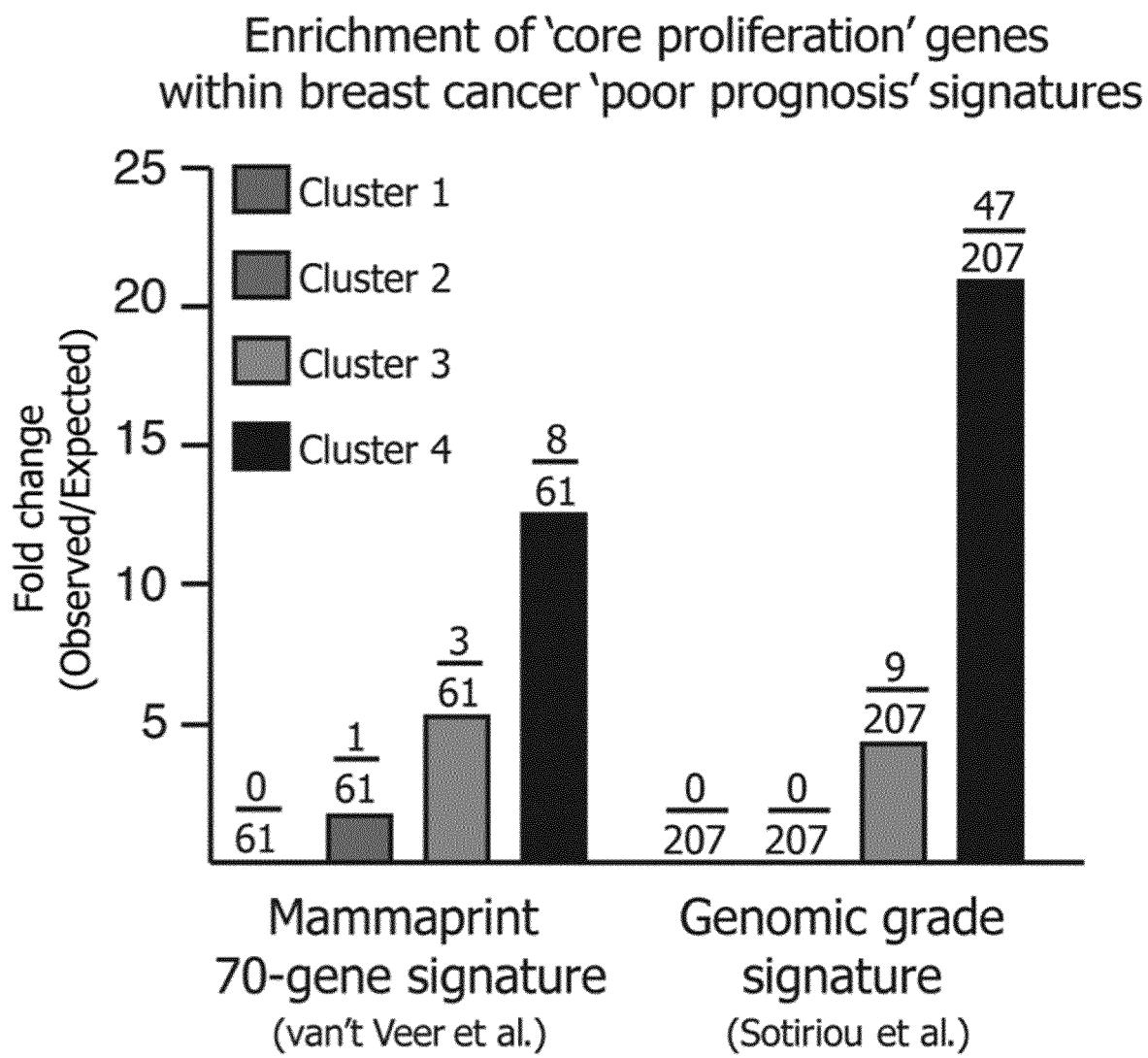

The applicant next wished to determine how enriched the Cluster 4 'core proliferation' genes were in two of the best known 'breast cancer poor prognosis' signatures, the MammaPrint 70-gene signature and the 'Genomic Grade' signature (Sotiriou et al., 2006; van't Veer et al., 2002). This revealed a significant enrichment of Cluster 4 genes, but not genes from Clusters 1-3, in both poor prognosis signatures (FIG. 1E), supporting the, perhaps unsurprising, view that a major contributor to the prognostic power of these two signatures is their ability to simply measure tumor cell proliferation (Mosley and Keri, 2008; Wirapati et al., 2008). Identification of Upstream Master Transcriptional Regulators (MTRs) of the 'Core Proliferation' Signature.

Interestingly, despite the ability of several established poor prognostic signatures to predict breast cancer outcome, there is surprisingly little overlap between the signatures themselves (Fan et al., 2006; Haibe-Kains et al., 2008). The applicant reasoned that the proliferative genes within these signatures, several of which are 'core proliferation' genes in the analysis presented herein (FIG. 1E), may in fact be just passengers, rather than drivers of tumour cell proliferation. Therefore, the applicant hypothesised that the upstream transcriptional regulators of the 'core proliferation' genes would be more reliable predictors of breast cancer prognosis.

Figure 2A:
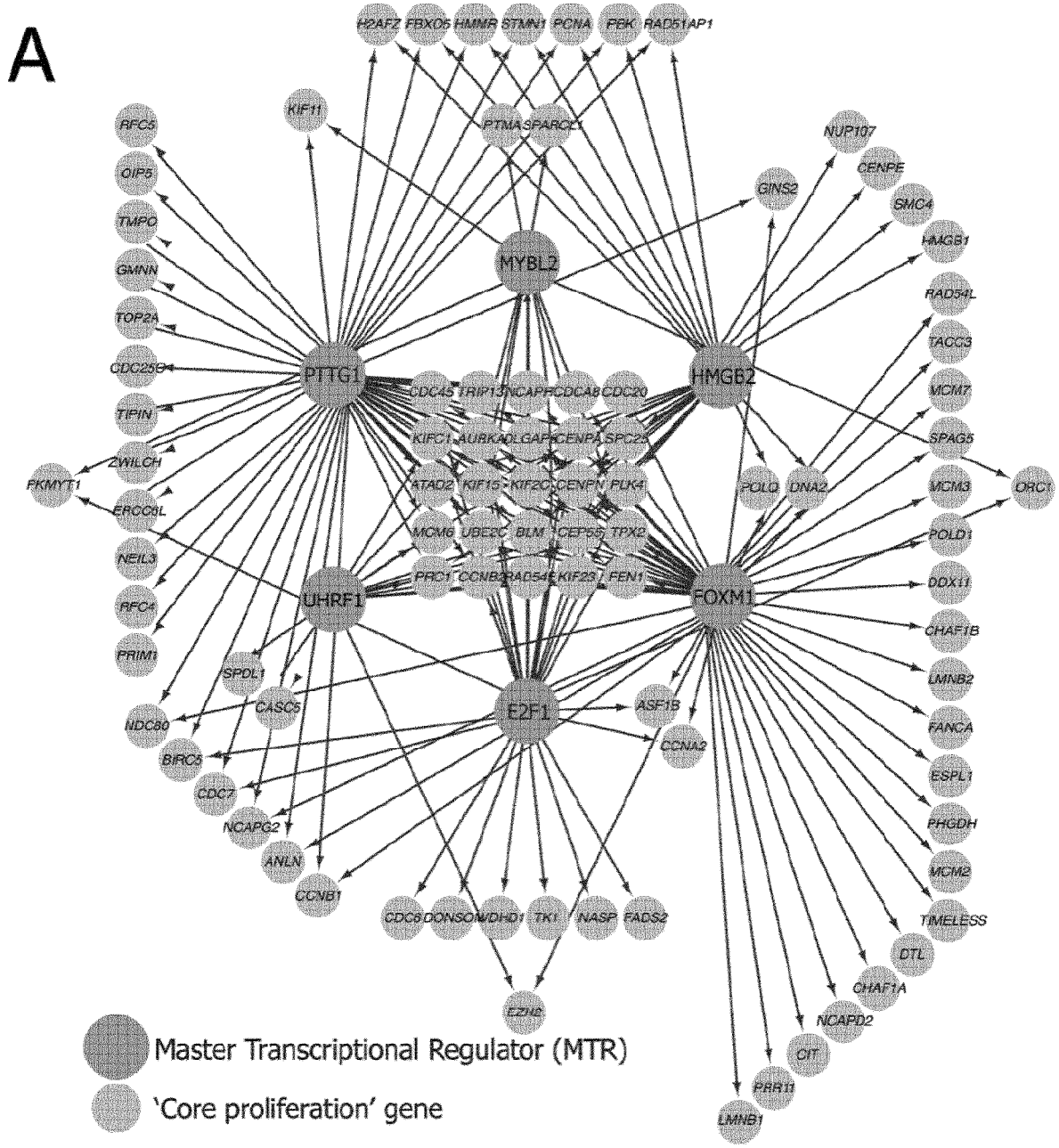
FIGS. 2A-2D illustrate that E2F1, FOXM1 and MYBL2 bind core proliferative genes in HMECs.

Considering the hierarchical nature of gene expression regulation, the applicant wished to identify the key transcriptional regulators upstream of the core proliferation signature. To identify the upstream master transcriptional regulators (MTRs) of the 'core proliferation' genes, a bioinformatic approach called ARACNe was used (Carro et al., 2010; Margolin et al., 2006). This approach uses interaction networks constructed from gene expression datasets to infer direct transcriptional interactions. ARACNe was applied to three publicly available breast cancer gene-expression datasets (ExPO; Loi et al., 2007; van de Vijver et al., 2002) and predicted several upstream MTRs of the 'core proliferation' genes in breast cancer (FIG. 2A and Table 1). Among the top scoring MTRs were Forkhead Box M1 (FOXM1), ubiquitin-like PHD and RING finger 1 (UHRF1), Securin or Pituitary Tumour-Transforming Gene 1 (PTTG1), E2F Transforming Factor 1 (E2F1), v-myb myeloblastosis viral oncogene homolog (avian)-like 2 (MYBL2) and High Mobility Group Box 2 (HMGB2), which were relatively consistent across the three independent breast cancer datasets, supporting the idea that the MTRs would prove to be more reliable indicators of tumor cell proliferation than their downstream target genes. Four additional genes were also identified consistently across datasets as being upstream of the 'core proliferation' genes. These are ATAD2, E2F8, ZNF367 and TCF19.

TABLE 1

Top ranking master transcriptional regulators of the indicated expression signatures as predicted by APvACNe

| Rank | Core Proliferation signature | Poor Prognosis signature | Genomic grade signature |
|---|---|---|---|
| 1 | FOXM1 | PTTG1 | PTTG1 |
| 2 | PTTG1 | FOXM1 | FOXM1 |
| 3 | UHRF1 | UHRF1 | UHRF1 |
| 4 | MYBL2 | ATAD2 | MYBL2 |
| 5 | HMGB2 | MYBL2 | ATAD2 |
| 6 | ATAD2 | ZNF367 | HMGB2 |
| 7 | E2F1 | HMGB2 | ZBTB20 |
| 8 | E2F8 | TCF19 | E2F1 |
| 9 | ZNF367 | E2F8 | E2F8 |
| 10 | TCF19 | E2F1 | ZNF367 |

Figure 2B:
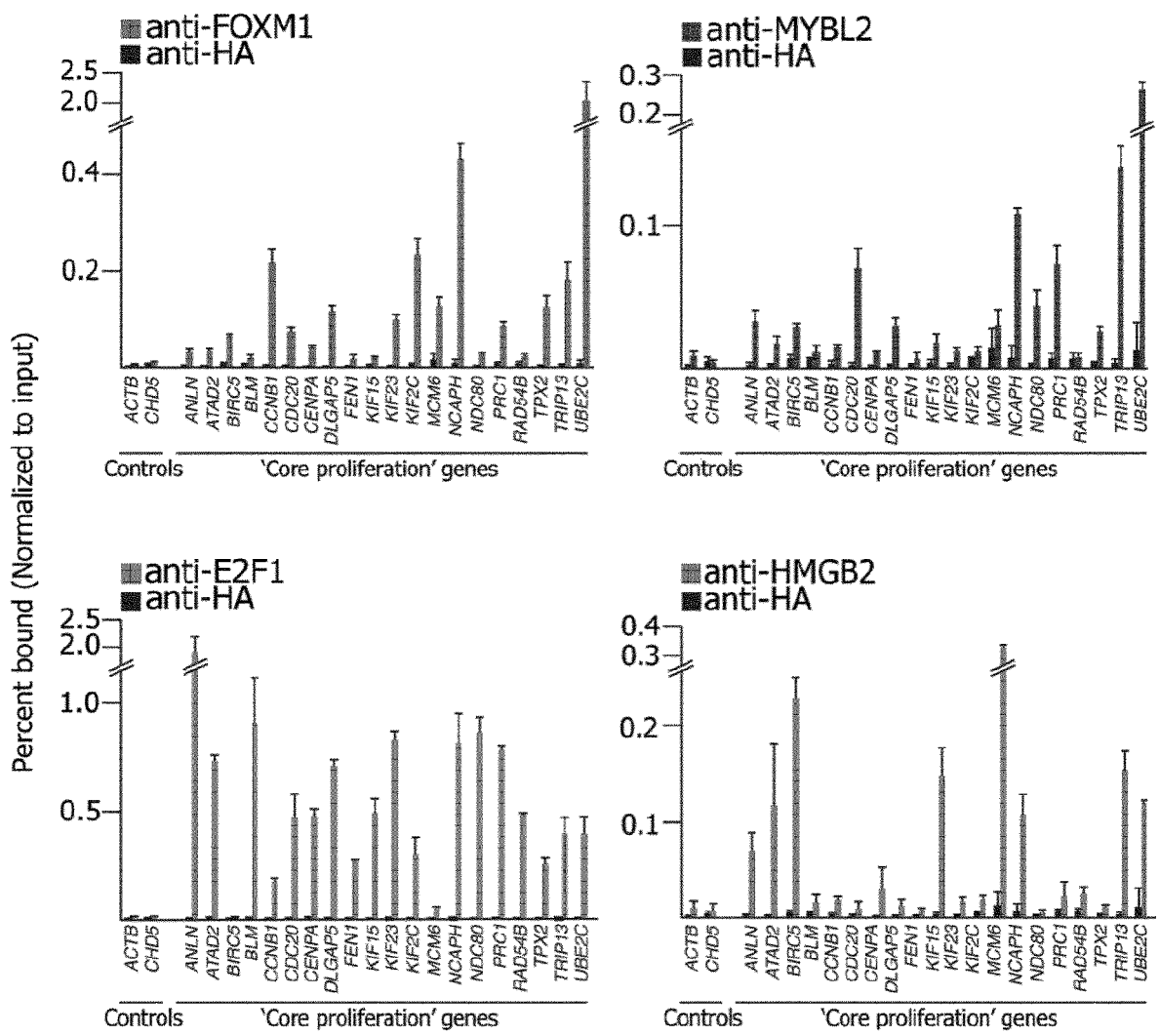
Figure 2C:
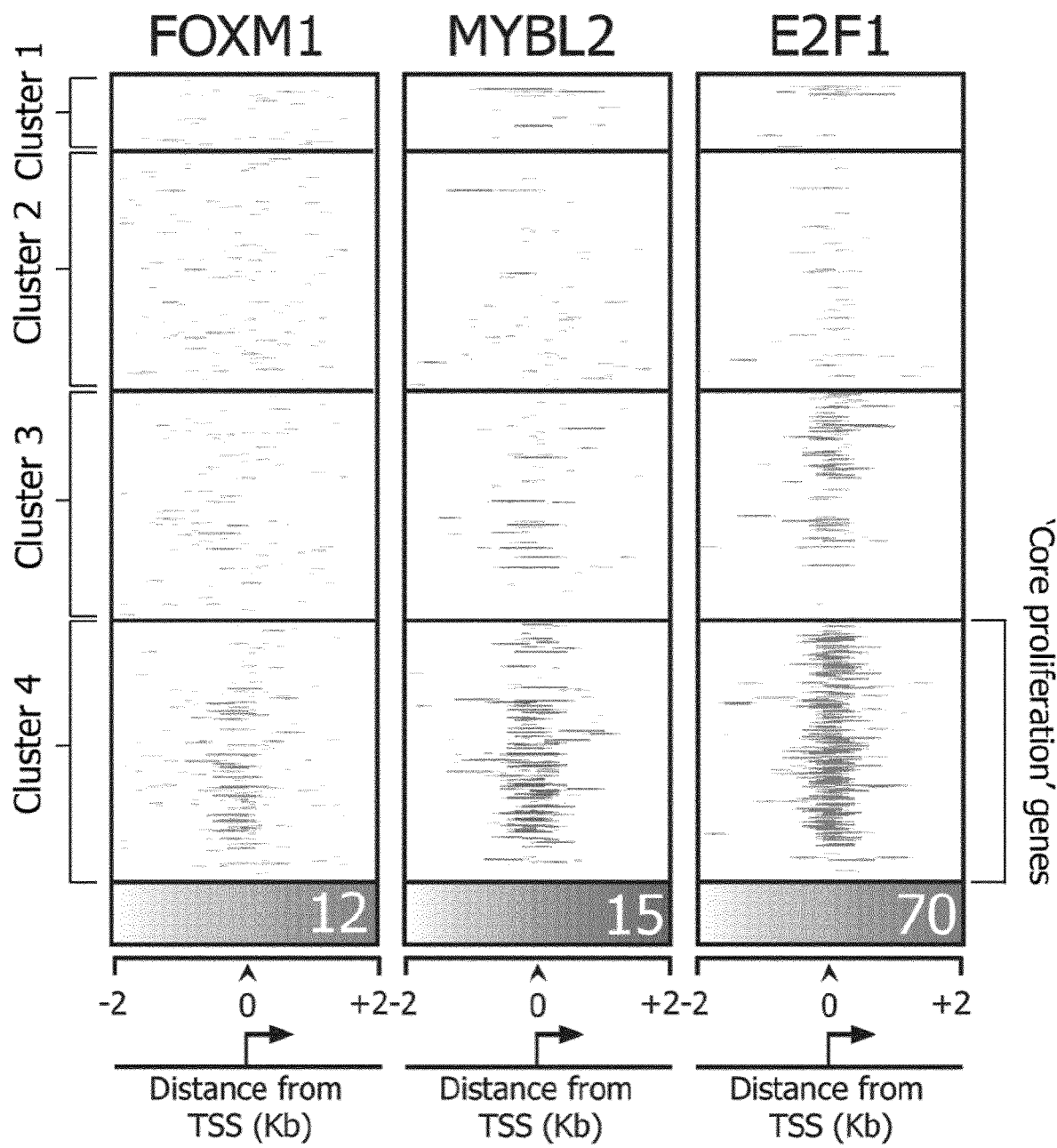
Figure 2D:
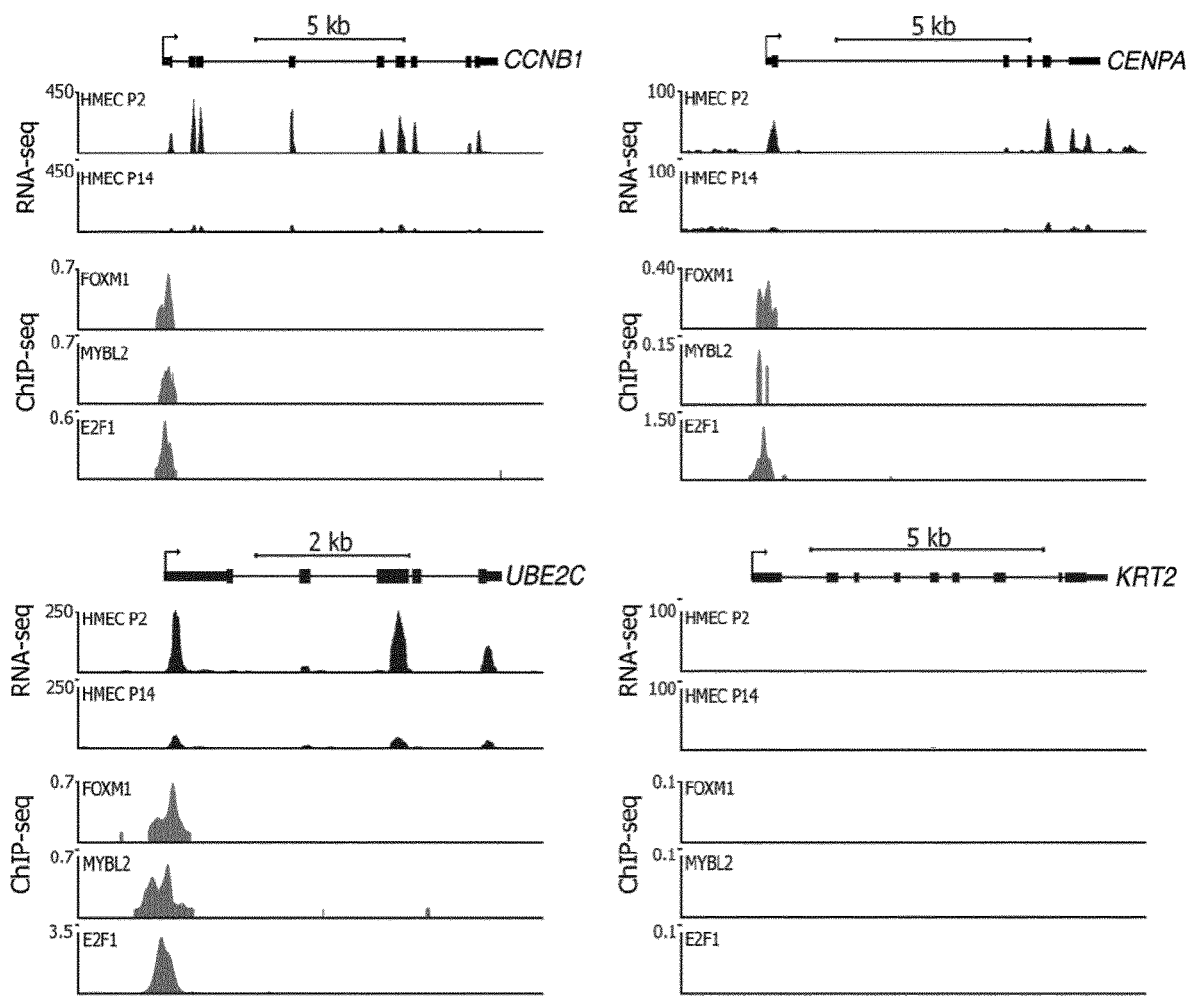

The applicant next wished to determine if some of the MTRs directly bind to the promoters of Cluster 4, 'core proliferation' genes, as predicted. Chromatin immunoprecipitations (ChIPs) followed by quantitative Real Time PCR (qPCR) confirmed the direct binding of four of the MTRs (FOXM1, MYBL2, E2F1 and HMGB2) to the promoters of 'core proliferation' genes in HMEC-Tert cells (FIG. 2B). To gain a broader view on MTR binding throughout the genome, ChIP followed by high-throughput sequencing (ChIP-seq) was performed on HMEC-Tert cells for E2F1, MYBL2 and FOXM1. This revealed that all three MTRs primarily associate with the promoters of the Cluster 4, 'core proliferation' genes, and to a lesser extent, some Cluster 3 genes (FIG. 2C). The ChIP-seq tracks of three representative genes show peaks depicting binding of E2F1, MYBL2 and FOXM1 on the CCNB1, UBE2C and CENPA gene promoters (FIG. 2D), but not on the promoter of a gene not expressed in HMECs, KRT2. The applicant was not able to investigate the genome-wide binding patterns of PTTG1 or UHRF1 due to the lack of suitable high quality ChIP-grade antibodies. However, the fact that PTTG1 has been reported to have a role in the transcriptional activation of cell cycle genes, supports the ARACNe predictions (Tong and Eigler, 2009; Tong et al., 2007). On the other hand, UHRF1 is generally considered to be a transcriptional repressor, being required for the maintenance of DNA methylation during cell division (Bostick et al., 2007). Therefore, UHRF1 is unlikely to directly regulate core proliferation genes, and is more likely to be a co-regulated proliferative gene. Supporting this possibility, E2F1, MYBL2, and FOXM1 also bind the promoter of the UHRF1 gene in HMEC cells.

In parallel with the identification of these MTRs, the Applicant also carried out unbiased survival analysis of 565 node-negative patients from four independent breast cancer gene expression datasets (Buffa et al., 2011; Ivshina et al., 2006; Loi et al., 2007; van de Vijver et al., 2002), in order to identify the genes associated with patient survival in ranked order (Table 2). Strikingly, this analysis identified several of the proliferation MTRs as among the top 20 genes associated with breast cancer outcome in these node-negative patients, with several of these proliferation MTRs scoring higher than conventional clinical biomarkers (ER, PR, Ki67) or genes incorporated into the Oncotype Dx® assay (BIRC5, CCNB1, BCL2, CTSL2). This result illustrated the power of these MTRs as prognostic biomarkers, and inspired us to investigate them further.

TABLE 2

Unbiased survival analysis of all genes across four breast cancer datasets (Van de Vijver et al, Loi et al, Ivshina et al, Buffa et al.,). Gene expression values were divided at the median, analysed in relation to overall survival using the log rank test, and ranked in order of prognostic power.

| Rank | Gene | Function |
|---|---|---|
| 1 | PRC1 | Cell cycle |
| 2 | *UHRF1* | *Proliferation MTR* |
| 3 | ZWINT | Cell cycle |
| 4 | IGBP1 | Signal transduction |
| 5 | RPL29 | Ribosomal protein |
| 6 | CCNB2 | Proliferation |
| 7 | TRIP13 | DNA repair |
| 8 | CDC45L | Cell cycle |
| 9 | TROAP | Cell adhesion |
| 10 | TACC3 | Proliferation |
| 11 | LRP2 | Lipoprotein/Hormone signalling/Stress response |
| 12 | MAD2L1 | Cell cycle |
| 13 | BLM | DNA replication and repair |
| 14 | CDKN3 | Cell cycle |
| 15 | SEC14L2 | Cholesterol Biosynthesis |
| 16 | *MYBL2* | *Proliferation MTR (and Oncotype Dx)* |
| 17 | BIRC5 | Oncotype Dx ® (Anti-apoptosis) |
| 18 | *PTTG1* | *Proliferation MTR* |
| 19 | H2AFZ | Chromatin remodeling |
| 20 | TK1 | DNA replication |
| 21 | FBXO5 | Ubiquitin pathway |
| 22 | EIF2C2 | RNAi pathway |
| 23 | EBP | Cholesterol Biosynthesis |
| 24 | PLP2 | Endoplasmic reticulum protein |
| 25 | EZH2 | Proliferation/Polycomb protein |
| 26 | *FOXM1* | *Proliferation MTR* |
| 27 | PDZK1 | Scaffolding protein/Cholesterol metabolism |
| 28 | FEN1 | DNA repair |
| 29 | TXNRD1 | Oxidative stress |
| 30 | COL4A1 | Basement membrane component |
| 31 | STC2 | Calcium homeostasis/Estrogen signalling |
| 32 | GPR56 | Cell signalling |
| 33 | SQLE | Sterol Biosynthesis |
| 34 | EXO1 | DNA repair |
| 35 | YWHAZ | Anti-apoptosis |
| 36 | GATA3 | Hormone Response |
| 37 | KIF4A | Cell cycle |
| 38 | ADM | Hormone sigalling |
| 39 | CREBL2 | Cell cycle |
| 40 | TTK | Proliferation |
| 41 | BUB1 | Cell cycle/Apoptosis |
| 42 | CTPS | DNA synthesis |
| 43 | CHST3 | Cell migration/Wound response |
| 44 | CAMLG | Apoptosis/Calcium homeostasis |
| 45 | PSMD1 | Proteasome component |
| 46 | KIF13B | DNA damage pathway |
| 47 | NRM | Nuclear membrane protein |
| 48 | STXBP2 | Vesicle trafficking |
| 49 | GALT | Glycoprotein metabolism |
| 50 | GPI | Glycogen metabolism/Angiogenesis |
| 51 | POLD1 | DNA replication |
| 52 | RRM2 | DNA replication |

TABLE 2-continued

Unbiased survival analysis of all genes across four breast cancer datasets (Van de Vijver et al, Loi et al, Ivshina et al, Buffa et al.,). Gene expression values were divided at the median, analysed in relation to overall survival using the log rank test, and ranked in order of prognostic power.

| Rank | Gene | Function |
|---|---|---|
| 53 | MYB | Proliferation/Differentiation |
| 54 | CDC20 | Cell cycle |
| 55 | SERPINH1 | Inflammatory response/Protolysis |
| 56 | SERPINA3 | Proteolysis |
| 57 | HMMR | Cell motility |
| 58 | PDCD4 | Invasion/Apoptosis |
| 59 | PGK1 | Glucose metabolism |
| 60 | RQCD1 | Cell differentiation |
| 61 | NDRG1 | Stress response/Apoptosis |
| 62 | SLU7 | mRNA splicing |
| 63 | ESR1 | Oncotype Dx ® (Hormone Response) |
| 64 | SPARCL1 | Cell migration/Invasion |
| 65 | NME5 | Anti-apoptosis |
| 66 | BTG2 | Anti-proliferative |
| 67 | WDR5 | Histone modification |
| 68 | HMGCL | Ketogenesis |
| 69 | SERPINE1 | Cell migration/invasion |
| 70 | BTN2A1 | Lipid metabolism |
| 71 | CELSR2 | Cell-cell adhesion/signalling |
| 72 | PKM2 | Glucose metabolism |
| 73 | ORC1L | DNA replication |
| 74 | FANCA | DNA repair |
| 75 | FLT3 | Angiogenesis |
| 76 | TYMS | |
| 77 | SIRT1 | |
| 78 | GARS | |
| 79 | XPOT | |
| 80 | FUT8 | Protein glycosylation |
| 81 | BTD | |
| 82 | LZTFL1 | |
| 83 | STIP1 | |
| 84 | ME1 | |
| 85 | UCP2 | |
| 86 | RPL14 | |
| 87 | NP | |
| 88 | CIRBP | |
| 89 | ORC6L | |
| 90 | PSMD7 | |
| 91 | CCNE2 | |
| 92 | CENPA | |
| 93 | CDC25B | |
| 94 | *E2F1* | *Proliferation MTR* |
| 95 | CCNB1 | Proliferation (Oncotype Dx ®) |
| 96 | H2AFX | |
| 97 | RAD54L | |
| 98 | ADAMTS7 | |
| 99 | LEPR | |
| 100 | KIAA1609 | |
| 101 | KIAA1407 | |
| 102 | CCNA2 | Cell cycle |
| 103 | PFKL | |
| 104 | KIAA0999 | |
| 105 | SLC23A2 | |
| 106 | FUCA1 | |
| 107 | RFC2 | |
| 108 | CCNI | |
| 109 | NEK2 | |
| 110 | HS3ST1 | |
| 111 | DYSF | |
| 112 | AGTR1 | |
| 113 | VAV3 | |
| 114 | PDE6B | |
| 115 | POLA2 | |
| 116 | ATP5G3 | |
| 117 | KIAA0831 | |
| 118 | PTMA | |
| 119 | GSTM3 | |
| 120 | PHB | |
| 121 | MAP4K4 | |
| 122 | PGR | Oncotype Dx ® (Hormone Response) |
| 123 | BCL2 | Oncotype Dx ® (Anti-apoptosis) |
| 124 | IGFBP4 | |
| 125 | CENPE | |
| 126 | CYC1 | |
| 127 | CDO1 | |
| 128 | MYCBP | |
| 129 | SKP2 | |
| 130 | RAB3D | |
| 131 | DHCR7 | |
| 132 | KIAA1324 | |
| 133 | ATP11A | |
| 134 | BECN1 | |
| 135 | HDGF | |
| 136 | PCYT1A | |
| 137 | TNNC1 | |
| 138 | CENPF | |
| 139 | ADCY1 | ATP metabolism |
| 140 | MKI67 | Oncotype Dx ® (Proliferation) |
| 141 | KIAA0101 | |
| 142 | KCNN3 | |
| 143 | SLC19A1 | |
| 144 | EPHA4 | Cell adhesion/signalling/migration/invasion |
| 145 | CDC25C | |
| 146 | NFATC1 | |
| 147 | PDE5A | |
| 148 | ABCF1 | |
| 149 | CKS2 | |
| 150 | PRRG2 | CalciumVitamin K signalling |
| 151 | CLDN4 | Cell adhesion |
| 152 | GTSE1 | |
| 153 | RAI2 | |
| 154 | PRLR | Hormone signalling |
| 155 | SEMA7A | |
| 156 | CPT1A | |
| 157 | PDHA1 | |
| 158 | RAB27B | |
| 159 | MCM2 | |
| 160 | FLNB | |
| 161 | SLC2A3 | Glucose transport/metabolism |
| 162 | IMPDH2 | |
| 163 | *HMGB2* | *Proliferation MTR* |
| 164 | HOXB13 | Homeobox protein |
| 165 | NFRKB | |
| 166 | RPS6KA5 | |
| 167 | CRIP2 | |
| 168 | BTF3 | |
| 169 | MAGED1 | |
| 170 | NAPG | |
| 171 | ASNS | |
| 172 | PTTG2 | |
| 173 | TPST1 | Wound response |
| 174 | RPLP1 | |
| 175 | GLTSCR2 | |
| 176 | PLA2R1 | |
| 177 | POLQ | |
| 178 | CSTB | |
| 179 | CALU | Calcium-dependent signalling |
| 180 | PPARD | |
| 181 | TXN | |
| 182 | NAT1 | |
| 183 | MYO7A | |
| 184 | EIF4G1 | |
| 185 | SHMT2 | |
| 186 | PTDSS1 | |
| 187 | LHX2 | |
| 188 | PLA2G10 | |
| 189 | ANLN | |
| 190 | ATP5J | |
| 191 | POLR2D | |
| 192 | SERF1A | |
| 193 | EPHB4 | |
| 194 | CDC23 | |
| 195 | PTPN14 | |
| 196 | PEX12 | |

TABLE 2-continued

Unbiased survival analysis of all genes across four breast cancer datasets (Van de Vijver et al, Loi et al, Ivshina et al, Buffa et al.,). Gene expression values were divided at the median, analysed in relation to overall survival using the log rank test, and ranked in order of prognostic power.

| Rank | Gene | Function |
|------|------|----------|
| 197 | PPP1R11 | |
| 198 | CSPG5 | |
| 199 | DONSON | |
| 200 | CTSL2 | Oncotype Dx ® (Invasion) |

(italics = MTRs; bold = conventional clinical biomarkers) OncoMasTR pathway genes include: IGBP1; LRP2; PDZK1; TXNRD1; GATA3; ADM; CAMLG; SERPINA3; NDRG1; SERPINE1; FLT3; FUT8; ADCY1; EPHA4; PRRG2; CLDN4; PRLR; SLC2A3; HOXB13; TPST1; and CALU.

Proliferative MTRs are Excellent Predictors of Breast Cancer Prognosis on the RNA and Protein Levels.

Figure 3A:
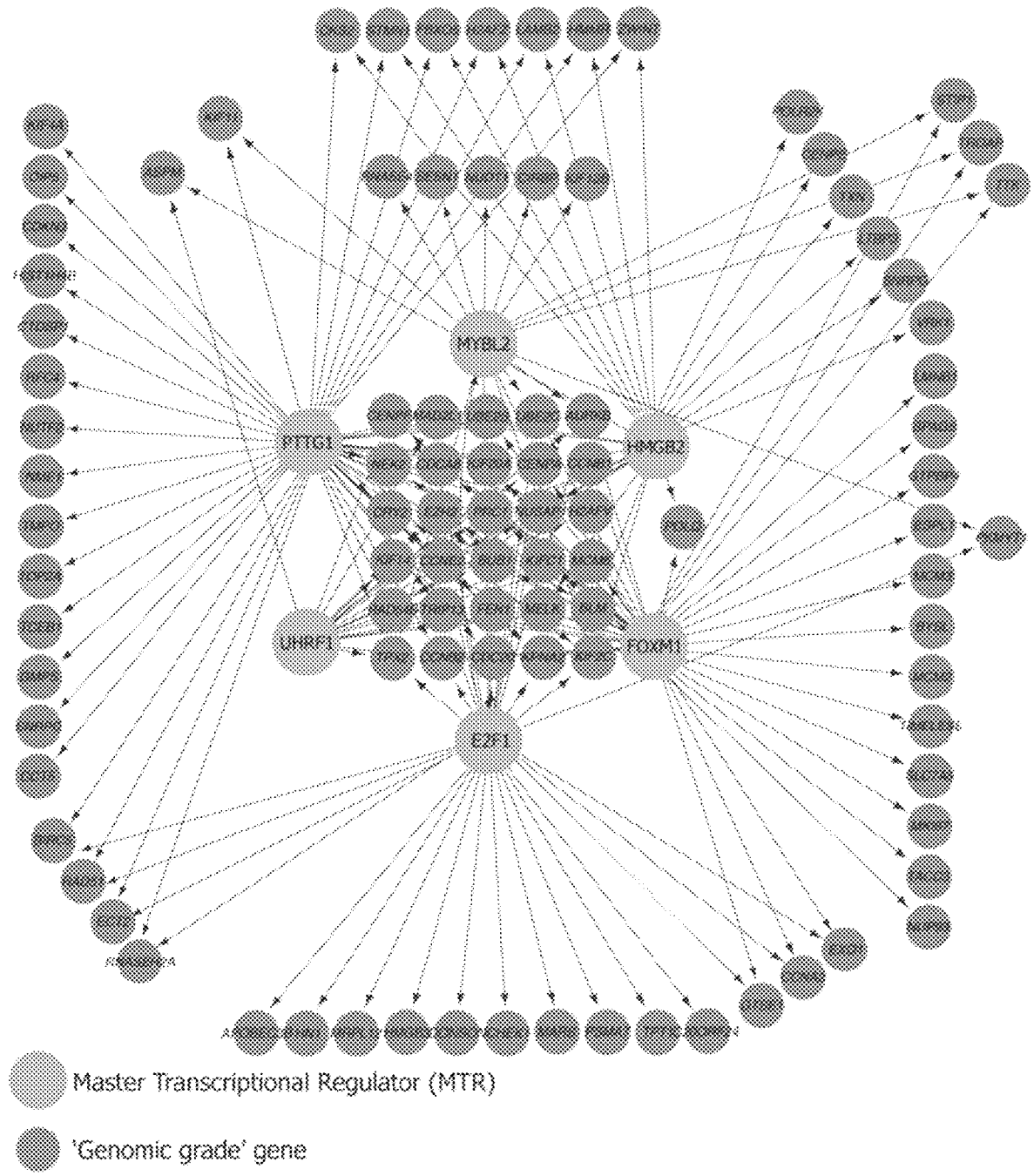
FIGS. 3A-3E illustrate that master transcriptional regulators predict patient outcome.

Next, the potential clinical significance of the MTRs as prognostic markers in breast cancer was explored. The applicant began by performing an unbiased ARACNe analysis of the MammaPrint and Genomic Grade signatures, both of which have been shown to predict clinical outcome in breast cancer patients (Sotiriou et al., 2006; van't Veer et al., 2002). Remarkably, across the three independent datasets analysed (ExPO; Loi et al., 2007; van de Vijver et al., 2002), FOXM1, E2F1, MYBL2, UHRF1, PTTG1, HMGB2, ATAD2, E2F8, ZNF367, and TCF19 were predicted to be among the top upstream regulators of both 'poor prognosis' signatures (FIG. 3A and Table 1). This suggests that these MTRs directly regulate the expression of many genes within both the MammaPrint and Genomic Grade prognostic signatures.

Figure 3B:
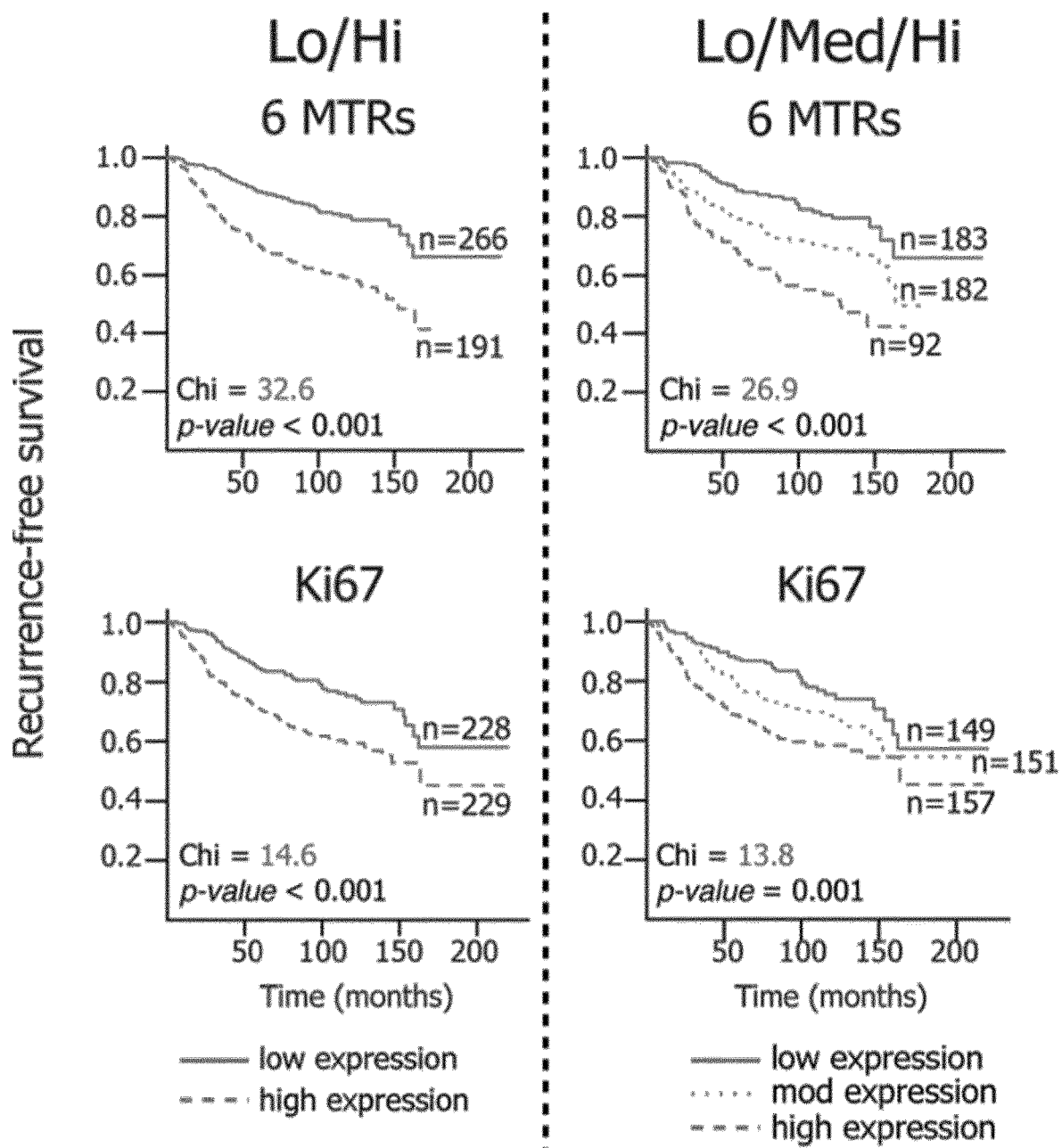
Figure 9:
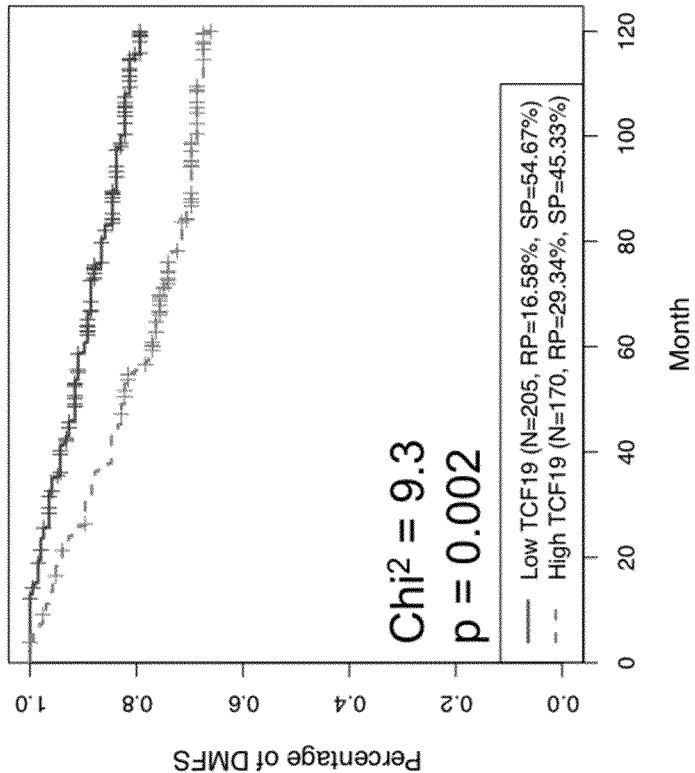
FIG. 9 illustrates the prognostic value of additional MTRs—ATAD2 and TCF19. Kaplan-Meier survival curves demonstrating the prognostic value of ATAD2 and TCF19 within ER-positive, lymph-node negative patients in the combined microarray dataset (n=375), in terms of distant metastasis-free survival, censored at 10 years. The gene expression values for ATAD2 and TCF19 were split into low/high groups by the median within each of the three datasets. There are no probes mapping to E2F8 and ZNF367 in the NKI dataset.
Figure 9:
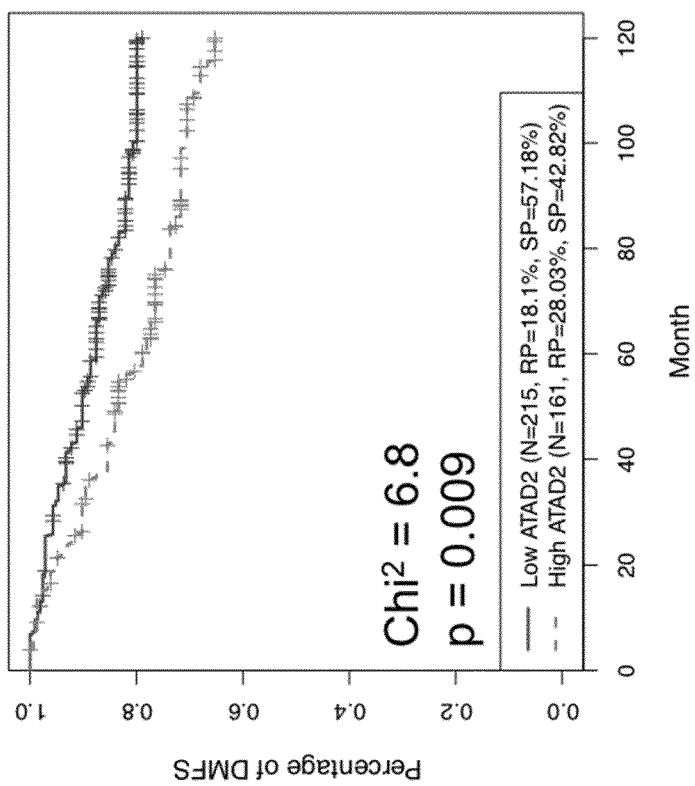

The applicant next wished to explore the possibility that the MTRs may themselves be reliable predictors of poor prognosis. The association of each individual MTR with patient survival was examined in a combined dataset of three published microarray studies representing the genome-wide mRNA expression of 457 lymph node-negative breast tumours untreated by chemotherapy (Loi et al., 2007; Miller et al., 2005; van de Vijver et al., 2002). This revealed that high mRNA expression levels of any of FOXM1, E2F1, MYBL2, UHRF1, PTTG1, HMGB2 in breast tumours was significantly associated with reduced recurrence-free survival time, and a combination of all six MTRs was more powerful at stratifying the patients compared to any MTR alone (FIG. 3B). Significantly, using either a low/high or a low/moderate/high categorisation strategy, the six MTR combination was better at predicting recurrence-free survival than the established proliferation marker Ki67 (FIG. 3B). These six MTRs now form the 'core' panel of the method or assay of the present invention, also called the OncoMasTR assay. High mRNA expression levels of ATAD2 and TCF19 in breast tumours was also significantly associated with reduced recurrence-free survival time in this cohort (FIG. 9). Expression information was not available in this cohort for E2F8 and ZNF367.

Figure 3C:
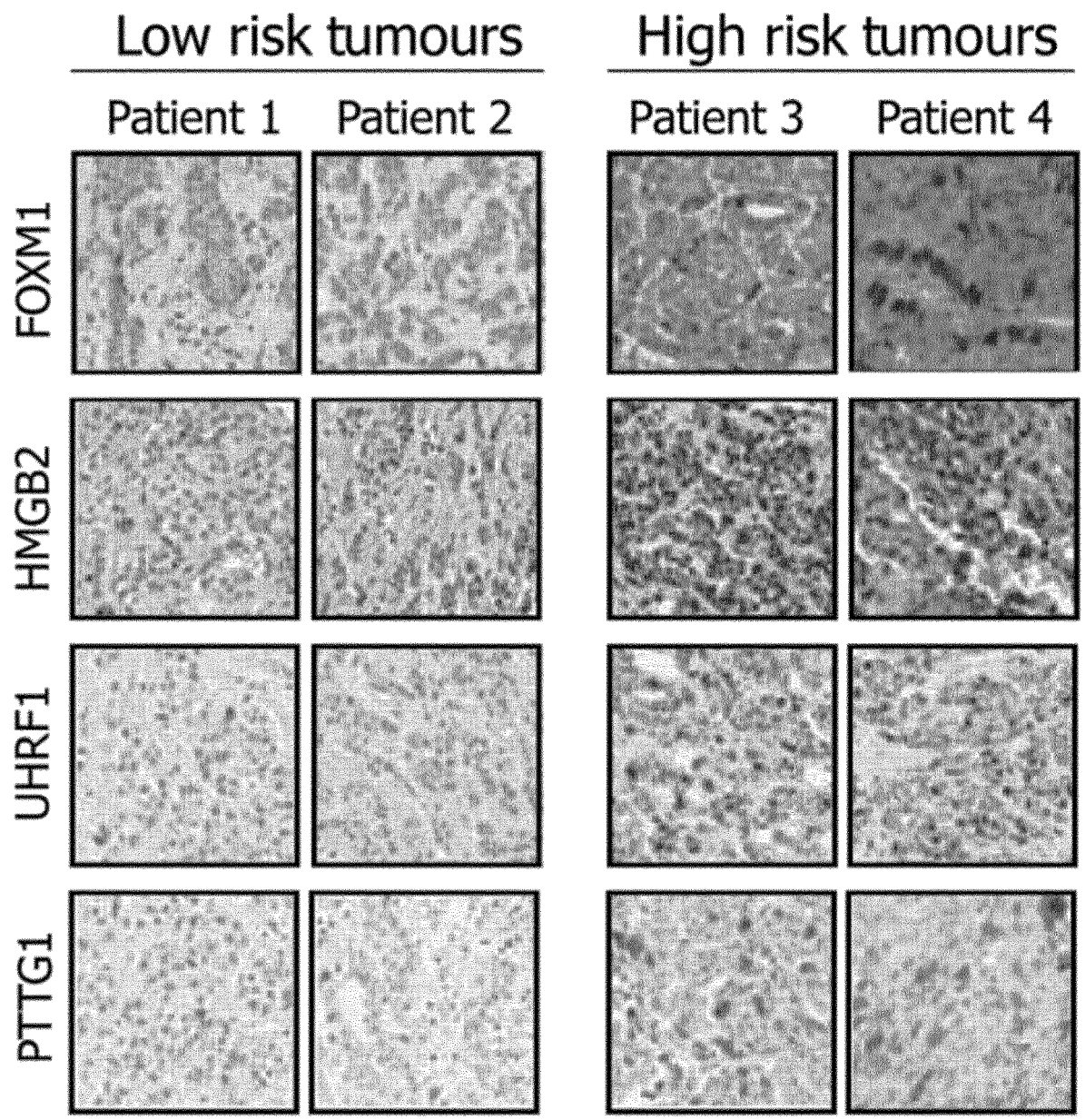
Figure 3D:
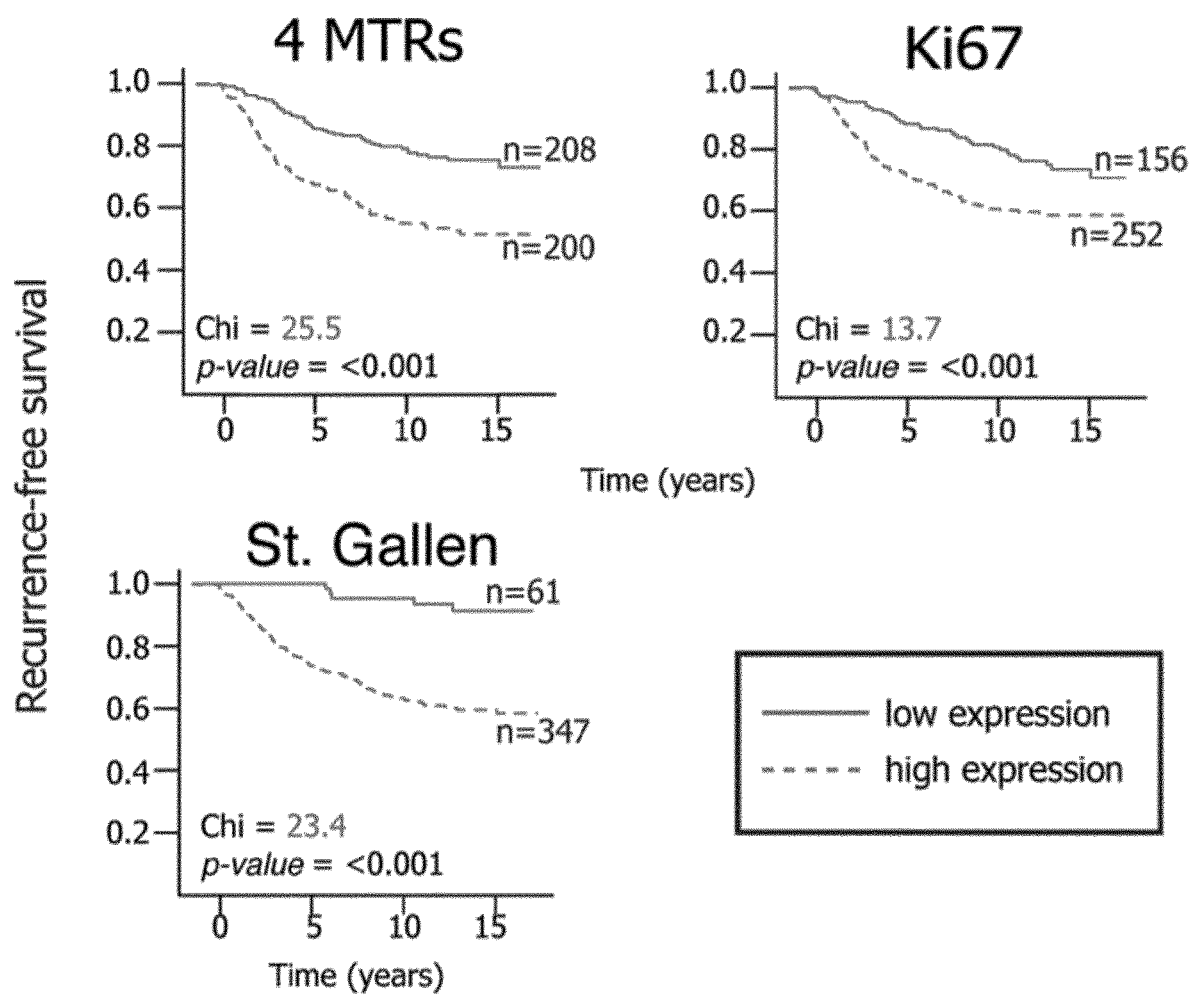
Figure 3E:
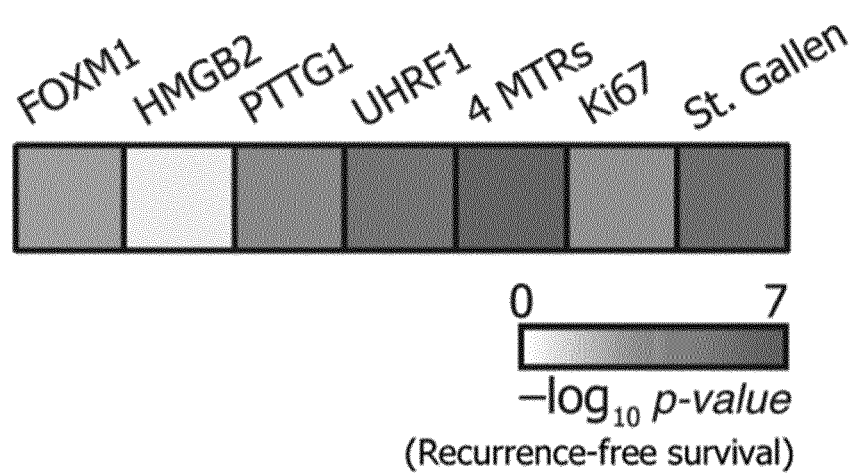

Next, the protein levels of the MTRs were examined in an independent breast cancer patient cohort via immunohistochemistry (IHC). Antibodies were screened for all 6 MTRs and four identified that specifically recognised FOXM1, HMGB2, PTTG1 and UHRF1. Tissue microarrays (TMAs) representing 512 invasive breast tumours were evaluated for the protein levels of each of these MTRs (FIG. 3C). The stained TMAs were manually scored and the results analysed in relation to recurrence-free survival for the 430 tumours with information on all four MTRs (FIG. 3D). Each MTR was individually associated with poor prognosis, and the combination of all four MTRs was more powerful at stratifying the patients in relation to survival, compared to existing prognostic indicators such as Ki67 or the St. Gallen criteria, a prognostic index based on age, nodal status, tumour size, ER/PR status and tumour grade (Goldhirsch et al., 2001) (FIG. 3D). The results from this Kaplan-Meier analysis were also represented in a heat-map format to indicate the strength of the association with recurrence-free survival (FIG. 3E). To the knowledge of the inventors, this heat-map arrangement has not been previously used to present large-scale survival analysis, and provides an intuitive way of determining the best prognostic combination in any particular dataset.

To further refine the prediction method of the claimed invention and complement the approach taken by the Applicant, the other crucial pathways, besides proliferation control, involved in breast cancer progression were taken into account. Additional genes from the unbiased analysis of four independent breast cancer datasets (described above and in Table 2) were selected, which strongly correlate with survival, and represent other aspects of tumour progression as distinct from proliferation, such as migration/invasion, apoptosis and hormone signalling pathways (Table 3). When combined with the proliferation MTRs, these genes add a further layer of information, and increase the predictive power of the gene combination even further. These genes form the basis of the OncoMasTR pathway panel which, when combined with the OncoMasTR core genes, further improve the prognostic power of the method.

TABLE 3

Summary of OncoMasTR Core and Pathway gene panels

| OncoMasTR Core Panel Proliferation | OncoMasTR Pathway panel | | | |
|---|---|---|---|---|
| | Migration/ Invasion | Apoptosis | Hormone/ Growth Factor signalling | Other function |
| UHRF1 FOXM1 MYBL2 PTTG1 E2F1 HMGB2 | EPHA4 HOXB13 CLDN4 SERPINE1 | BIRC5 BCL2 TXNRD1 NDRG1 | CAMLG PRLR ADM PRRG2 | IGBP1 FUT8 CALU ADCY1 |
| | Estrogen signalling | Inflammation/Wound response | Angiogenesis | Metabolic pathways |
| | GATA3 PDZK1 | TPST1 SERPINA3 | FLT3 | SLC2A3 LRP2 |

Figure 4A:
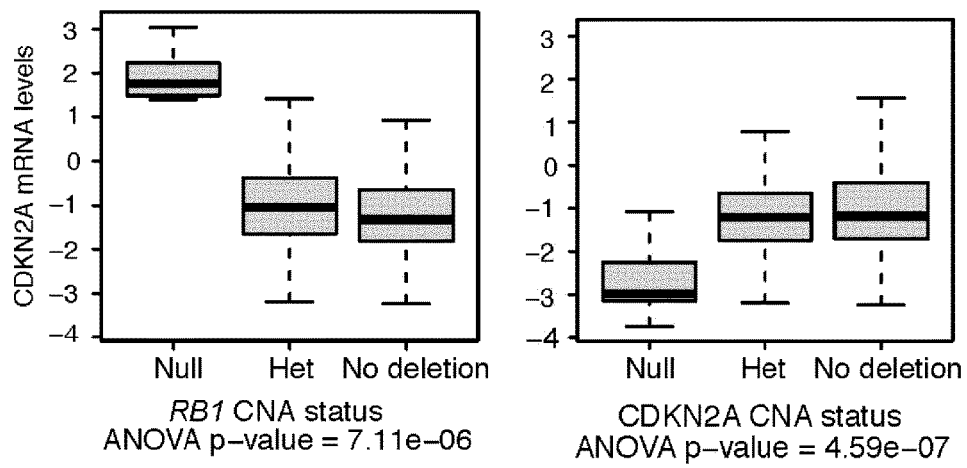
FIGS. 4A-4E illustrates that absent and high CDKN2A mRNA and p16 protein levels predict poor prognosis in breast cancer.
Figure 4B:
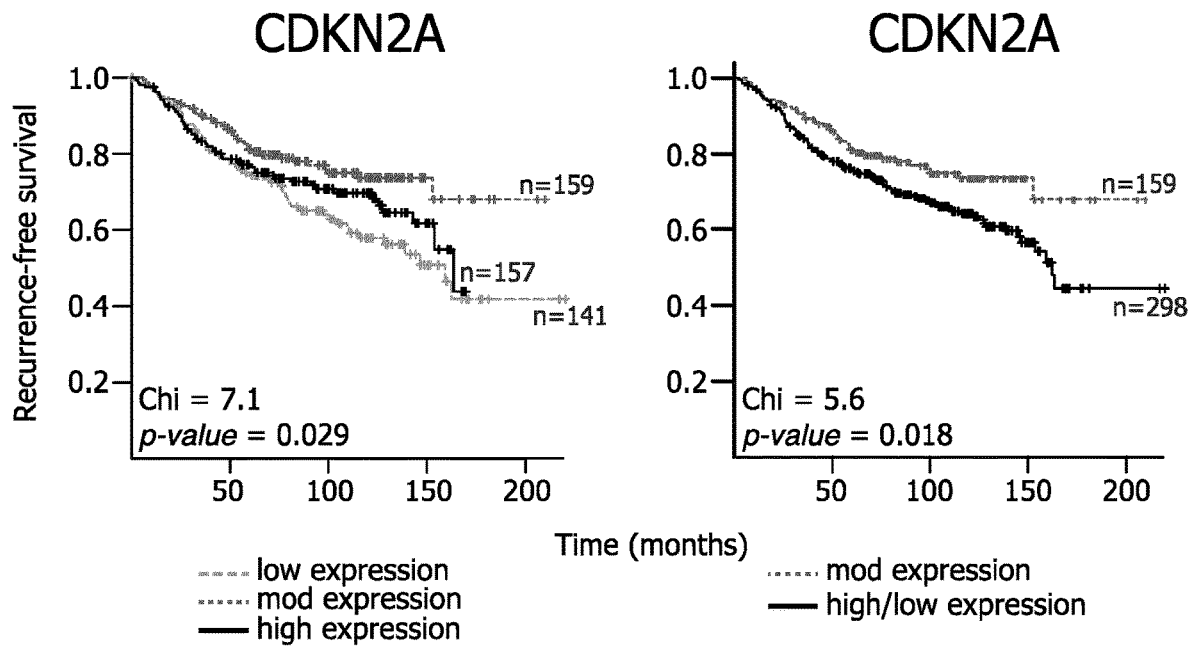
Figure 4C:
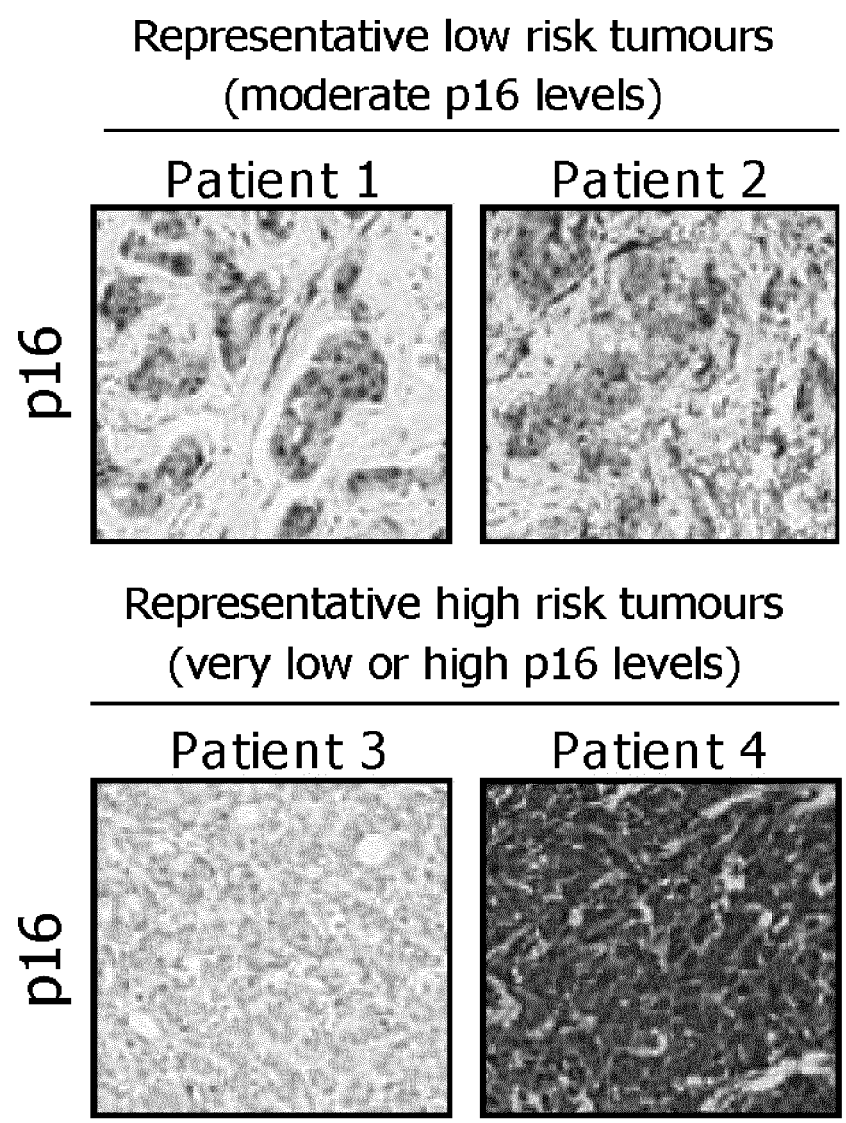
Figure 4D:
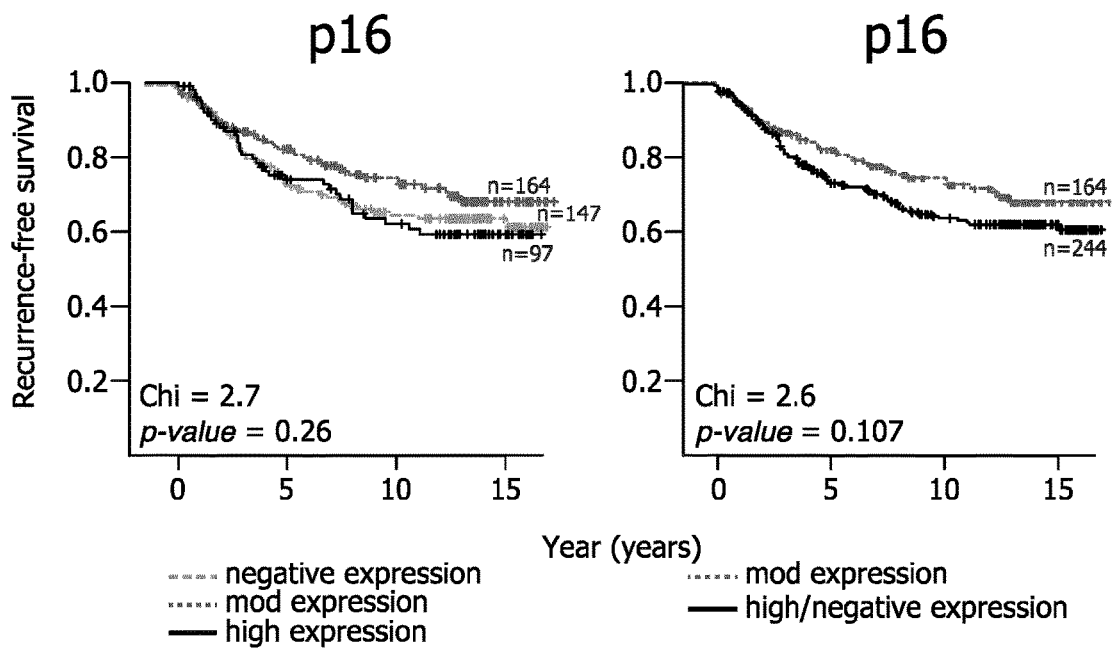
Figure 4E:
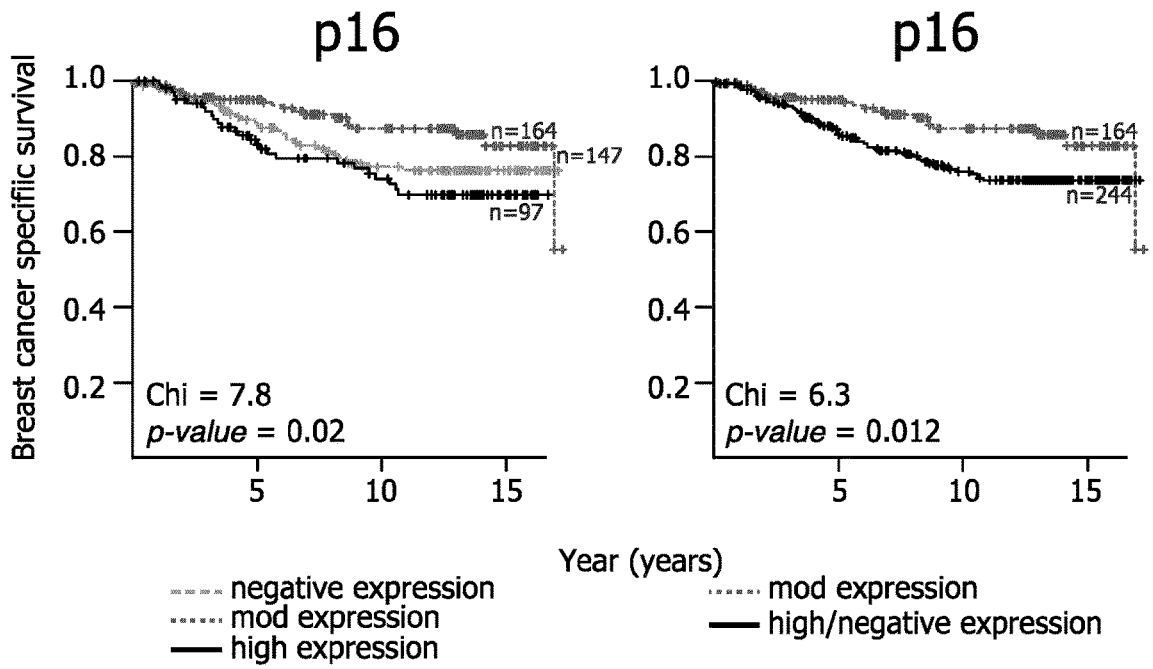

Disruption of Cellular Senescence Pathways can be Inferred Using a Combination of MTRs and $p16^{INK4A}$ Levels and is a Strong Predictor of Poor Outcome in Breast Cancer The applicant next wished to examine if the levels of $p16^{INK4A}$, a potential proxy for bypass of the cellular senescence checkpoint in cancer, could add to the prognostic power of the MTRs. First, to confirm that deregulated CDKN2A mRNA levels correlated with genetic perturbation of the cellular senescence checkpoint, The Cancer Genome Atlas (TCGA) breast cancer dataset (Cancer Genome Atlas, 2012) was analysed, and found that high levels of CDKN2A mRNA levels correlated with deletion of RB1, as previously reported in other studies (Hara et al., 1996; Kotake et al., 2007; Li et al., 1994; Tam et al., 1994), while deletion of CDKN2A correlated with decreased mRNA levels (FIG. 4A). Strikingly, moderate mRNA levels of INK4A were found to correlate with improved recurrence-free survival in 457 lymph node-negative breast cancer patients, while either very low or very high levels correlated with shorter recurrence-free survival (Loi et al., 2007; Miller et al., 2005; van de Vijver et al., 2002) (FIG. 4B). The applicant next performed IHC for the p16$^{INK4A}$ protein on the same breast cancer TMAs used previously (FIG. 4C). This confirmed that either very high or very low p16$^{INK4A}$ protein levels also correlated with both shorter recurrence free and breast cancer-specific survival, whereas moderate levels correlated with extended survival (FIG. 4D-4E).

Based on these observations, the applicant reasoned that the breast cancers with either very high or very low p16$^{INK4A}$ protein levels had bypassed the cellular senescence checkpoint, and this could potentially explain their poor prognosis. The breast cancers with low p16$^{INK4A}$ protein levels were most likely to have a deletion in the INK4A gene locus, while those with aberrantly high levels likely had mutations in the INK4A gene or deregulation of downstream E2F-pRB pathway members such as Cyclin D1 or pRB. In contrast, the tumors with moderate expression of INK4A were most likely enriched in cells that had not bypassed the cellular senescence checkpoint and, therefore, had a more favourable prognosis.

Previous studies of p16$^{INK4A}$ expression in relation to breast cancer prognosis have reported conflicting results—while p16$^{INK4A}$ was found to be associated with poor prognosis in some cohorts (Hui et al., 2000; Milde-Langosch et al., 2001), other studies showed an association with improved outcome (Peurala et al., 2013). These studies have generally split expression values into two groups, low/negative and high, for analysis. However, based on what is known of the biology of p16$^{INK4A}$ and the p16-Rb pathway in cancer, the Applicant proposes that the best approach may be to examine p16$^{INK4A}$ expression in three groups, low/negative, moderate and high expression. This may separate tumors which are likely to have deleted or inactivated p16$^{INK4A}$ (low expressers) and those which have aberrantly high levels of p16$^{INK4A}$ and are likely to have a dysregulated p16-Rb pathway (high expressers) from the tumors with a functioning senescence response (moderate expressers).

A Combination of Measuring Proliferative MTRs and p16$^{INK4A}$ Levels (OncoMasTR Score) Outperforms Currently Used Approaches for Predicting Breast Cancer Prognosis.

Figure 5A:
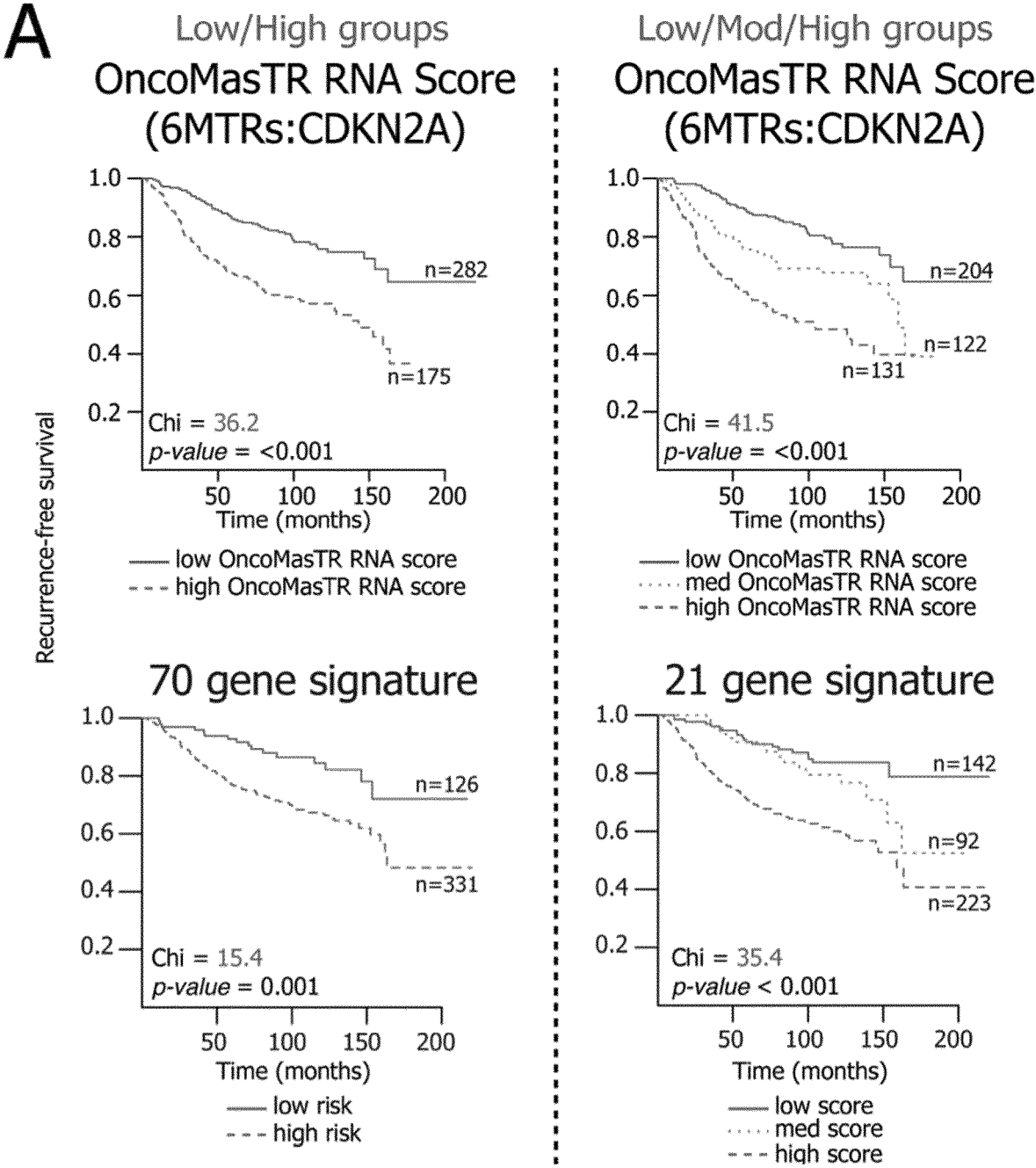
FIGS. 5A-5D illustrate that combined measurements of MTR and p16(INK4A) levels outperforms estimates of currently used strategies.
Figure 5B:
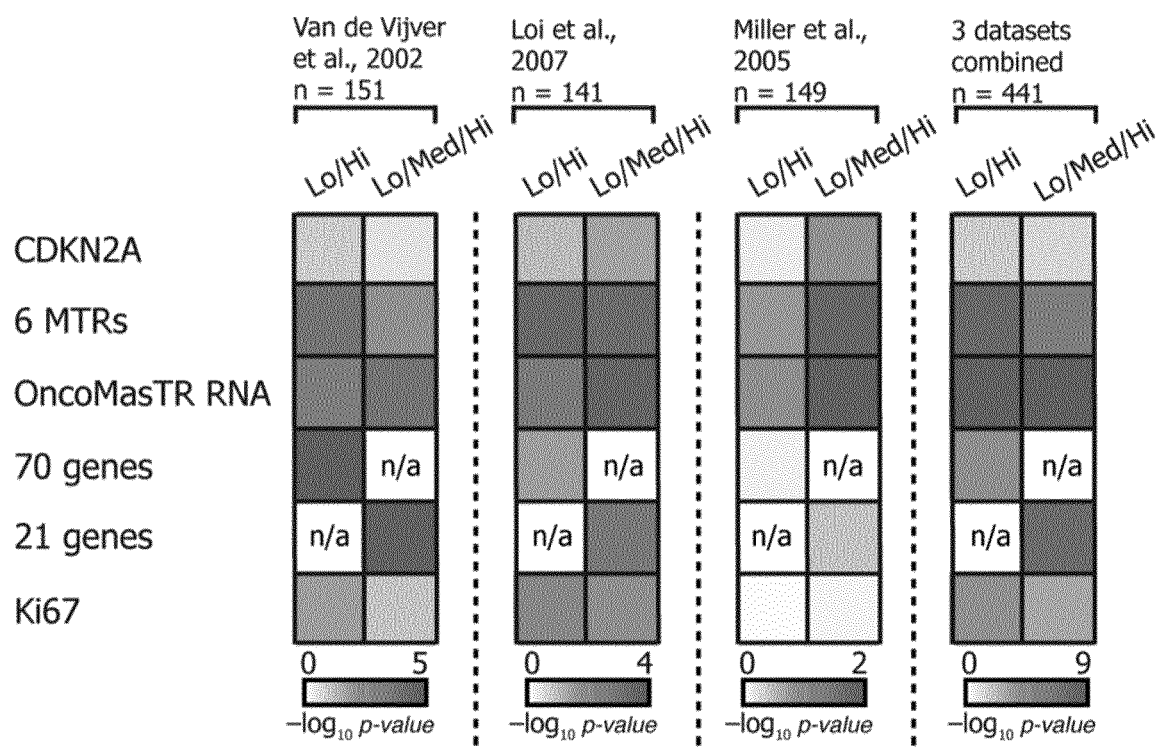

The prognostic ability of a combination of p16$^{INK4A}$ and the proliferative MTRs were evaluated next. To do this, a score encompassing both proliferative MTRs and p16$^{INK4A}$ expression was developed, termed the 'OncoMasTR RNA score', and compared with estimates of other leading multi-gene prognostic assays (FIG. 5A). This revealed that the OncoMasTR RNA score compared favourably to surrogate estimations of the MammaPrint™ and OncotypeDx® signatures, using low/high categories for comparison with MammaPrint™, and low/moderate/high categories for comparison with Oncotype Dx®. In order to further demonstrate the prognostic capability of the OncoMasTR RNA score, the applicant analysed each individual dataset and the combined dataset, and represented the results in a heat-map format (FIG. 5B). This extended analysis revealed that, while the MammaPrint™ 70-gene signature performed best in the dataset which included samples used in its derivation (van't Veer et al., 2002; van de Vijver et al., 2002), the OncoMasTR RNA score outperformed estimates of both the MammaPrint™ and Oncotype Dx® assays overall when all three datasets were combined.

Figure 5C:
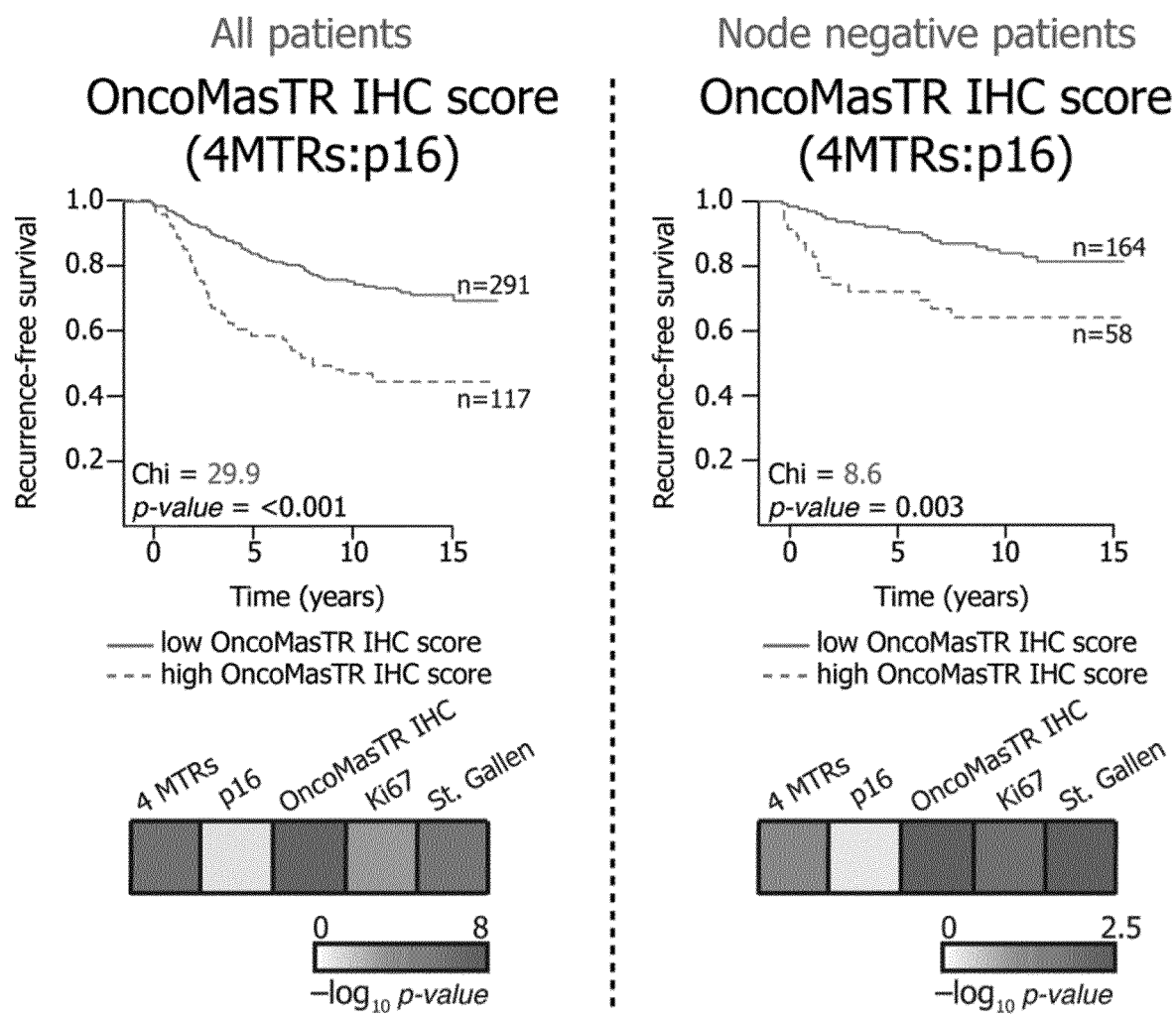
Figure 5D:
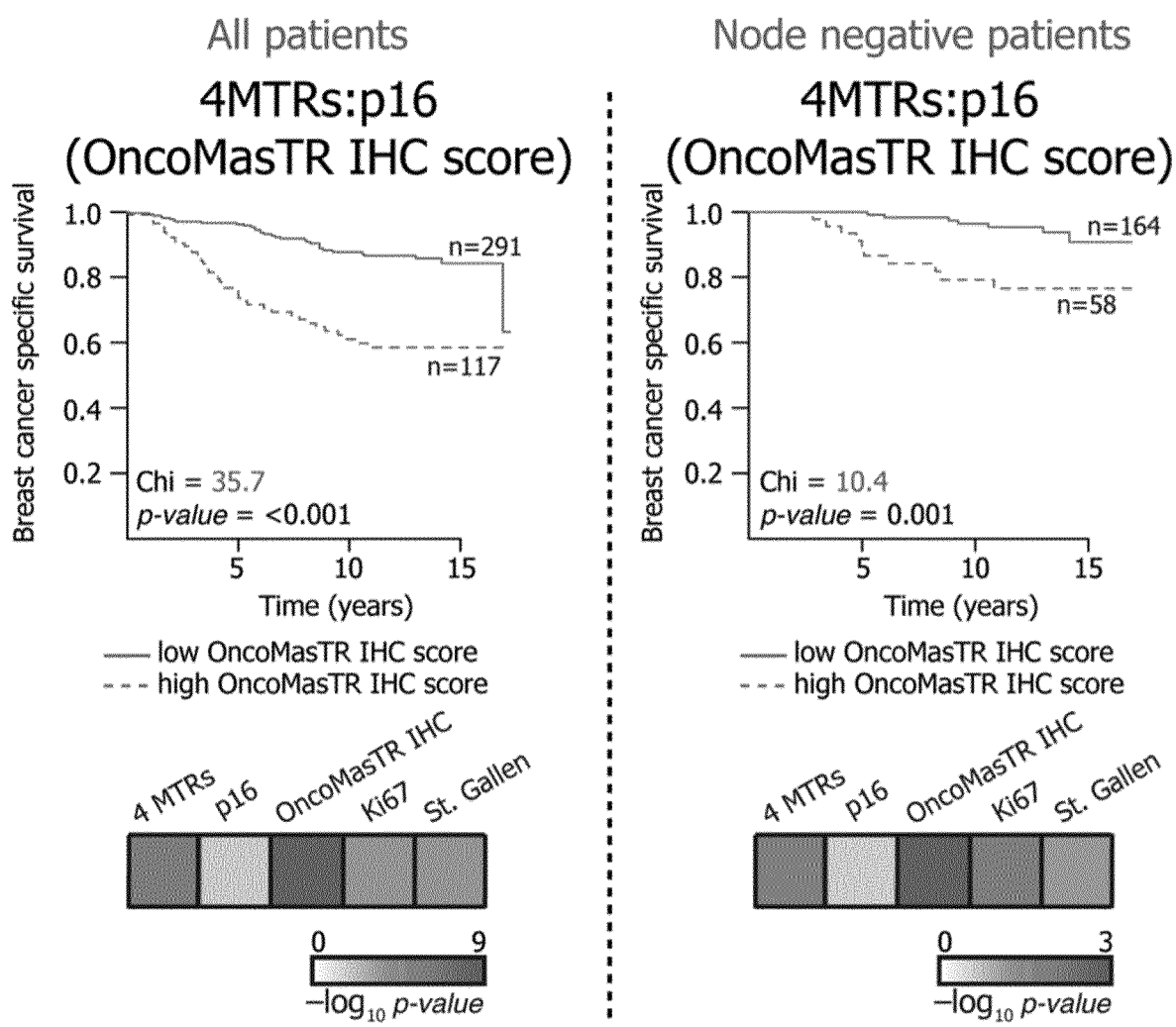

Next, to validate these observations at the protein level, the applicant combined the p16$^{INK4A}$ protein and the IHC-based 4-MTR panel, called the 'OncoMasTR IHC score', and tested this combination in all patients and in lymph node-negative patients, in relation to both recurrence-free survival (FIG. 5C) and breast cancer-specific survival (FIG. 5D). This revealed that when p16$^{INK4A}$ is added to the IHC-based MTR panel, the combination of high levels of proliferative MTR proteins and either low or aberrantly high p16$^{INK4A}$ protein was strongly associated with poor prognosis, and there was a striking improvement in the ability to predict patient survival in comparison to the four MTRs without p16$^{INK4A}$, either on all patients (FIG. 5C) or on a lymph node-negative sub-cohort (FIG. 5D).

Figure 6A:
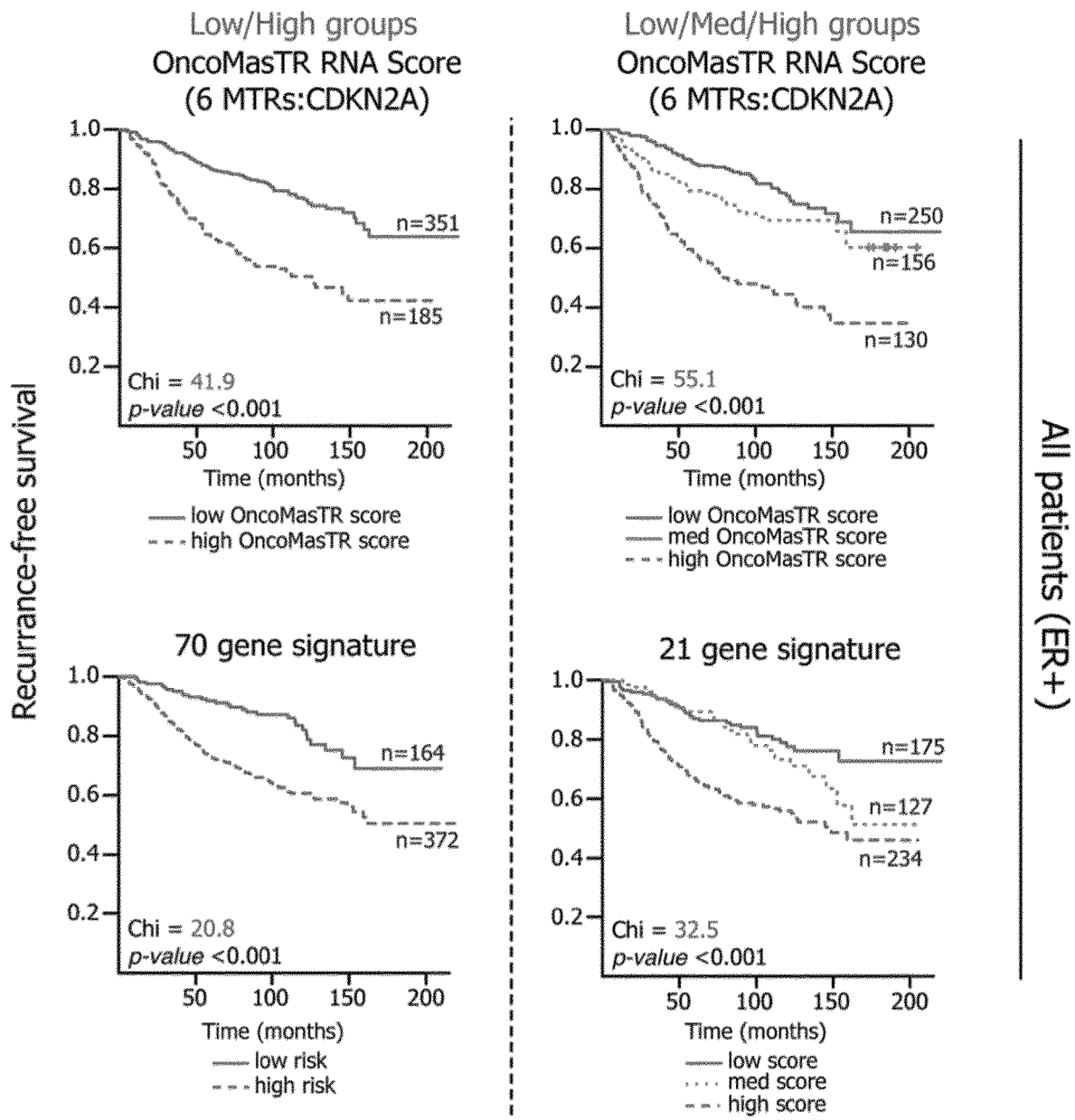
FIGS. 6A-6B illustrate the performance of the OncoMasTR RNA score in ER-positive patients.
Figure 6B:
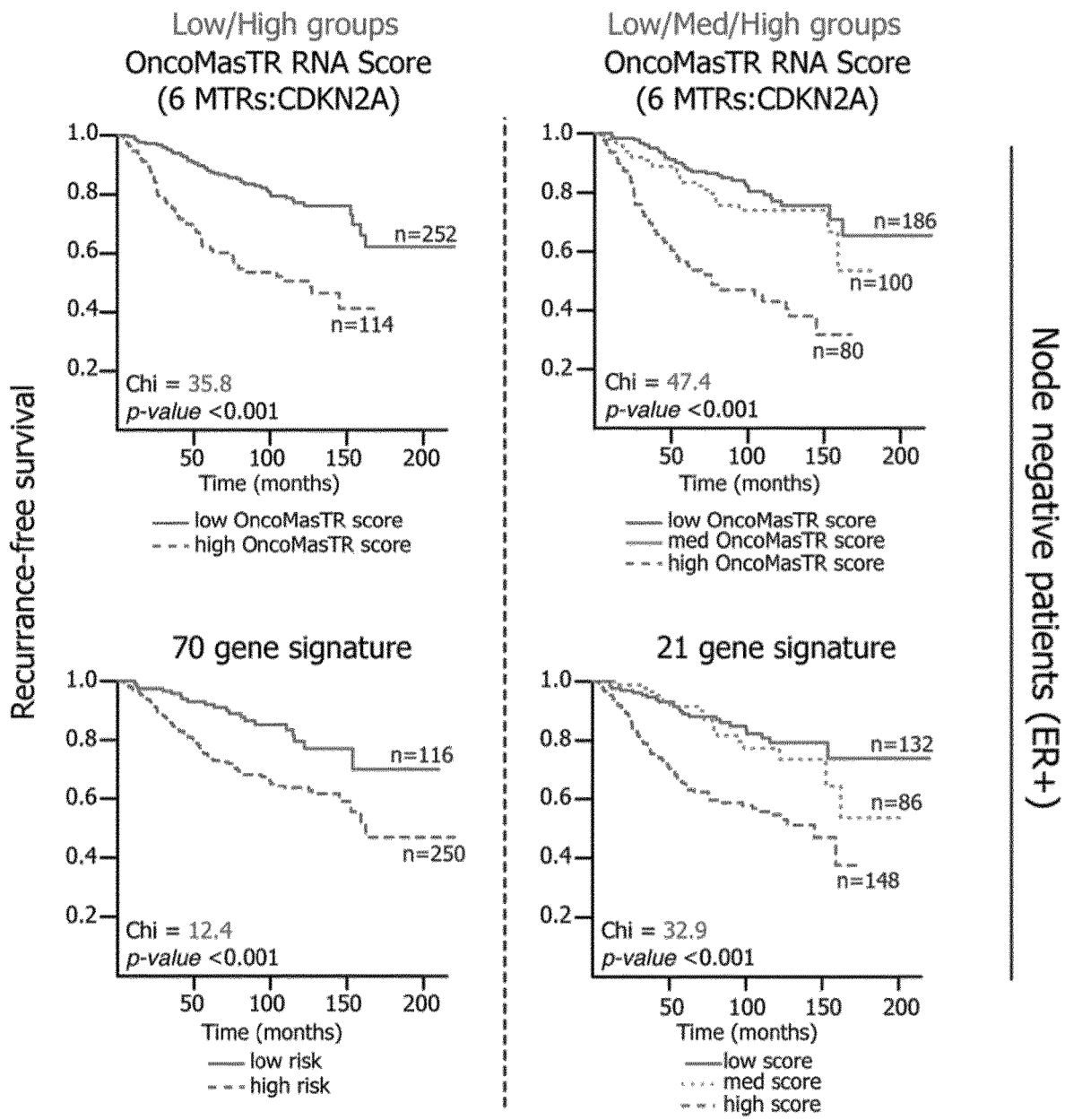
Figure 7:
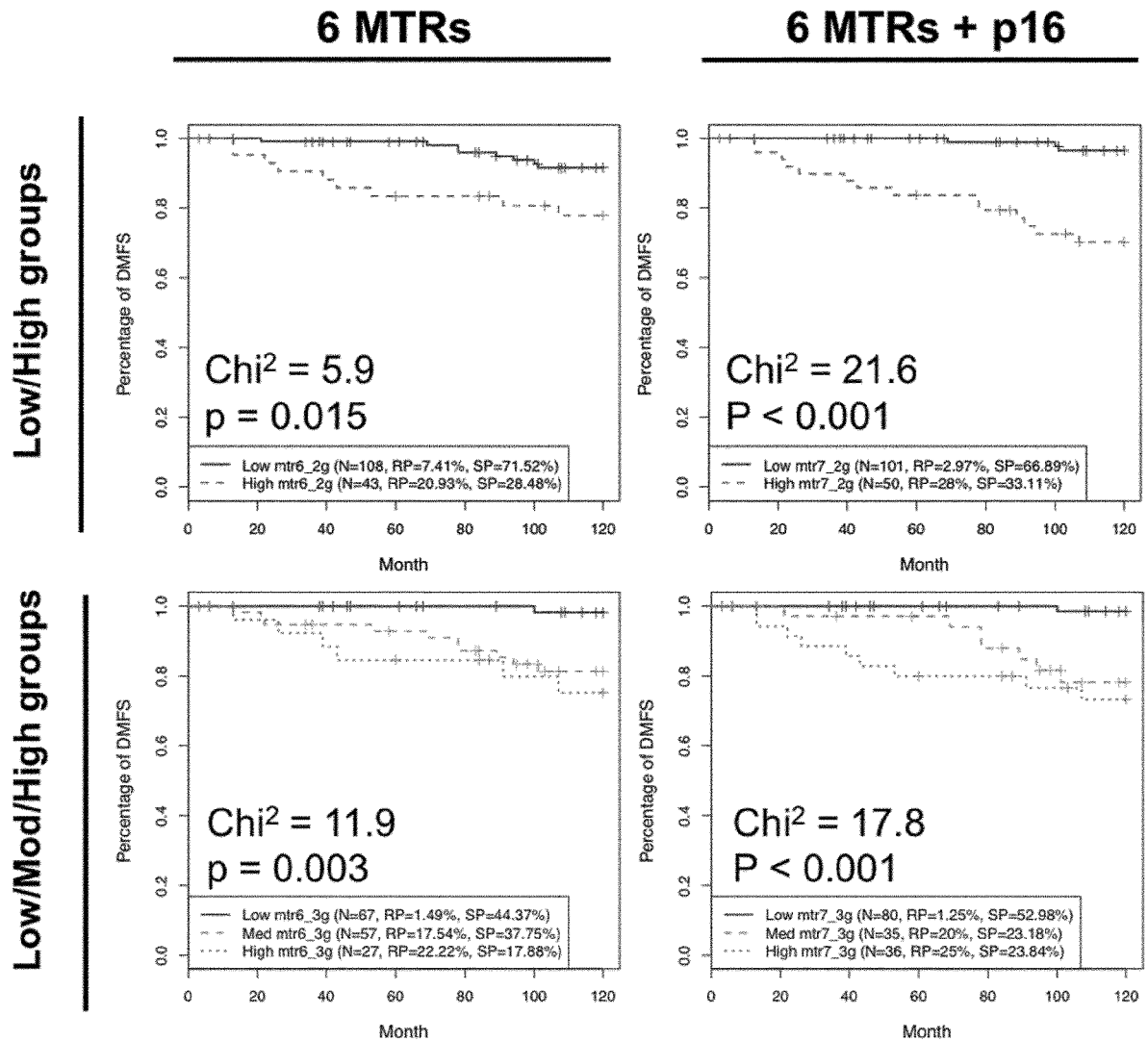
FIG. 7 illustrates the performance of the OncoMasTR RNA score as measured by Taqman qRT-PCR. Kaplan-Meier survival curves demonstrating the prognostic value of the OncoMasTR RNA score (4 MTRs+/−CDKN2A) as indicated in ER-positive, lymph-node negative patients in the NKI dataset who did not receive adjuvant chemotherapy (n=151), in terms of distant metastasis-free survival. Patients were divided into Low and High risk groups, and Low, Moderate and High risk groups as indicated. To do this, expression data for each MTR gene was used to split patients into low/high groups at the median. The sum of the 6 MTR (+/−CDKN2A) were taken and further split by median (2 groups) or by 33th and 66th percentile (3 groups). The end point is DMFS (censored at 10 years).
Figure 8:
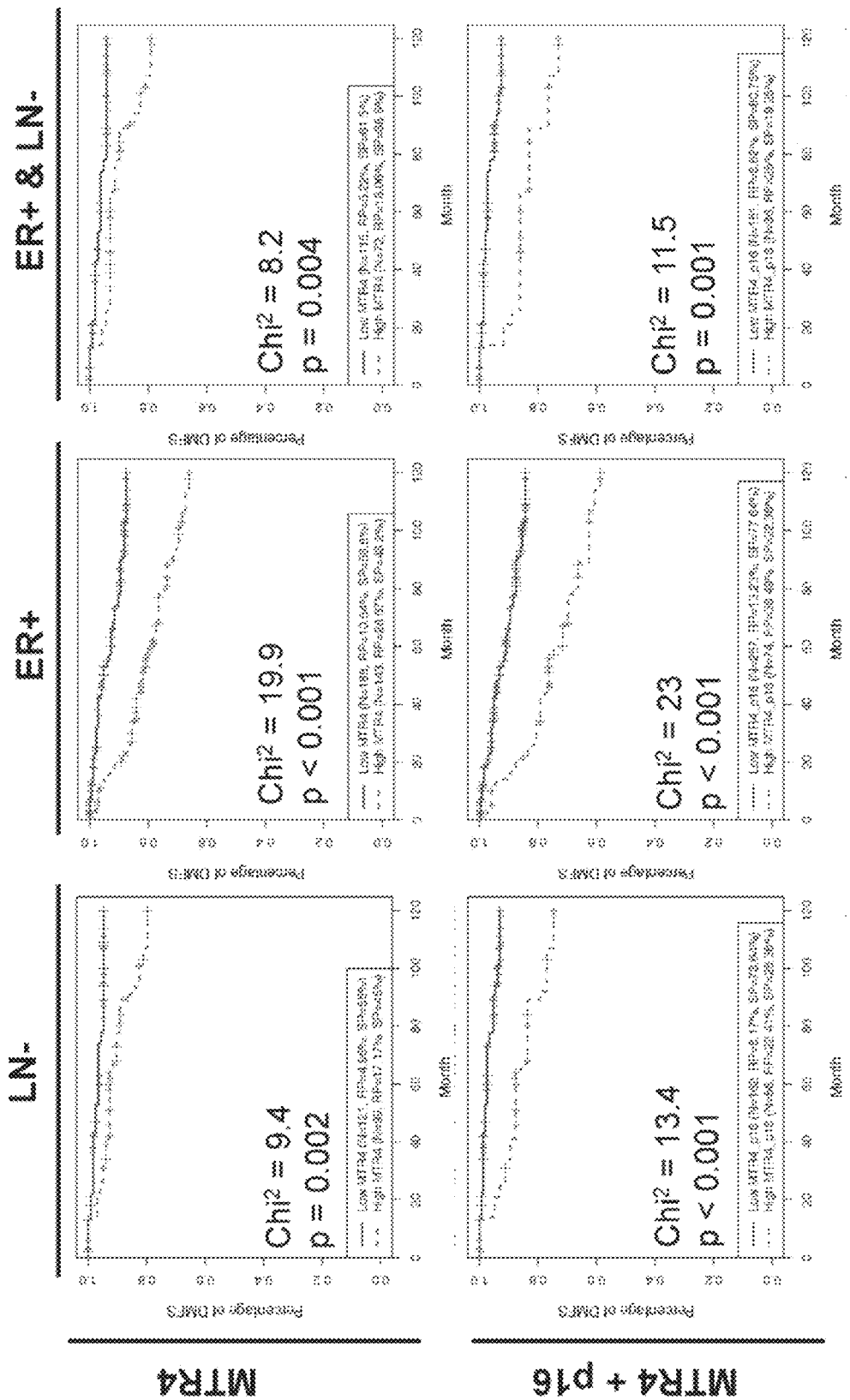
FIG. 8 illustrates the performance of the OncoMasTR IHC score in terms of Distant Metastasis-free survival. Kaplan-Meier survival curves demonstrating the prognostic value of the OncoMasTR IHC score (4 MTRs+/−CDKN2A) as indicated in lymph-node negative patients (LN−) (n=220), ER-positive patients (ER+) (n=331), and LN-ER+ patients (n=187), who did not receive adjuvant chemotherapy, in terms of distant metastasis-free survival.

The OncoMasTR RNA Score Outperforms Surrogate Estimates of MammaPrint™ and Oncotype Dx® in ER-Positive Patients In order to further evaluate the potential clinical utility of the OncoMasTR RNA score, its prognostic power was examined in 366 ER-positive, lymph node-negative patients, which reflects the inclusion criteria for the Oncotype Dx® assay. The OncoMasTR RNA score outperformed surrogate estimates of both the MammaPrint™ (low/high groups), and Oncotype Dx® (low/mod/high groups) assays in both the entire cohort (FIG. 6A), and lymph node-negative patient cohort (FIG. 6B). The OncoMasTR RNA score was also assessed using a Taqman® qRT-PCR approach in 151 ER-positive, lymph node-negative patients using DMFS as an endpoint, matched to the cohort used for IHC validation (FIG. 7). This demonstrated that the OncoMasTR RNA score, when measured by Taqman® qRT-PCR analysis, showed analogous performance to the microarray-based analysis. Furthermore, the OncoMasTR IHC score also demonstrated utility in this group of patients, using either recurrence-free survival, or distant metastasis-free survival (FIG. 8) as an endpoint.

The OncoMasTR Score has Independent Prognostic Value in all Patients and Lymph Node-Negative Patients Next, in order to determine if the MTR and INK4A/p16$^{INK4A}$ combination can provide additional prognostic information independent of standard clinicopathological variables, the applicant performed multivariate analysis using Cox proportional hazards models. The OncoMasTR score was found to contribute added prognostic information to a standard clinicopathological variable model, in terms of recurrence-free survival, at both mRNA (Table 4) and protein (Table 5) levels. This was also observed in the lymph node-negative patient cohort. The added prognostic value of the OncoMasTR score on top of the standard clinical model is superior to all other prognostic indicators, including Ki67, the 70-gene signature (MammaPrint™) and the 21-gene signature (Oncotype Dx®). Furthermore, the OncoMasTR RNA score was found to provide significant additional prognostic information to a model comprising the standard clinical variables together with the Oncotype Dx® surrogate estimation.

TABLE 4

Multi-variate Cox regression analysis using a standard clinical variable model* in the combined microarray datasets

|  | Variable | All patients (n = 567) | | Node negative patients (n = 410) | |
| --- | --- | --- | --- | --- | --- |
|  |  | Chi2** | p-value | Chi2 | p-value |
| Lo/Med/Hi | FOXM1 | 24.14 | <0.001 | 26.59 | <0.001 |
|  | E2F1 | 25.28 | <0.001 | 15.56 | <0.001 |
|  | HMGB2 | 10.89 | <0.001 | 7.47 | 0.006 |
|  | MYBL2 | 25.43 | <0.001 | 15.91 | <0.001 |

TABLE 4-continued

Multi-variate Cox regression analysis using a standard clinical variable model* in the combined microarray datasets

|  | | All patients (n = 567) | | Node negative patients (n = 410) | |
|---|---|---|---|---|---|
| | Variable | Chi2** | p-value | Chi2 | p-value |
| | PTTG1 | 12.37 | <0.001 | 10.16 | 0.001 |
| | UHRF1 | 22.71 | <0.001 | 17.61 | <0.001 |
| | CDKN2A | 2.23 | 0.135 | 13.82 | <0.001 |
| | 6MTR | 33.80 | <0.001 | 20.27 | <0.001 |
| | OncoMasTR RNA score | 43.87 | <0.001 | 44.04 | <0.001 |
| | 21 gene | 29.02 | <0.001 | 38.03 | <0.001 |
| | Ki67 | 8.30 | 0.004 | 7.45 | 0.006 |
| Lo/Hi | 6MTR | 23.82 | <0.001 | 29.32 | <0.001 |
| | OncoMasTR RNA score | 29.62 | <0.001 | 32.20 | <0.001 |
| | 70 gene | 30.20 | <0.001 | 28.88 | <0.001 |
| | Ki67 | 5.52 | 0.018 | 8.99 | 0.003 |

*Clinical variables used: Age (>=50 years), Nodal status, Tumor size (>=2 cm), Tumor grade (>1), treatment (endocrine therapy) and ER status.
**Added prognostic value of each variable, represented by change in the Chi2 value from the model of only clinical variables to the model of clinical variable + marker in the three combined microarray datasets. Recurrence-free survival was used as the endpoint for this analysis.

TABLE 5

Multi-variate Cox regression analysis using a standard clinical variable model* in tissue microarrays

|  | | All patients (n = 272) | | Node negative patients (n = 171) | |
|---|---|---|---|---|---|
| | Variable | Chi2** | p-value | Chi2 | p-value |
| Lo/Hi | FOXM1 | 1.60 | 0.207 | 0.49 | 0.485 |
| | HMGB2 | 0.05 | 0.819 | 2.53 | 0.112 |
| | PTTG1 | 4.03 | 0.044 | 0.17 | 0.677 |
| | UHRF1 | 4.53 | 0.033 | 0.77 | 0.379 |
| | p16 | 6.73 | 0.009 | 7.23 | 0.007 |
| | 4 MTRS | 12.24 | <0.001 | 0.28 | 0.597 |
| | OncoMasTR IHC score | 24.86 | <0.001 | 7.28 | 0.007 |
| | Ki67 | 5.23 | 0.022 | 3.42 | 0.064 |

*Clinical variables used: Age (>=50 years), Nodal status, Tumor size (>=2 cm), tumor grade (>1), treatment (chemotherapy, endocrine therapy, radiotherapy), ER and HER2 status.
**Added prognostic value of each variable, represented by change in the Chi2 value from the model of only clinical variables to the model of clinical variable + marker in the tissue microarray datasets. Recurrence-free survival was used as the endpoint for this analysis.

Prognostic Power in a Prostate Cancer Cohort

Figure 10:
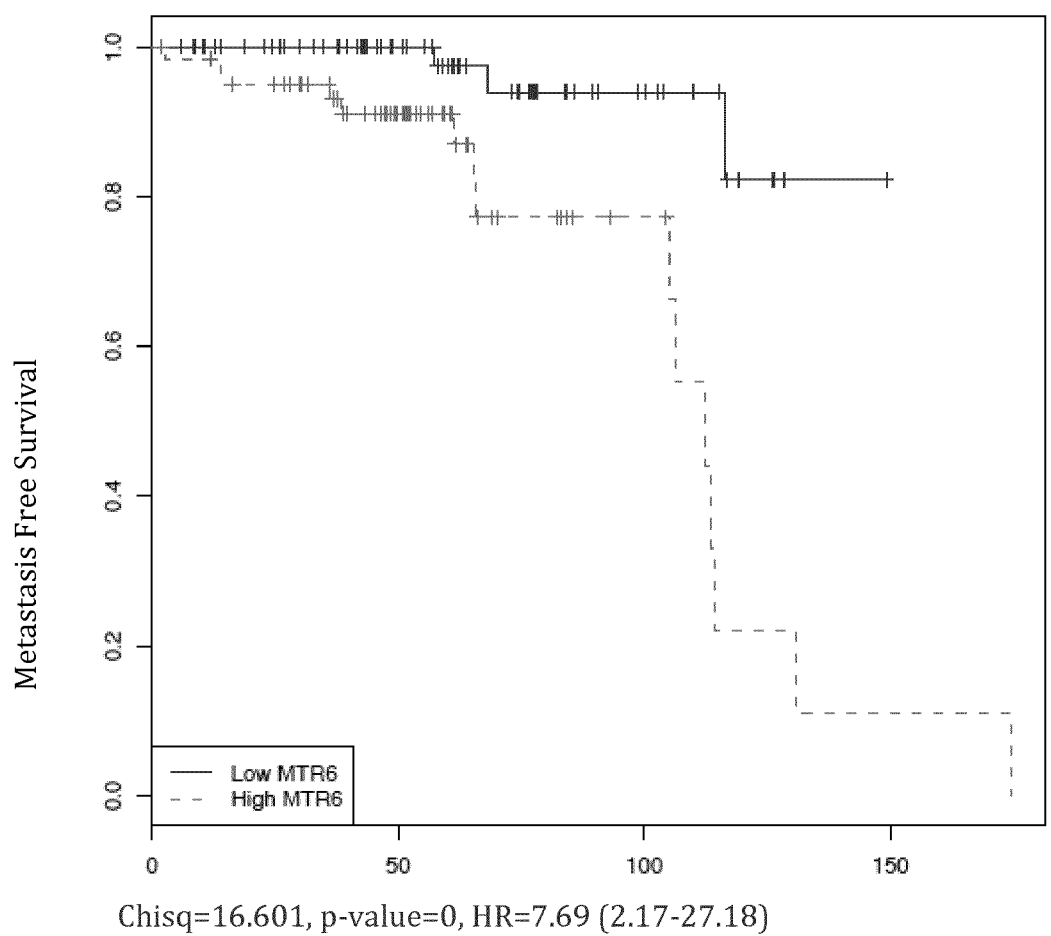
FIG. 10 illustrates Kaplan-Meier survival curves for 6 MTRs (FOXM1, UHRF1, MYBL2, HMGB2, E2F1, PTTG1) in The Cancer Genome Atlas (TGCA) prostate cancer transcriptomic dataset (n=150) in terms of metastasis-free survival.

This current project describes the validation of the OncoMasTR panel as a breast cancer prognostic on independent cohorts, however the panel may also be used for other cancer types such as those listed above. For example, a publically available prostate cancer transcriptomic dataset was analysed (Taylor et al., 2010), revealing that the OncoMasTR panel showed prognostic capability in terms of metastasis-free survival in this cancer type (see FIG. 10). Prostate cancer patients with high expression of the 6 MTR panel (FOXM1, E2F1, MYBL2, UHRF1, PTTG1, HMGB2) were found to have a poor outcome in comparison to patients with low expression of these genes.

A method of prediction based on the expression of these MTRs and p16$^{INK4A}$ will be capable of addressing the unmet need of early stage breast cancer patients, and provide them with the necessary tools to make better informed treatment decisions. The addition of additional pathway genes, or novel MTRs such as ATAD2, E2F8, ZNF367 and TCF19, some of which have been demonstrated to predict poor prognosis in breast cancer patients (FIG. 9); may also improve the prognostic capability of this assay even further. Such a test will improve on what is currently available based on the fact that each of these MTRs is upstream of many genes involved in breast cancer proliferation and thus, by measuring these MTRs, one is effectively measuring the status of a much larger 'proliferation signature'. The predictive power of this panel of proliferation MTRs has been augmented by the addition of the senescence regulator p16$^{INK4A}$. By combining these 'core' genes with selected 'pathway' genes, one can thoroughly dissect the molecular complexities of breast cancer, and accurately determine the likelihood of recurrence.

The prognostic potential of these 10 MTRs, in combination with p16$^{INK4A}$, were subsequently individually analysed using BreastMark (Madden, S. F. et al. BreastMark: an integrated approach to mining publicly available transcriptomic datasets relating to breast cancer outcome. *Breast Cancer Res* 15, R52, doi:10.1186/bcr3444 (2013)), an integrated approach for performing cross-dataset survival analysis in breast cancer (Table 6). This algorithm integrates gene expression and survival data from 26 datasets on 12 different microarray platforms corresponding to approximately 17,000 genes in up to 4,738 samples. The breakdown of the individual clinical information available with each dataset is described in detail in the original manuscript, along with the methods used for analysing/normalising the gene expression data. Cross-dataset survival analysis across multiple disparate microarray platforms is facilitated by gene centring the data to remove probe specific information and dichotomising the samples within each dataset before combining them to perform a global pooled survival analysis. In the analysis presented herein, disease free survival (DFS) was chosen as the survival endpoint and median gene expression was used to dichotomise the data.

There are over a 1,000 combinations of MTRs with four or more genes that can be chosen from the list of 10 MTRs described herein, each of which can be combined and assessed for their prognostic potential. In order to identify the optimal combination of these MTRs, BreastMark was adapted in the following way. For each combination of MTRs, the processed datasets from BreastMark were taken and, within each dataset, the expression data of each MTR was divided at the median into two groups. Once the samples have been dichotomised, the gene expression data is no longer used, allowing comparisons across different datasets/platforms. To generate a combined master transcriptional regulator (MTR) score, the gene expression values for each of the MTR in a particular combination were divided at the median, given a score of 1 or 2 based on the expression level. This results in each sample in a particular dataset getting a MTR score based on the sum of its individual MTR scores. For example, if a particular MTR combination contained 6 genes, and each gene in a particular sample was expressed at a level below the median expression of that gene in that dataset, the MTR score would be 6, the sum of the score of 1 for each of the 6 MTR. This results in a range of MTR scores between 6 (all MTRs are lowly expressed) and 12 (all MTRs are highly expressed), which can then be dichotomised based on the median MTR score for that dataset and combined with the DFS information to identify if this combination of MTRs is prognostic (a significant p-value) and how prognostic it is (the hazard ratio).

Figure 11:
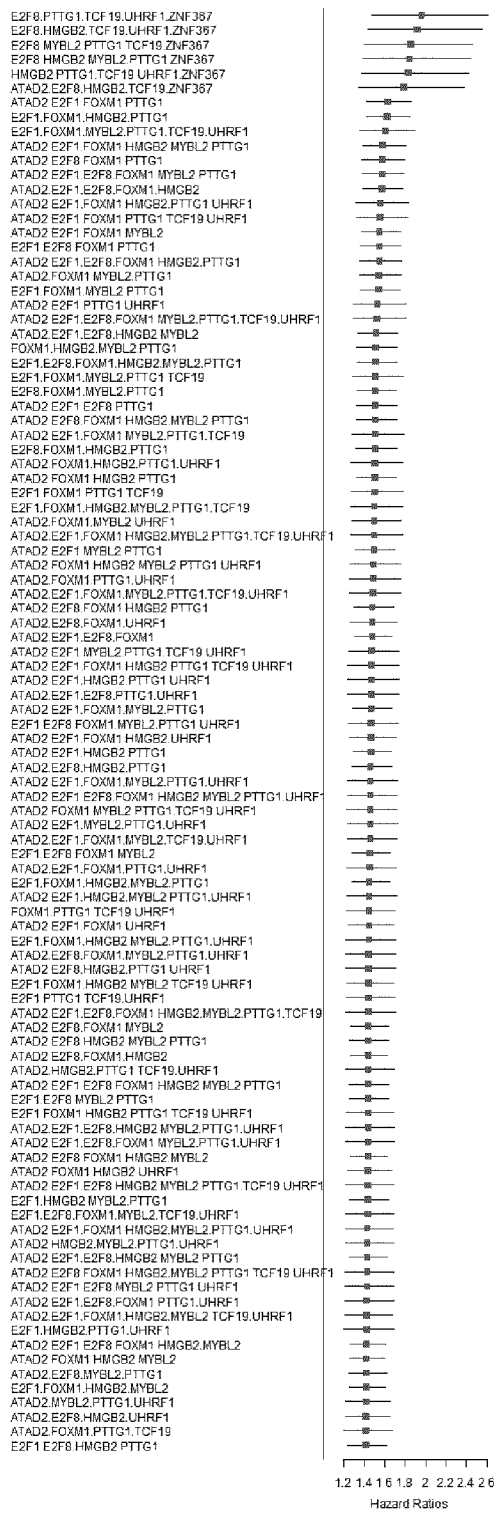
FIG. 11 illustrates a Forest plot of the top 100 combinations of MTRs from the list of 10 MTRs described here, with at least 4 MTRs in each combination.
Figure 12:
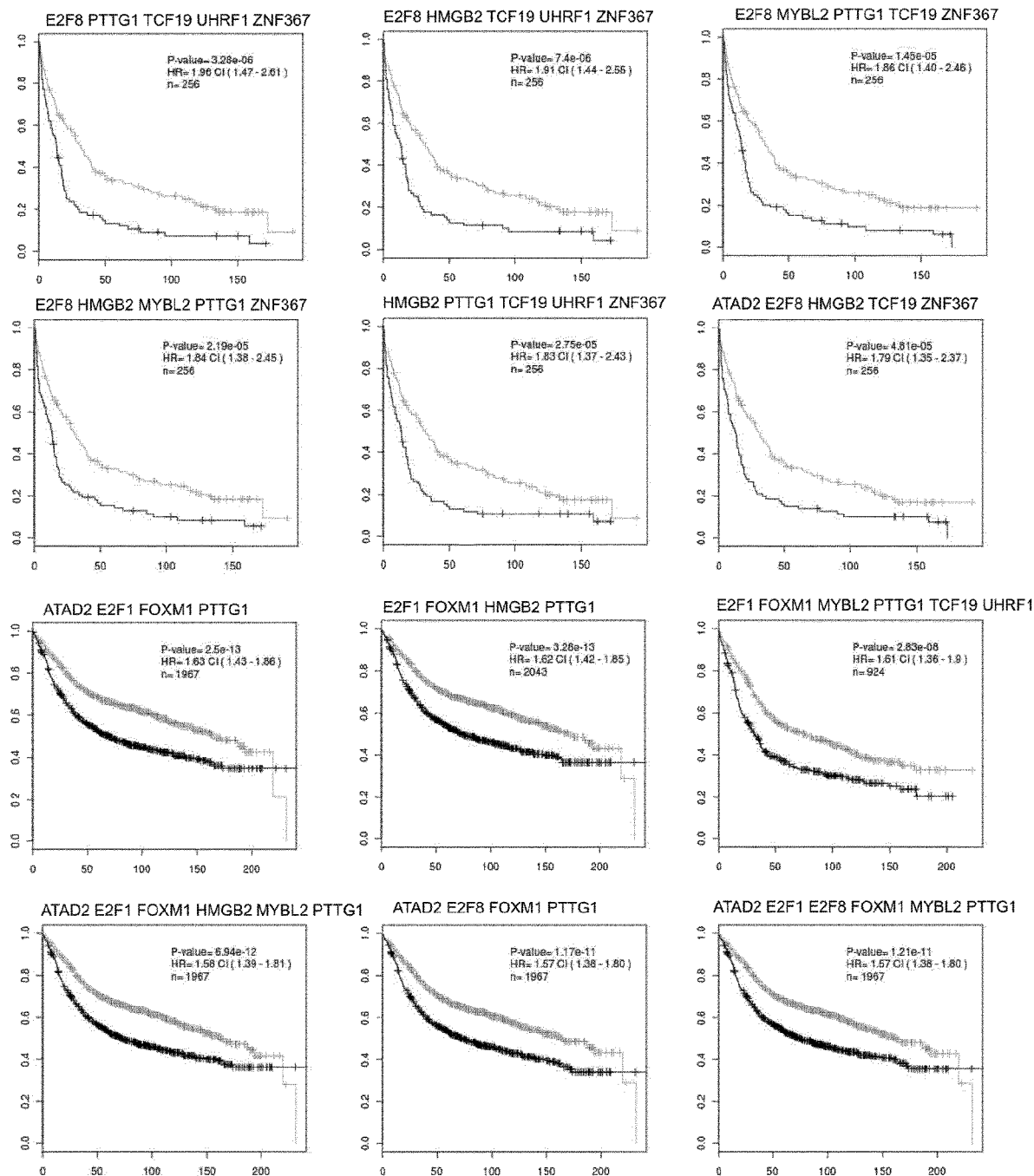
FIG. 12 illustrates Kaplan-Meier plots of the top 24 MTR combinations. In each case, the black line refers to high expression of the marker combination and grey refers to low expression of the marker combination.
Figure 12:
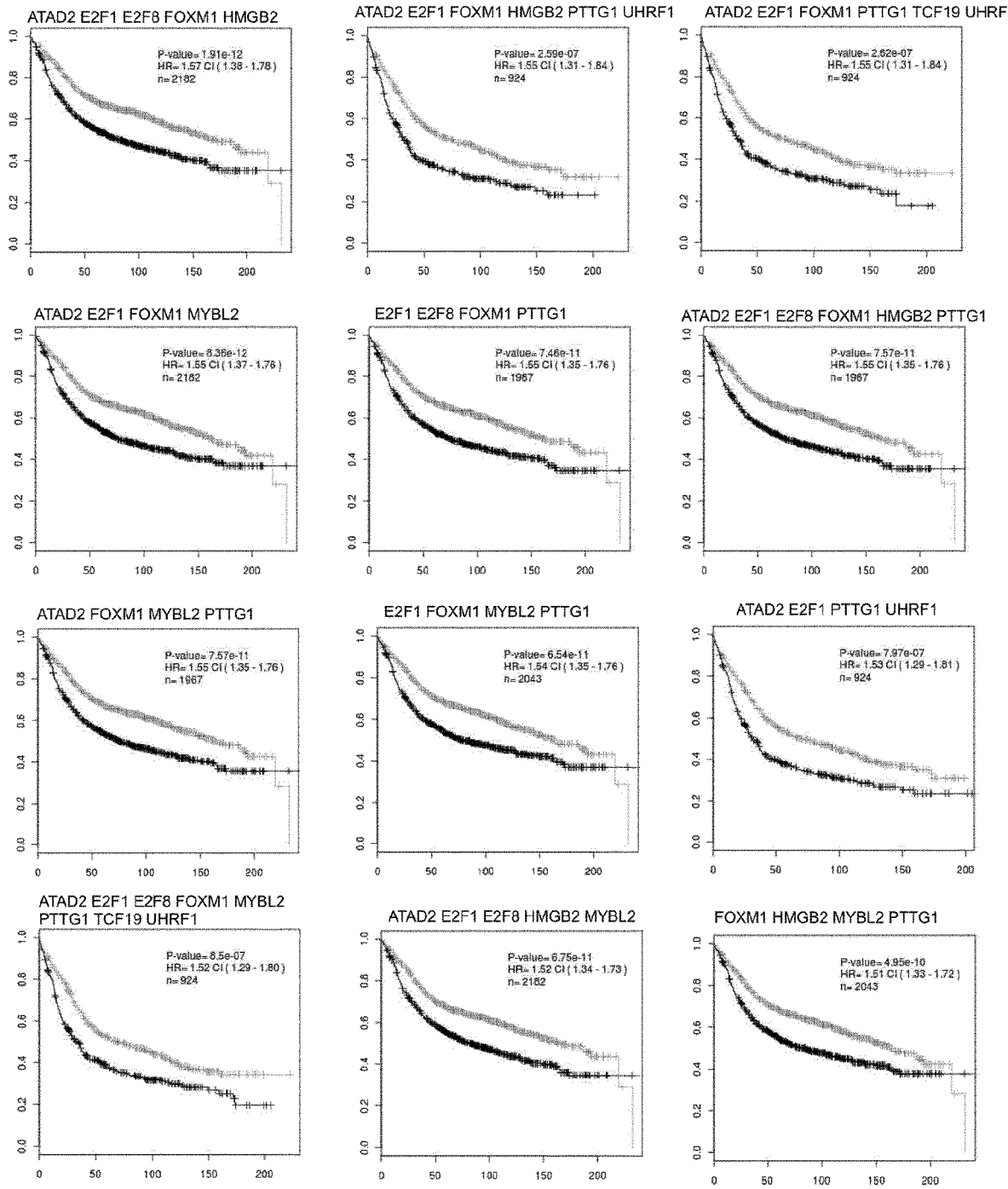

The top 100 combination of MTRs can be seen in the forest plot in FIG. 11, and the individual Kaplan-Meier plots for the top 24 combinations can be seen in FIG. 12. The samples were ranked based on the size of the hazard ratio once significance had been established (adjusting for multiple testing using the Benjamini and Hochberg method (Benjamini, Y., Drai, D., Elmer, G., Kafkafi, N. & Golani, I. Controlling the false discovery rate in behavior genetics research. Behavioural brain research 125, 279-284 (2001)). It should be noted that the sample sizes vary depending on the combination of MTRs used as not all MTRs are present in all 26 BreastMark datasets, e.g. ZNF367 is only present in four datasets totalling 295 samples.

TABLE 6

Individual breast cancer survival analysis of the top ten Master Transcriptional Regulators identified by ARACNe, using the BreastMark algorithm.

| Transcription Factor | Entrez Gene ID | Hazard Ratio | P-value | Sample Number |
|---|---|---|---|---|
| ATAD2 | 29028 | 1.378 (1.224-1.552) | 1.03E−07 | 2576 |
| E2F1 | 1869 | 1.301 (1.15-1.472) | 2.92E−05 | 2357 |
| E2F8 | 79733 | 1.375 (1.214-1.558) | 4.74E−07 | 2281 |
| FOXM1 | 2305 | 1.578 (1.392-1.788) | 5.45E−13 | 2357 |
| HMGB2 | 3148 | 1.271 (1.122-1.439) | 0.0001493 | 2357 |
| MYBL2 | 4605 | 1.506 (1.339-1.694) | 7.08E−12 | 2652 |
| PTTG1 | 9232 | 1.586 (1.402-1.794) | 1.25E−13 | 2437 |
| TCF19 | 6941 | 1.27 (1.097-1.471) | 0.00136 | 1378 |
| UHRF1 | 29128 | 1.318 (1.144-1.52) | 0.0001328 | 1533 |
| ZNF367 | 195828 | 1.08 (0.8274-1.41) | 0.571 | 295 |

Based on the mechanistic data underpinning the OncoMasTR panel, the applicants also believe the predictive power of the panel will have a capacity in predicting response to CDK4/6 inhibitors such as palbociclib. Palbociclib is an orally active, highly selective inhibitor of the cyclin-dependent kinases CDK4/6, which was initially assessed as a combination therapy with letrozole in advanced ER+ Her2+ breast cancer, in the PALOMA-1 trial (Richard S. Finn, 2014). Results from this trial have shown that the addition of palbociclib to a standard regimen extends survival by 10 months, which is a very promising result in these late-stage patients. Based on the mechanistic data underpinning OncoMasTR, the Applicant believes that it is likely to have predictive utility in terms of response to this novel therapy.

Calculating the MTR10+CDKN2A Signature Score in Pablociclib Treated Cell Lines

Figure 13:
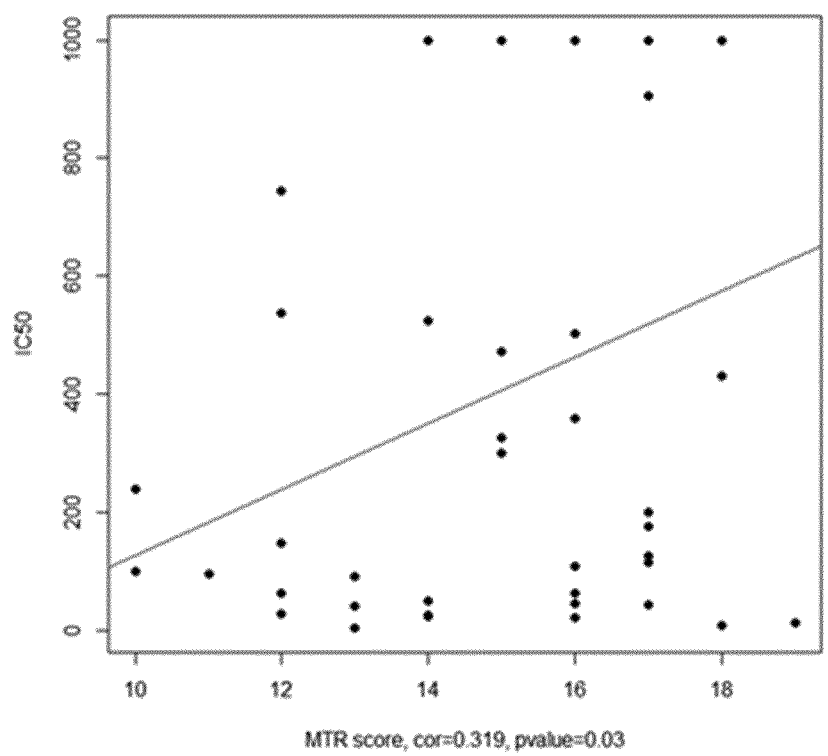
FIG. 13 illustrates the MTR10 and CDKN2A signature score in pablociclib treated human cell lines.

Pablociclib is an inhibitor of cyclin D kinases and its effects on human breast cancer cell lines were examined previously by Finn et al. Briefly, 47 human cell lines, representing the molecular subtypes of breast cancer, were treated with pablociclib and their gene expression profiles, along their IC50 values, were calculated. The gene expression data was downloaded from the Gene Expression Omnibus for the 47 cell lines, along with the accompanying IC50 data (accession number GSE18496). The gene expression data for the 10 MTRs described here was split on a gene by gene basis using median expression across all cell lines as a cut-off. Those cell lines with greater or lower than median expression of a gene were given a value of 2 or 1 for that gene, respectively. This was repeated for each of the ten genes. The expression of CDKN2A across the cell lines was split equally in three, those cell lines with high or low expression were given a value of 2 and those with an intermediate expression level were given a value of 1. A score was then calculated for each cell line by summing the individual gene scores. FIG. 13 shows a plot of IC50 values versus the signature score (correlation co-efficient=0.319, p-value=0.03). The significant p-value from the in vitro data suggests that the MTRs can provide predictive value in respect of patients receiving CDK4/6 inhibitors to treat cancer.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described but may be varied in both construction and detail.

REFERENCES

Boffetta, P., and Kaldor, J. M. (1994). Secondary malignancies following cancer chemotherapy. Acta Oncol 33, 591-598.

Boonyamtanakornkit, V., Melvin, V., Prendergast, P., Altmann, M., Ronfani, L., Bianchi, M. E., Taraseviciene, L., Nordeen, S. K., Allegretto, E. A., and Edwards, D. P. (1998). High-mobility group chromatin proteins 1 and 2 functionally interact with steroid hormone receptors to enhance their DNA binding in vitro and transcriptional activity in mammalian cells. Mol Cell Biol 18, 4471-4487.

Bostick, M., Kim, J. K., Esteve, P. O., Clark, A., Pradhan, S, and Jacobsen, S. E. (2007). UHRF1 plays a role in maintaining DNA methylation in mammalian cells. Science 317, 1760-1764.

Bracken, A. P., Dietrich, N., Pasini, D., Hansen, K. H., and Helin, K. (2006). Genome-wide mapping of Polycomb target genes unravels their roles in cell fate transitions. Genes Dev 20, 1123-1136.

Bracken, A. P., Pasini, D., Capra, M., Prosperini, E., Colli, E., and Helin, K. (2003). EZH2 is downstream of the pRB-E2F pathway, essential for proliferation and amplified in cancer. The EMBO journal 22, 5323-5335.

Buffa, F. M., Camps, C., Winchester, L., Snell, C. E., Gee, H. E., Sheldon, H., Taylor, M., Harris, A. L., and Ragoussis, J. (2011). microRNA-associated progression pathways and potential therapeutic targets identified by integrated mRNA and microRNA expression profiling in breast cancer. Cancer Res 71, 5635-5645.

Cancer Genome Atlas, N. (2012). Comprehensive molecular portraits of human breast tumours. Nature 490, 61-70.

Cardoso, F., Van't Veer, L., Rutgers, E., Loi, S., Mook, S., and Piccart-Gebhart, M. J. (2008). Clinical application of the 70-gene profile: the MINDACT trial. J Clin Oncol 26, 729-735.

Carro, M. S., Lim, W. K., Alvarez, M. J., Bollo, R. J., Zhao, X., Snyder, E. Y., Sulman, E P, Anne, S. L., Doetsch, F., Colman, H, et al. (2010). The transcriptional network for mesenchymal transformation of brain tumours. Nature 463, 318-325.

Curtis, C., Shah, S. P., Chin, S. F., Turashvili, G., Rueda, O. M., Dunning, M. J., Speed, D., Lynch, A. G., Samarajiwa, S., Yuan, Y., et al. (2012). The genomic and transcriptomic architecture of 2,000 breast tumours reveals novel subgroups. Nature.

ExPO available on the world wide web at wwwintgenorg/expo/.

Fan, C., Oh, D. S., Wessels, L., Weigelt, B., Nuyten, D. S., Nobel, A. B., van't Veer, L. J., and Perou, C. M. (2006). Concordance among gene-expression-based predictors for breast cancer. N Engl J Med 355, 560-569.

Finn at al, Breast Cancer Res. 2009; 11(5):R77. doi: 10.1186/bcr2419

Fisher, B., Jeong, J. H., Bryant, J., Anderson, S., Dignam, J, Fisher, E. R., and Wolmark, N. (2004). Treatment of lymph-node-negative, oestrogen-receptor-positive breast cancer: long-term findings from National Surgical Adjuvant Breast and Bowel Project randomised clinical trials. Lancet 364, 858-868.

Garbe, J. C., Bhattacharya, S., Merchant, B., Bassett, E., Swisshelm, K., Feiler, H. S., Wyrobek, A. J., and Stampfer, M. R. (2009). Molecular distinctions between stasis and telomere attrition senescence barriers shown by long-term culture of normal human mammary epithelial cells. Cancer Res 69, 7557-7568.

Goldhirsch, A., Glick, J. H., Gelber, R. D., Coates, A. S., and Senn, H. J. (2001). Meeting highlights: International Consensus Panel on the Treatment of Primary Breast Cancer. Seventh International Conference on Adjuvant Therapy of Primary Breast Cancer. J Clin Oncol 19, 3817-3827.

Haibe-Kains, B., Desmedt, C., Piette, F., Buyse, M., Cardoso, F., Van't Veer, L., Piccart, M., Bontempi, G., and Sotiriou, C. (2008). Comparison of prognostic gene expression signatures for breast cancer. BMC Genomics 9, 394.

Hara, E., Smith, R., Parry, D., Tahara, H., Stone, S., and Peters, G. (1996). Regulation of p16CDKN2 expression and its implications for cell immortalization and senescence. Mol Cell Biol 16, 859-867.

Hokamp, K., Roche, F. M., Acab, M., Rousseau, M. E., Kuo, B., Goode, D., Aeschliman, D, Bryan, J., Babiuk, L. A., Hancock, R. E., and Brinkman, F S (2004). ArrayPipe: a flexible processing pipeline for microarray data. Nucleic Acids Res 32, W457-459.

Hui, R., Macmillan, R. D., Kenny, F. S., Musgrove, E. A., Blamey, R. W., Nicholson, R. I., Robertson, J. F., and Sutherland, R. L. (2000). INK4a gene expression and methylation in primary breast cancer: overexpression of p16INK4a messenger RNA is a marker of poor prognosis. Clin Cancer Res 6, 2777-2787.

Ivshina, A. V., George, J., Senko, O., Mow, B., Putti, T. C., Smeds, J., Lindahl, T., Pawitan, Y., Hall, P., Nordgren, H., et al. (2006). Genetic reclassification of histologic grade delineates new clinical subtypes of breast cancer. Cancer Res 66, 10292-10301.

Kotake, Y., Cao, R., Viatour, P., Sage, J., Zhang, Y., and Xiong, Y. (2007). pRB family proteins are required for H3K27 trimethylation and Polycomb repression complexes binding to and silencing p16INK4alpha tumor suppressor gene. Genes Dev 21, 49-54.

Laoukili, J., Kooistra, M. R., Bras, A., Kauw, J., Kerkhoven, R. M., Morrison, A., Clevers, H., and Medema, R. H. (2005). FoxMl is required for execution of the mitotic programme and chromosome stability. Nat Cell Biol 7, 126-136.

Li, Y., Nichols, M. A., Shay, J. W., and Xiong, Y. (1994). Transcriptional repression of the D-type cyclin-dependent kinase inhibitor p16 by the retinoblastoma susceptibility gene product pRb. Cancer Res 54, 6078-6082.

Liu, R., Wang, X., Chen, G. Y., Dalerba, P., Gurney, A., Hoey, T., Sherlock, G., Lewicki, J., Shedden, K., and Clarke, M. F. (2007). The prognostic role of a gene signature from tumorigenic breast-cancer cells. N Engl J Med 356, 217-226.

Loi, S., Haibe-Kains, B., Desmedt, C., Lallemand, F, Tutt, A. M., Gillet, C., Ellis, P., Harris, A., Bergh, J., Foekens, J. A., et al. (2007). Definition of clinically distinct molecular subtypes in estrogen receptor-positive breast carcinomas through genomic grade. J Clin Oncol 25, 1239-1246.

Margolin, A. A., Wang, K., Lim, W. K., Kustagi, M., Nemenman, I, and Califano, A. (2006). Reverse engineering cellular networks. Nat Protoc 1, 662-671.

Milde-Langosch, K., Bamberger, A. M., Rieck, G., Kelp, B., and Loning, T. (2001). Overexpression of the p16 cell cycle inhibitor in breast cancer is associated with a more malignant phenotype. Breast Cancer Res Treat 67, 61-70.

Mosley, J. D., and Keri, R. A. (2008). Cell cycle correlated genes dictate the prognostic power of breast cancer gene lists. BMC Med Genomics 1, 11.

Oh, I. H., and Reddy, E. P. (1998). The C-terminal domain of B-Myb acts as a positive regulator of transcription and modulates its biological functions. Mol Cell Biol 18, 499-511.

Peurala, E., Koivunen, P., Haapasaari, K. M., Bloigu, R., and Jukkola-Vuorinen, A. (2013). The prognostic significance and value of cyclin D1, CDK4 and p16 in human breast cancer. Breast Cancer Res 15, R5.

Richard S. Finn, J. P. C., Istvan Lang, Katalin Boer, Igor M. Bondarenko, Sergey O. Kulyk, Johannes Ettl, Ravindranath Patel, Tamas Pinter, Marcus Schmidt, Yaroslav V. Shparyk, Anu R Thummala, Nataliya L. Voytko, Xin Huang, Sindy T. Kim, Sophia S. Randolph, Dennis J. Slamon (2014). Final results of a randomized Phase II study of PD 0332991, a cyclin-dependent kinase (CDK)-4/6 inhibitor, in combination with letrozole vs letrozole alone for first-line treatment of ER+/HER2– advanced breast cancer (PALOMA-1; TRIO-18). Proceedings of the 105th Annual Meeting of the American Association for Cancer Research.

Sotiriou, C., Wirapati, P., Loi, S., Harris, A., Fox, S., Smeds, J., Nordgren, H., Farmer, P., Praz, V., Haibe-Kains, B., et al. (2006). Gene expression profiling in breast cancer: understanding the molecular basis of histologic grade to improve prognosis. J Natl Cancer Inst 98, 262-272.

Sparano, J. A. (2006). TAILORx: trial assigning individualized options for treatment (Rx). Clin Breast Cancer 7, 347-350.

Svensson, S., Jirstrom, K., Ryden, L., Roos, G., Emdin, S, Ostrowski, M. C., and Landberg, G. (2005). ERK phosphorylation is linked to VEGFR2 expression and Ets-2 phosphorylation in breast cancer and is associated with tamoxifen treatment resistance and small tumours with good prognosis. Oncogene 24, 4370-4379.

Tam, S. W., Shay, J. W., and Pagano, M. (1994). Differential expression and cell cycle regulation of the cyclin-dependent kinase 4 inhibitor p16Ink4. Cancer Res 54, 5816-5820.

Tong, Y., and Eigler, T. (2009). Transcriptional targets for pituitary tumor-transforming gene-1. J Mol Endocrinol 43, 179-185.

Taylor, B. S., Schultz, N., Hieronymus, H., Gopalan, A., Xiao, Y., Carver, B. S., Arora, V. K., Kaushik, P., Cerami, E., Reva, B., et al. (2010). Integrative genomic profiling of human prostate cancer. Cancer Cell 18, 11-22.

Tong, Y., Tan, Y., Zhou, C., and Melmed, S. (2007). Pituitary tumor transforming gene interacts with Sp1 to modulate G1/S cell phase transition. Oncogene 26, 5596-5605.

van't Veer, L. J., Dai, H., van de Vijver, M. J., He, Y. D., Hart, A. A., Mao, M., Peterse, H. L., van der Kooy, K., Marton, M. J., Witteveen, A. T., et al. (2002). Gene expression profiling predicts clinical outcome of breast cancer. Nature 415, 530-536.

Wang, Y., Klijn, J. G., Zhang, Y., Sieuwerts, A. M., Look, M. P., Yang, F., Talantov, D., Timmermans, M., Meijer-van Gelder, M. E., Yu, J., et al. (2005). Gene-expression profiles to predict distant metastasis of lymph-node-negative primary breast cancer. Lancet 365, 671-679.

Wirapati, P., Sotiriou, C., Kunkel, S., Farmer, P., Pradervand, S., Haibe-Kains, B., Desmedt, C., Ignatiadis, M., Sengstag, T., Schutz, F., et al. (2008). Meta-analysis of gene expression profiles in breast cancer: toward a unified understanding of breast cancer subtyping and prognosis signatures. Breast Cancer Res 10, R65.

Wu, L., Timmers, C., Maiti, B., Saavedra, H. I., Sang, L., Chong, G. T., Nuckolls, F., Giangrande, P., Wright, F. A., Field, S. J., et al. (2001). The E2F1-3 transcription factors are essential for cellular proliferation. Nature 414, 457-462.

Zindy, F., Quelle, D. E., Roussel, M. F., and Sherr, C. J. (1997). Expression of the p16INK4a tumor suppressor versus other INK4 family members during mouse development and aging. Oncogene 15, 203-211.

The invention claimed is:

1. A method of treating breast cancer in a patient in need thereof, the method comprising:
    assaying a cancer sample from the patient for positive expression of at least FOXM1, PTTG1, and ZNF367;
    detecting positive expression of at least FOXM1, PTTG1, and ZNF367; and administering a neoadjuvant or an adjuvant therapy or combination of both.

2. The method according to claim 1, wherein the neoadjuvant therapy and adjuvant therapy is an agent selected from the group consisting of:
    trastuzumab, lapatinib, neratinib, afatinib, pertuzumab, CDK 4/6 inhibitors, cyclophosphamide, methotrexate, 5-fluorouracil, gemcitabine, adriamycin (doxorubicin), epirubucin, docetaxel, paclitaxel, capecitabine, and tamoxifen.

3. The method according to claim 1, the method further comprising the step of assaying for the expression of p16$^{INK4A}$ gene or a protein encoded by said gene.

4. The method according to claim 1, further comprising assaying the cancer sample from the patient for positive expression of MYBL2.

5. The method according to claim 1, further comprising assaying the cancer sample from the patient for positive expression of E2F8.

6. The method according to claim 1, further comprising assaying the cancer sample from the patient for positive expression of HMGB2.

7. The method according to claim 1, further comprising assaying the cancer sample from the patient for positive expression of ATAD2.

8. The method according to claim 1, further comprising assaying the cancer sample from the patient for positive expression of E2F1.

9. The method according to claim 1, further comprising assaying the cancer sample from the patient for positive expression of TCF19.

10. A method of treating breast cancer in a subject in need thereof, the method comprising:
    being provided information comprising an indication of positive expression of at least FOXM1, PTTG1, and ZNF367 in a cancer sample from a subject; and
    then administering a neoadjuvant or an adjuvant therapy or combination of both to the subject.

11. The method according to claim 10, wherein the neoadjuvant therapy and adjuvant therapy is an agent selected from the group consisting of:
    trastuzumab, lapatinib, neratinib, afatinib, pertuzumab, CDK4/6 inhibitors, cyclophosphamide, methotrexate, 5-fluorouracil, gemcitabine, adriamycin (doxorubicin), epirubucin, docetaxel, paclitaxel, capecitabine, and tamoxifen.

12. The method according to claim 10, wherein the subject is further determined to have dysregulated expression of p16$^{INK4A}$, in combination with positive expression of the at least three genes.

13. The method according to claim 10, wherein the patient is further determined to have positive expression of MYBL2.

14. The method according to claim 10, wherein the patient is further determined to have positive expression of E2F8.

15. The method according to claim 10, wherein the patient is further determined to have positive expression of HMGB2.

16. The method according to claim 10, wherein the patient is further determined to have positive expression of ATAD2.

17. The method according to claim 10, wherein the patient is further determined to have positive expression of E2F1.

18. The method according to claim 10, wherein the patient is further determined to have positive expression of TCF19.

* * * * *

SEQUENCE LISTING

```
<160> NUMBER OF SEQ ID NOS: 40

<210> SEQ ID NO 1
<211> LENGTH: 23
<212> TYPE: DNA
<213> ORGANISM: Artificial Sequence
<220> FEATURE:
<223> OTHER INFORMATION: Forward Primer for UHRF1

<400> SEQUENCE: 1
agaccgtcct caaccagctc ttc                                              23

<210> SEQ ID NO 2
<211> LENGTH: 21
<212> TYPE: DNA
<213> ORGANISM: Artificial Sequence
<220> FEATURE:
<223> OTHER INFORMATION: Reverse Primer for UHRF1

<400> SEQUENCE: 2
gaagtgcttg gagatcaccg g                                                21

<210> SEQ ID NO 3
<211> LENGTH: 25
<212> TYPE: DNA
<213> ORGANISM: Artificial Sequence
<220> FEATURE:
<223> OTHER INFORMATION: Forward Primer for FOXM1

<400> SEQUENCE: 3
caacaatagc ctatccaaca tccag                                            25

<210> SEQ ID NO 4
<211> LENGTH: 22
<212> TYPE: DNA
<213> ORGANISM: Artificial Sequence
<220> FEATURE:
<223> OTHER INFORMATION: Reverse Primer for FOXM1

<400> SEQUENCE: 4
ggagcccagt ccatcagaac tc                                               22

<210> SEQ ID NO 5
<211> LENGTH: 22
<212> TYPE: DNA
<213> ORGANISM: Artificial Sequence
<220> FEATURE:
<223> OTHER INFORMATION: Forward Primer for PTTG1

<400> SEQUENCE: 5
ctgcctgaag agcaccagat tg                                               22

<210> SEQ ID NO 6
<211> LENGTH: 22
<212> TYPE: DNA
<213> ORGANISM: Artificial Sequence
```

<220> FEATURE:
<223> OTHER INFORMATION: Reverse Primer for PTTG1

<400> SEQUENCE: 6
caaggatcat gagaggcact cc                                      22

<210> SEQ ID NO 7
<211> LENGTH: 22
<212> TYPE: DNA
<213> ORGANISM: Artificial Sequence
<220> FEATURE:
<223> OTHER INFORMATION: Forward Primer for MYBL2

<400> SEQUENCE: 7
cactgaccag caatgccagt ac                                      22

<210> SEQ ID NO 8
<211> LENGTH: 22
<212> TYPE: DNA
<213> ORGANISM: Artificial Sequence
<220> FEATURE:
<223> OTHER INFORMATION: Reverse Primer for MYBL2

<400> SEQUENCE: 8 cccctttgaca aggtctggat tc                                     22

<210> SEQ ID NO 9
<211> LENGTH: 22
<212> TYPE: DNA
<213> ORGANISM: Artificial Sequence
<220> FEATURE:
<223> OTHER INFORMATION: Forward Primer for HMGB2

<400> SEQUENCE: 9
gctcctaaaa ggccaccatc tg                                      22

<210> SEQ ID NO 10
<211> LENGTH: 21
<212> TYPE: DNA
<213> ORGANISM: Artificial Sequence
<220> FEATURE:
<223> OTHER INFORMATION: Reverse Primer for HMGB2

<400> SEQUENCE: 10
tgatctttgg gcgatgttca g                                       21

<210> SEQ ID NO 11
<211> LENGTH: 22
<212> TYPE: DNA
<213> ORGANISM: Artificial Sequence
<220> FEATURE:
<223> OTHER INFORMATION: Forward Primer for E2F1

<400> SEQUENCE: 11
tgtcaggacc ttcgtagcat tg                                      22

<210> SEQ ID NO 12
<211> LENGTH: 23
<212> TYPE: DNA
<213> ORGANISM: Artificial Sequence
<220> FEATURE:
<223> OTHER INFORMATION: Reverse Primer for E2F1

<400> SEQUENCE: 12
gggctttgat caccataacc atc                                     23

<210> SEQ ID NO 13
<211> LENGTH: 22
<212> TYPE: DNA
<213> ORGANISM: Artificial Sequence
<220> FEATURE:
<223> OTHER INFORMATION: Forward Primer for E2F8

<400> SEQUENCE: 13
caatctcaac aaaacccttg gc                                                22

<210> SEQ ID NO 14
<211> LENGTH: 22
<212> TYPE: DNA
<213> ORGANISM: Artificial Sequence
<220> FEATURE:
<223> OTHER INFORMATION: Reverse Primer for E2F8

<400> SEQUENCE: 14
ctcggcgtac ttattctcct cc                                                22

<210> SEQ ID NO 15
<211> LENGTH: 22
<212> TYPE: DNA
<213> ORGANISM: Artificial Sequence
<220> FEATURE:
<223> OTHER INFORMATION: Forward Primer for INK4A

<400> SEQUENCE: 15
agaggatttg agggacaggg tc                                                22

<210> SEQ ID NO 16
<211> LENGTH: 20
<212> TYPE: DNA
<213> ORGANISM: Artificial Sequence
<220> FEATURE:
<223> OTHER INFORMATION: Reverse Primer for INK4A

<400> SEQUENCE: 16
cctctttctt cctccggtgc                                                   20

<210> SEQ ID NO 17
<211> LENGTH: 21
<212> TYPE: DNA
<213> ORGANISM: Artificial Sequence
<220> FEATURE:
<223> OTHER INFORMATION: Forward Primer for PITX

<400> SEQUENCE: 17
atggagctgg gtgctgagaa c                                                 21

<210> SEQ ID NO 18
<211> LENGTH: 22
<212> TYPE: DNA
<213> ORGANISM: Artificial Sequence
<220> FEATURE:
<223> OTHER INFORMATION: Reverse Primer for PITX

<400> SEQUENCE: 18
ccttcttcaa ctccatgagc cc                                                22

<210> SEQ ID NO 19
<211> LENGTH: 24
<212> TYPE: DNA
<213> ORGANISM: Artificial Sequence
<220> FEATURE:
<223> OTHER INFORMATION: Forward Primer for HSF4

```
<400> SEQUENCE: 19
acaaagaagg aaatagaggg accg                                           24

<210> SEQ ID NO 20
<211> LENGTH: 22
<212> TYPE: DNA
<213> ORGANISM: Artificial Sequence
<220> FEATURE:
<223> OTHER INFORMATION: Reverse Primer for HSF4

<400> SEQUENCE: 20
gatgagtggg agacttgggt tc                                             22

<210> SEQ ID NO 21
<211> LENGTH: 22
<212> TYPE: DNA
<213> ORGANISM: Artificial Sequence
<220> FEATURE:
<223> OTHER INFORMATION: Forward Primer for KLF6

<400> SEQUENCE: 21
cagcccgagc ttttgttaca ac                                             22

<210> SEQ ID NO 22
<211> LENGTH: 22
<212> TYPE: DNA
<213> ORGANISM: Artificial Sequence
<220> FEATURE:
<223> OTHER INFORMATION: Reverse Primer for KLF6

<400> SEQUENCE: 22
ttcgctgctg acatctgagt tc                                             22

<210> SEQ ID NO 23
<211> LENGTH: 22
<212> TYPE: DNA
<213> ORGANISM: Artificial Sequence
<220> FEATURE:
<223> OTHER INFORMATION: Forward Primer for ID2

<400> SEQUENCE: 23
aaggtgagca agatggaaat cc                                             22

<210> SEQ ID NO 24
<211> LENGTH: 23
<212> TYPE: DNA
<213> ORGANISM: Artificial Sequence
<220> FEATURE:
<223> OTHER INFORMATION: Reverse Primer for ID2

<400> SEQUENCE: 24
cgatctgcag gtccaagatg tag                                            23

<210> SEQ ID NO 25
<211> LENGTH: 22
<212> TYPE: DNA
<213> ORGANISM: Artificial Sequence
<220> FEATURE:
<223> OTHER INFORMATION: Forward Primer for SNAI1

<400> SEQUENCE: 25
ctctctgagg ccaaggatct cc                                             22

<210> SEQ ID NO 26
```

<211> LENGTH: 23
<212> TYPE: DNA
<213> ORGANISM: Artificial Sequence
<220> FEATURE:
<223> OTHER INFORMATION: Reverse Primer for SNAI1

<400> SEQUENCE: 26
ccttgttgca gtatttgcag ttg                                            23

<210> SEQ ID NO 27
<211> LENGTH: 22
<212> TYPE: DNA
<213> ORGANISM: Artificial Sequence
<220> FEATURE:
<223> OTHER INFORMATION: Forward Primer for CDH2

<400> SEQUENCE: 27
tgagcctgca gattttaagg tg                                             22

<210> SEQ ID NO 28
<211> LENGTH: 22
<212> TYPE: DNA
<213> ORGANISM: Artificial Sequence
<220> FEATURE:
<223> OTHER INFORMATION: Reverse Primer for CDH2

<400> SEQUENCE: 28
tggaaagctt ctcacggcat ac                                             22

<210> SEQ ID NO 29
<211> LENGTH: 23
<212> TYPE: DNA
<213> ORGANISM: Artificial Sequence
<220> FEATURE:
<223> OTHER INFORMATION: Forward Primer for CCNA2

<400> SEQUENCE: 29
agctggcctg aatcattaat acg                                            23

<210> SEQ ID NO 30
<211> LENGTH: 22
<212> TYPE: DNA
<213> ORGANISM: Artificial Sequence
<220> FEATURE:
<223> OTHER INFORMATION: Reverse Primer for CCNA2

<400> SEQUENCE: 30
ggtgaaggtc catgagacaa gg                                             22

<210> SEQ ID NO 31
<211> LENGTH: 23
<212> TYPE: DNA
<213> ORGANISM: Artificial Sequence
<220> FEATURE:
<223> OTHER INFORMATION: Forward Primer for EZH2

<400> SEQUENCE: 31
gggacagtaa aaatgtgtcc tgc                                            23

<210> SEQ ID NO 32
<211> LENGTH: 22
<212> TYPE: DNA
<213> ORGANISM: Artificial Sequence
<220> FEATURE:
<223> OTHER INFORMATION: Reverse Primer for EZH2

<400> SEQUENCE: 32
tgccagcaat agatgctttt tg          22

<210> SEQ ID NO 33
<211> LENGTH: 19
<212> TYPE: DNA
<213> ORGANISM: Artificial Sequence
<220> FEATURE:
<223> OTHER INFORMATION: Forward Primer for DEK

<400> SEQUENCE: 33
cattcccgct ctccttccc              19

<210> SEQ ID NO 34
<211> LENGTH: 18
<212> TYPE: DNA
<213> ORGANISM: Artificial Sequence
<220> FEATURE:
<223> OTHER INFORMATION: Reverse Primer for DEK

<400> SEQUENCE: 34
gctcggctcc ccagaatc               18

<210> SEQ ID NO 35
<211> LENGTH: 21
<212> TYPE: DNA
<213> ORGANISM: Artificial Sequence
<220> FEATURE:
<223> OTHER INFORMATION: Forward Primer for HELLS

<400> SEQUENCE: 35
cctcactgga ggagtgatgc g           21

<210> SEQ ID NO 36
<211> LENGTH: 22
<212> TYPE: DNA
<213> ORGANISM: Artificial Sequence
<220> FEATURE:
<223> OTHER INFORMATION: Reverse Primer for HELLS

<400> SEQUENCE: 36
aagcatccta agccattcca tg          22

<210> SEQ ID NO 37
<211> LENGTH: 22
<212> TYPE: DNA
<213> ORGANISM: Artificial Sequence
<220> FEATURE:
<223> OTHER INFORMATION: Forward Primer for E2F7

<400> SEQUENCE: 37
ccattgaaaa caaggacgat gc          22

<210> SEQ ID NO 38
<211> LENGTH: 21
<212> TYPE: DNA
<213> ORGANISM: Artificial Sequence
<220> FEATURE:
<223> OTHER INFORMATION: Reverse Primer for E2F7

<400> SEQUENCE: 38
ctgtccccaa caacatcaag c           21

<210> SEQ ID NO 39
<211> LENGTH: 18
<212> TYPE: DNA

```
<213> ORGANISM: Artificial Sequence
<220> FEATURE:
<223> OTHER INFORMATION: Forward Primre for RPLPO (Normaliser)

<400> SEQUENCE: 39
ttcattgtgg gagcagac                                                   18

<210> SEQ ID NO 40
<211> LENGTH: 18
<212> TYPE: DNA
<213> ORGANISM: Artificial Sequence
<220> FEATURE:
<223> OTHER INFORMATION: Reverse Primer for RPLPO (Normaliser)

<400> SEQUENCE: 40
cagcagtttc tccagagc                                                   18
```